United States Patent
Xiao et al.

(10) Patent No.: US 9,540,396 B2
(45) Date of Patent: Jan. 10, 2017

(54) 6-ARYLAMINO PYRIDONE CARBOXAMIDE AS MEK INHIBITORS

(75) Inventors: Dengming Xiao, Beijing (CN); Li Zhu, Beijing (CN); Yuandong Hu, Beijing (CN); Shixin Wang, Beijing (CN); Rong Yu, Beijing (CN); Wei Hu, Beijing (CN); Zhi Liang, Beijing (CN); Xijie Liu, Beijing (CN); Quan Hu, Beijing (CN)

(73) Assignees: Centaurus Biopharma Co., Ltd., Beijing (CN); Chia Tai Tianqing Pharmaceutical Group Co., Ltd., Jiangsu (CN)

( * ) Notice: Subject to any disclaimer, the term of this patent is extended or adjusted under 35 U.S.C. 154(b) by 627 days.

(21) Appl. No.: 13/996,233

(22) PCT Filed: Nov. 1, 2011

(86) PCT No.: PCT/CN2011/081643
§ 371 (c)(1),
(2), (4) Date: Nov. 21, 2013

(87) PCT Pub. No.: WO2012/059041
PCT Pub. Date: May 10, 2012

(65) Prior Publication Data
US 2014/0080804 A1 Mar. 20, 2014

Related U.S. Application Data

(60) Provisional application No. 61/344,998, filed on Dec. 6, 2010.

(30) Foreign Application Priority Data

Nov. 2, 2010 (CN) .......................... 2010 1 0528712

(51) Int. Cl.
| | | |
|---|---|---|
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |
| A61K 31/44 | (2006.01) |
| C07D 513/04 | (2006.01) |
| A61K 31/4355 | (2006.01) |
| A61K 31/4365 | (2006.01) |
| A61K 31/437 | (2006.01) |
| A61K 31/4545 | (2006.01) |
| A61K 31/5377 | (2006.01) |
| C07D 491/048 | (2006.01) |
| C07D 495/04 | (2006.01) |
| C07D 498/04 | (2006.01) |

(52) U.S. Cl.
CPC .......... *C07D 513/04* (2013.01); *A61K 31/437* (2013.01); *A61K 31/4355* (2013.01); *A61K 31/4365* (2013.01); *A61K 31/4545* (2013.01); *A61K 31/5377* (2013.01); *C07D 491/048* (2013.01); *C07D 495/04* (2013.01); *C07D 498/04* (2013.01)

(58) Field of Classification Search
None
See application file for complete search history.

(56) References Cited

U.S. PATENT DOCUMENTS

2009/0124595 A1* 5/2009 Adams ................. C07D 471/04
514/210.16

FOREIGN PATENT DOCUMENTS

| CN | 1905873 A | 1/2007 |
| WO | 2009/093013 A1 | 7/2009 |
| WO | WO 2010/145197 A1 * | 12/2010 |

OTHER PUBLICATIONS

Greenwald, RB. et al. Drug Delivery Systems: Water Soluble Taxol 2'-Poly(ethylene glycol) Ester Prodrugs—Design and in Vivo Effectiveness. J. Med. Chem. 1996, vol. 39, p. 425.*
Testa, B. et al. Lessons Learned from Marketed and Investigational Prodrugs. J. Med. Chem. 2004, vol. 47(10), p. 2393.*
Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
International Search Report corresponding to PCT/CN2011/081643 mailed Feb. 16, 2012 (5 pages).

* cited by examiner

*Primary Examiner* — Rita Desai
*Assistant Examiner* — Ben S Michelson
(74) *Attorney, Agent, or Firm* — Kilpatrick Townsend & Stockton LLP

(57) ABSTRACT

The invention provides novel substituted 6-arylamino pyridone carboxamides represented by Formula I, or a pharmaceutically acceptable salt, solvate, poly-morph, ester, tautomer or prodrug thereof, and a composition comprising these compounds. The compounds provided can be used as inhibitors of MEK and are useful in the treatment of inflammatory diseases, cancer and other hyperproliferative diseases. The invention further provides a method of treatment for inflammatory diseases, cancer and other hyperproliferative diseases in mammals, especially humans.

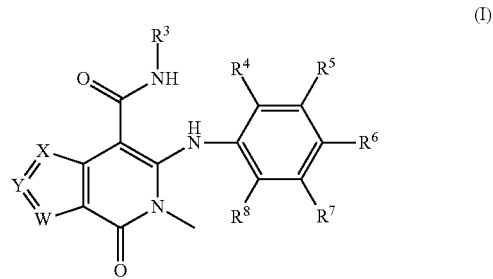

10 Claims, No Drawings

6-ARYLAMINO PYRIDONE CARBOXAMIDE AS MEK INHIBITORS

FIELD OF THE INVENTION

This invention relates to a series of substituted 6-arylamino pyridone carboxamides which are inhibitors of MEK and are useful in the treatment of inflammatory diseases, cancer and other hyperproliferative diseases. This invention also relates to a pharmaceutical composition comprising the compound of the invention, use of the compound in the preparation of a medicament, and method of treatment for hyperproliferative diseases in mammals, especially humans by administering the compound thereof.

BACKGROUND OF THE INVENTION

Protein kinases constitute a large family of structurally related enzymes that effect the transfer of a phosphate group from a nucleoside triphosphate to a Ser, Thr or Tyr residue on a protein acceptor. A vast array of cellular functions, including DNA replication, cell cycle progression, energy metabolism and cell growth and differentiation, are regulated by reversible protein phosphorylation events mediated by protein kinases. Additionally, protein kinase activity has been implicated in a number of diseases, including cancers. Of the >100 dominant oncogenes known to date, many encode receptor and cytoplasmic protein kinases known to be mutated and/or over expressed in human cancers (Blume-Jensen and Hunter, Nature, 411:355-365 (2001)). Accordingly, protein kinase targets have attracted substantial drug discovery efforts in recent years, with several protein kinase inhibitors achieving regulatory approval (reviewed in Fischer, Curr.'s Med. Chem., 11:1563 (2004); Dancey and Sausville, Nature Rev. Drug Disc., 2:296 (2003)).

The Ras/Raf/MEK/ERK pathway is a central signal transduction pathway, which transmits signals from multiple cell surface receptors to transcription factors in the nucleus which regulate gene expression. This pathway is frequently referred to as the MAP kinase pathway as MAPK stands for mitogen-activated protein kinase indicating that this pathway can be stimulated by mitogens, cytokines and growth factors (Steelman et al., Leukemia 2004, 18, 189-218). Depending upon the stimulus and cell type, this pathway can transmit signals, which result in the prevention or induction of apoptosis or cell cycle progression. The Ras/Raf/MEK/ERK pathway has been shown to play important roles in cell proliferation and the prevention of apoptosis. Aberrant activation of this pathway is commonly observed in malignantly transformed cells. Amplification of ras proto-oncogenes and activating mutations that lead to the expression of constitutively active Ras proteins are observed in approximately 30% of all human cancers (Stirewalt et al., Blood 2001, 97, 3589-95). Mutated, oncogenic forms of Ras are found in 50% of colon and >90% pancreatic cancers as well as many other types of cancers (Kohl et al., Science 1993, 260, 1834-1837). The effects of Ras on proliferation and tumorigenesis have been documented in immortal cell lines (McCubrey et al., Int J Oncol 1995, 7, 295-310). bRaf mutations have been identified in more than 60% of malignant melanoma (Davies, H et al., Nature 2002, 417, 949954). Given the high level of mutations that have been detected at Ras, this pathway has always been considered a key target for therapeutic intervention (Chang et al., Leukemia 2003, 17, 1263-93).

As constitutive or overactivation of MAP kinase cascade plays a pivotal role in cell proliferation and differentiation, inhibition of this pathway is believed is to be beneficial in hyperproliferative diseases. MEK is a key player in this pathway as it is downstream of Ras and Raf. Additionally, it is an attractive therapeutic target because the only known substrates of MEK phosphorylation are the MAP kinases, ERK1 and ERK2 Inhibition of MEK has been shown to have potential therapeutic benefit in several studies. For example, small molecule MEK inhibitors have been shown to inhibit human tumor growth in mouse xenografts, (Seebolt-Leopold et. al., Nature-Medicine, 1999 5(7), 810-816; Trachet et al. AACR Apr. 6-10, 2002, Poster & num; 5426) and inhibit growth of acute myeloid leukemia cells (Milella et. al., J. Clin. Invest., 2001, 108 (6) 851-859).

Compounds suitable as MEK inhibitors are also disclosed in WO 00/41994; WO 00/42022; WO 00/42029; WO 00/68201; WO 01/68619; WO 02/06213, WO 03/077914, WO 05/023251, WO 05/121142, WO 07/014,011, WO 07/044,084, WO 07/071,951, WO 07/121,481, WO 07/123, 939, WO 08/021389, WO 08/078,086, WO 08/120,004, WO 08/124,085, WO 09/018,233, WO 09/018,238, WO 09/013, 462, WO 09/021,887, WO 09/080,523, WO 09/082,687, WO 09/085,983, WO 09/093,008, WO 09/093,009, WO 09/093,013, WO 09/129,938, WO 09/153,554, U.S. Ser. No. 09/012,4595, U.S. Ser. No. 09/024,6198, U.S. Ser. No. 09/027,5606, WO 10/003,022, WO 10/003,025, WO 10/051,933 and WO 10/051,935.

SUMMARY OF THE INVENTION

This invention provides a compound of formula I, or a pharmaceutically acceptable salt, solvate, polymorph, ester, tautomer or prodrug thereof:

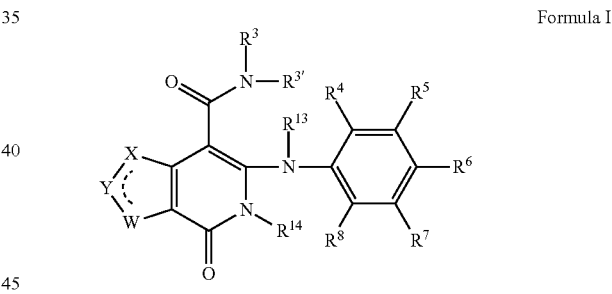

Formula I

Wherein

┄┄┄ represents X—Y=W or W—Y=X;

X and W are independently selected from N, O, S or $CR^2$;

Y is N or $CR^1$; and $R^1$ is selected from the group consisting of H, halogen, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl; wherein each H, alkyl, cycloalkyl, alkenyl, cycloalkenyl or alkynyl group is optionally substituted with 1-3 substituents selected independently from the group consisting of halogen, hydroxy, amino, alkylamino, dialkylamino, heterocyclyl, $C_1$-$C_4$ alkyl, $C_1$-$C_4$ alkoxy, $C_1$-$C_4$ alkylthiol, cyano, cyanomethyl, trifluoromethyl, difluoromethoxy and phenyl, and one or two ring carbon atoms of said $C_3$-$C_6$ cycloalkyl groups are optionally replaced with, independently, O, N, or S;

$R^2$ is selected from the group consisting of H, halogen, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_3$-$C_{10}$ cycloalkoxy, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents selected independently from halogen, hydroxyl, $C_1$-$C_4$ alkyl, $C_1$-$C_4$ alkoxy, cyano, trifluoromethyl, difluoromethoxy, phenyl or substituted phenyl with 1-3 substituents selected independently from halogen, hydroxyl, $C_1$-$C_4$ alkyl, $C_1$-$C_4$ alkoxy, cyano, trifluoromethyl, or difluoromethoxy;

$R^3$ is selected from the group consisting of H, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_3$-$C_{10}$ cycloalkoxy, $C_3$-$C_{10}$ cycloalkylalkyl, aryl, arylalkyl, heteroaryl, heteroarylalkyl, heterocyclyl, and heterocyclylalkyl, where each alkyl, alkoxy, alkenyl, alkynyl, cycloalkyl, aryl, heteroaryl and heterocyclyl is unsubstituted or substituted with 1-3 substituents selected independently from halogen, hydroxyl, $C_1$-$C_4$ alkyl, $C_1$-$C_4$ alkoxy, cyano, trifluoromethyl, difluoromethoxy, phenyl or substituted phenyl with 1-3 substituents selected independently from halogen, hydroxyl, $C_1$-$C_4$ alkyl, $C_1$-$C_4$ alkoxy, cyano, trifluoromethyl, or difluoromethoxy;

$R^{3'}$ is selected from the groups consisting of H, $C_1$-$C_6$ alkyl, $C_2$-$C_6$ alkenyl and $C_2$-$C_6$ alkynyl;

$R^4$, $R^5$, $R^6$, $R^7$ and $R^8$ are independently selected from H, halogen, cyano, nitro, trifluoromethyl $SR^9$, $OR^9$, $C(O)R^9$, $NR^{10}C(O)OR^{12}$, $OC(O)R^9$, $NR^{10}S(O)_jR^{12}$, $S(O)_jNR^9R^{10}$, $S(O)_jNR^{10}C(O)R^9$, $C(O)NR^{10}S(O)_jR^{12}$, $S(O)_jR^{12}$, $NR^{10}C(O)R^9$, $C(O)NR^9R^{10}$, $NR^{10}C(O)NR^9R^{10}$, $NR^{11}C(NCN)NR^9R^{10}$, $NR^9R^{10}$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, $S(O)_j(C_1$-$C_6$ alkyl), $S(O)_j(CR^{10}R^{11})_m$-aryl, aryl, arylalkyl, heteroaryl, heteroarylalkyl, heterocyclyl, heterocyclylalkyl, $O(C)R^9R^{10})_m$-aryl, $NR^{11}(CR^{10}R^{11})_m$-aryl, $O(CR^{10}R^{11})_m$-heteroaryl, $NR^{10}(CR^{10}R^{11})_m$-heteroaryl, $O(CR^{10}R^{11})_m$-heterocyclyl, $NR^{10}(CR^{11}R^{11})_m$-heterocyclyl, and $S(C_1$-$C_2$ alkyl) optionally substituted with 1-5 fluorine atoms;

$R^9$ is selected from the group consisting of hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents independently selected from the group consisting of halogen, $C_1$-$C_4$ alkyl, hydroxyl and amino;

$R^{10}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R^9$ and $R^{10}$ can be taken together with the atom to which they are attached to form a 4 to 10 membered heteroaryl or heterocyclic ring, each of which is unsubstituted or substituted with 1-3 substituents independently selected from the group consisting of halogen, $C_1$-$C_4$ alkyl, hydroxyl and amino;

$R^{11}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R^{10}$ and $R^{11}$ can be taken together with the atom to which they are attached to form a 4 to 10 membered carbocyclic, heteroaryl or heterocyclic ring, each of which is unsubstituted or substituted with 1-3 substituents independently selected from the group consisting of halogen, $C_1$-$C_4$ alkyl, hydroxyl and amino;

$R^{12}$ is selected from trifluoromethyl, $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl unsubstituted or substituted with 1-3 substituents independently selected from the group consisting of halogen, $C_1$-$C_4$ alkyl, hydroxyl and amino;

$R^{13}$ is selected from the groups consisting of H, $C_1$-$C_6$ alkyl, $C_2$-$C_6$ alkenyl and $C_2$-$C_6$ alkynyl;

$R^{14}$ is selected from the groups consisting of H, $C_1$-$C_6$ alkyl, $C_2$-$C_6$ alkenyl and $C_2$-$C_6$ alkynyl;

m is 0, 1, 2, 3, 4, or 5; and j is 1 or 2.

In another aspect, the present invention provides some preferable compounds of Formula I, wherein one of X and W is O or S; or a pharmaceutically acceptable salt, solvate, polymorph, ester, tautomer or prodrug thereof. Preferably, one of X and W is O or S, and the other is $CR^2$.

In another aspect, the present invention provides some preferable compounds having the following Formula,

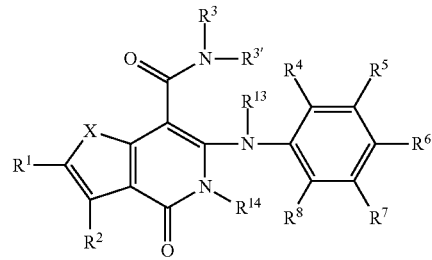

Formula II wherein

X is O or S; and $R^1$, $R^2$, $R^3$, $R^{3'}$, $R^4$, $R^5$, $R^6$, $R^7$, $R^8$, $R^9$, $R^{10}$, $R^{11}$, $R^{12}$, $R^{13}$ and $R^{14}$ are defined as above.

In another aspect, the present invention provides some preferable compounds of Formula I, wherein Y is $CR^1$ and $R^1$ is H, halogen, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl; wherein each alkyl, cycloalkyl, alkenyl, cycloalkenyl or alkynyl group is optionally substituted with 1-3 substituents selected independently from the group consisting of halogen, hydroxy, amino, alkylamino, dialkylamino, heterocyclyl, $C_1$-$C_4$ alkyl, $C_1$-$C_4$ alkoxy, cyano, cyanomethyl, trifluoromethyl, difluoromethoxy and phenyl, and one or two ring carbon atoms of said $C_3$-$C_6$ cycloalkyl groups are optionally replaced with, independently, O, N, or S; or a pharmaceutically acceptable salt, solvate, polymorph, ester, tautomer or prodrug thereof.

In another aspect, the present invention provides some preferable compounds of Formula I, wherein one of X and W is $CR^2$ and $R^2$ is selected from the group consisting of H, halogen, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_3$-$C_{10}$ cycloalkoxy, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents selected independently from halogen, hydroxyl, $C_1$-$C_4$ alkyl, $C_1$-$C_4$ alkoxy, cyano trifluoromethyl, difluoromethoxy, phenyl or substituted phenyl with 1-3 substituents selected independently from halogen, hydroxyl, $C_1$-$C_4$ alkyl, $C_1$-$C_4$ alkoxy, cyano trifluoromethyl, or difluoromethoxy; or a pharmaceutically acceptable salt, solvate, polymorph, ester, tautomer or prodrug thereof.

In another aspect, the present invention provides some preferable compounds of Formula I, wherein $R^3$ is selected from the group consisting of hydrogen, $C_1$-$C_6$ alkyl optionally substituted with one or more substituents selected from the group consisting of halogen, hydroxyl and alkoxy; $C_1$-$C_6$ alkoxyl optionally substituted with one or more substituents selected from the group consisting of halogen, hydroxyl and cycloalkyl; $C_2$-$C_6$ alkenyl; $C_3$-$C_6$ cycloalkyl optionally substituted with $C_1$-$C_6$ alkyl or $C_2$-$C_6$ alkenyl; 5 or 6 membered monocyclic or 9 to 13 membered bicyclic heteroaryl with O, N, or S as the hetero atom; 5 or 6 membered monocyclic or 9 to 13 membered bicyclic aryl optionally substituted with one or more substituents selected from the group consisting of halogen, cyano, $C_1$-$C_6$ alkoxy and hydroxyl; arylcycloalkyl in which aryl is monocyclic or bicyclic aryl and cycloalkyl has 1 to 6 carbon atoms; and $C_1$-$C_6$ alkyl $C_1$-$C_6$ cycloalkyl; or a pharmaceutically acceptable salt, solvate, polymorph, ester, tautomer or prodrug thereof. Preferably, $R^3$ is selected from the group consisting of $C_1$-$C_6$ alkyl and $C_1$-$C_6$ alkoxy, where alkyl and alkoxy are independently unsubstituted or substituted with one or more substituents selected independently from the group consisting of halogen and hydroxyl.

In another aspect, the present invention provides some preferable compounds of Formula I, wherein $R^{3'}$ is selected from the groups consisting of H and $C_1$-$C_6$ alkyl; or a pharmaceutically acceptable salt, solvate, poly-morph, ester, tautomer or prodrug thereof.

In another aspect, the present invention provides some preferable compounds of Formula I, wherein $R^4$, $R^5$, $R^6$, $R^7$ and $R^8$ are independently selected from the group consisting of H and halogen; or a pharmaceutically acceptable salt, solvate, polymorph, ester, tautomer or prodrug thereof.

In another aspect, the present invention provides some preferable compounds of Formula I, wherein one of $R^4$ and $R^8$ is fluoro or chloro, and $R^6$ is iodo; or a pharmaceutically acceptable salt, solvate, polymorph, ester, tautomer or prodrug thereof.

In another aspect, the present invention provides some preferable compounds of Formula I, wherein $R^{13}$ is selected from the groups consisting of H and $C_1$-$C_6$ alkyl; or a pharmaceutically acceptable salt, solvate, poly-morph, ester, tautomer or prodrug thereof.

In another aspect, the present invention provides some preferable compounds of Formula I, wherein $R^{14}$ is selected from $C_1$-$C_6$ alkyl; or a pharmaceutically acceptable salt, solvate, poly-morph, ester, tautomer or prodrug thereof.

In other embodiments, the present invention provides compounds represented by the following formula

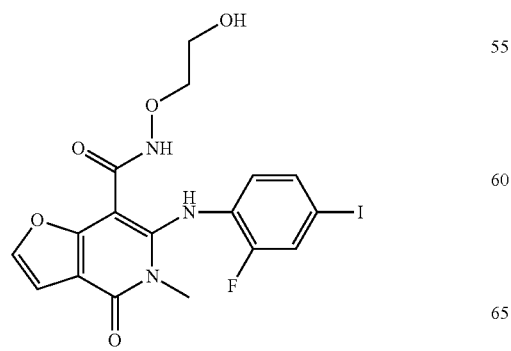

-continued

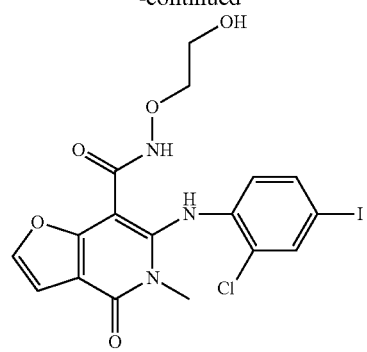

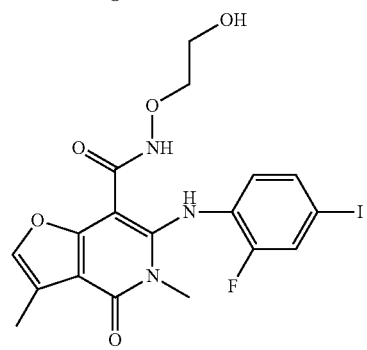

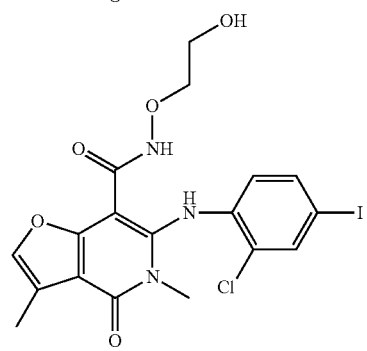

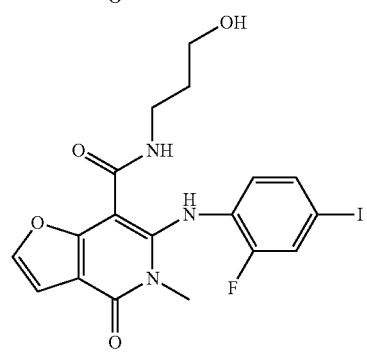

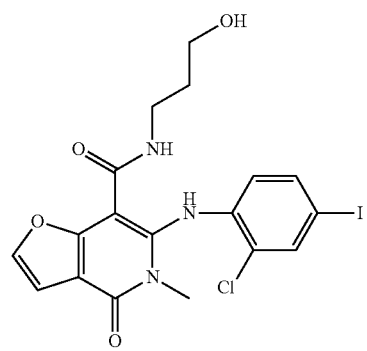

-continued
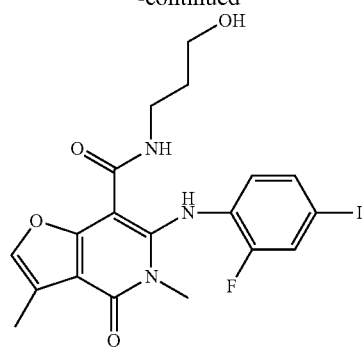
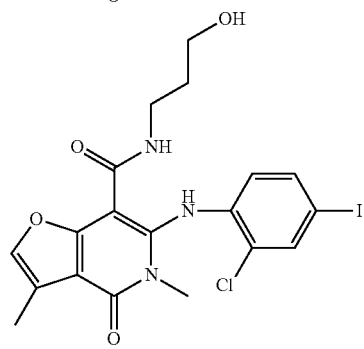
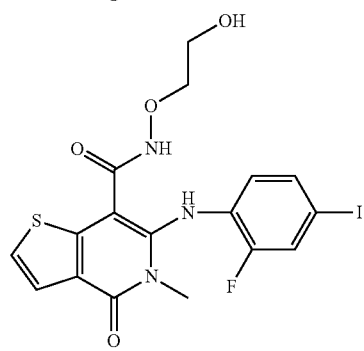
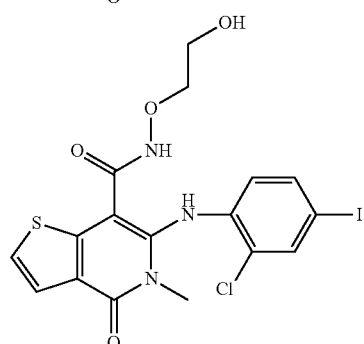
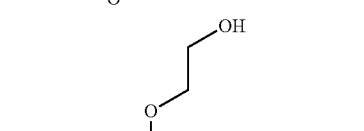
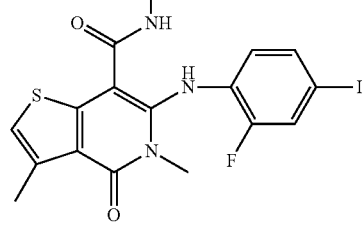
-continued
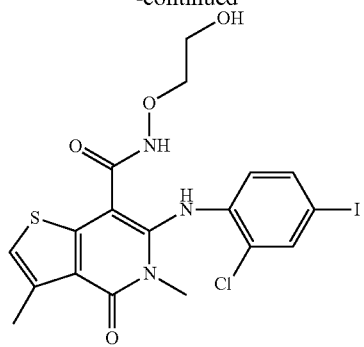
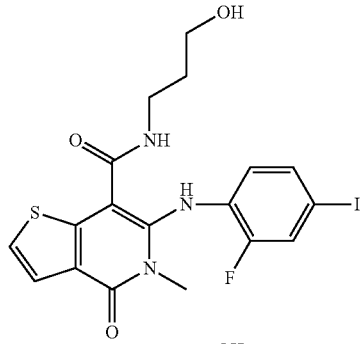
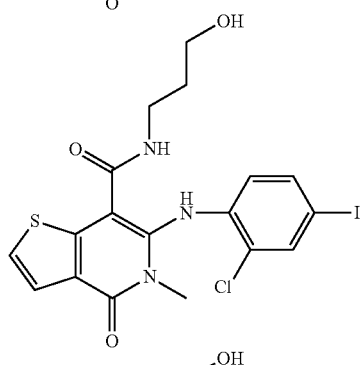
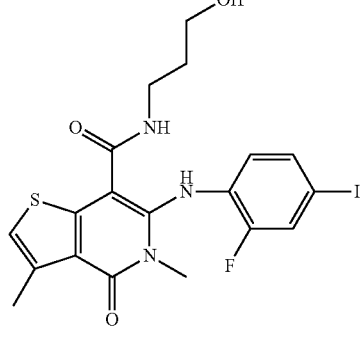
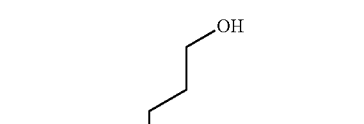
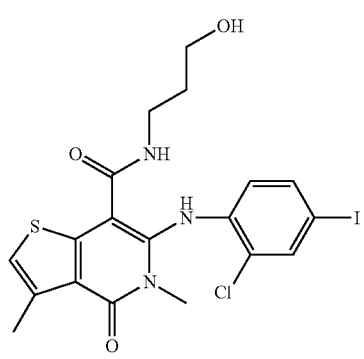 [SMILES: Cc1csc2c(C(=O)NCCCO)c(Nc3ccc(I)cc3Cl)n(C)c(=O)c12]

or a pharmaceutically acceptable salt, solvate, poly-morph, ester, tautomer or prodrug thereof.

Compounds of present invention are inhibitors of MEK and, consequently, are useful for treating cancer and other hyperproliferative diseases.

In other aspects, the present invention is directed to a pharmaceutical composition comprising an effective amount of a compound of formula I or a pharmaceutically acceptable salt, solvate, polymorph, ester, tautomer or prodrug thereof. In some embodiments, the pharmaceutical composition further comprises a pharmaceutically acceptable carrier. Such a composition may contain at least one of adjuvants, excipients, and preservatives, agents for delaying absorption, fillers, binders, adsorbents, buffers, disintegrating agents, solubilizing agents, other carriers, and other inert ingredients. Methods of formulating the composition are well-known in the art.

In some aspects, the present invention is directed to a method of treating a disease in an individual suffering from said disease comprising administering to said individual a therapeutically effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of a compound of formula I or a pharmaceutically acceptable salt, solvate, polymorph, ester, tautomer or prodrug thereof.

In other aspects, the present invention is directed to a method of treating a disorder in a human, comprising administering to said human a therapeutically effective amount of a compound of formula I or a pharmaceutically acceptable salt, solvate, polymorph, ester, tautomer or prodrug thereof.

In other aspects, the present invention is directed to a method of treating an inflammatory disease, condition, or disorder in a mammal, including a human, comprising administering to said mammal a therapeutically effective amount of a compound of formula I, or a pharmaceutically acceptable salt, ester, prodrug, solvate, such as hydrate, polymorph or tautomer thereof.

In other aspects, the present invention is directed to a method of treating a disorder or condition which is modulated by the MEK cascade in a mammal, including a human, comprising administering to said mammal an amount of the compound of formula I, or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compound of formula I or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the MEK cascade in a mammal, including a human. The pharmaceutical composition is useful for treating cancer, inflammatory disease and other hyperproliferative diseases.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineopiastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of formula I.

In other aspects, the present invention is directed to a method for inhibiting a MEK enzyme. The method comprises contacting said MEK enzyme with an amount of a composition comprising a compound of formula I or a pharmaceutically acceptable salt, solvate, polymorph, ester, tautomer or prodrug thereof, sufficient to inhibit said enzyme, wherein said enzyme is inhibited. In some embodiments, the present invention is directed to a method for selectively inhibiting a MEK enzyme.

In other aspects, the present invention is directed to use of a compound of formula I or a pharmaceutically acceptable salt, solvate, polymorph, ester, tautomer or prodrug thereof in the preparation of a pharmaceutical composition for inhibiting a MEK enzyme.

In further or additional embodiments, the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In some embodiments, the compounds of this invention can selectively inhibit a MEK1 enzyme or MEK2 enzyme. In some other embodiments, the compounds of this invention may not have the selectivity between a MEK1 enzyme and MEK2 enzyme. In further or additional embodiments the contacting occurs within a cell. In further or additional embodiments the cell is a mammalian cell. In further or additional embodiments the mammalian cell is a human cell. In further or additional embodiments, the MEK enzyme is inhibited with a composition comprising a pharmaceutically acceptable salt of a compound of formula I.

In other aspects, the present invention is directed to a method of treatment of a MEK mediated disorder in an individual suffering from said disorder comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for treating a MEK mediated disorder.

In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the MEK mediated disorder is a mammal. In further or additional embodiments, the individual is a human. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the MEK mediated disorder is selected from the group consisting of inflammatory diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the MEK mediated disorder is an inflammatory disease. In further or additional embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for degrading and/or inhibiting the growth of or killing a cancer cell.

In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I is used.

In other aspects, the present invention is directed to a method for the treatment or prophylaxis of a proliferative disease in an individual comprising administering to said individual an effective amount of a composition comprising a compound of formula I or a pharmaceutically acceptable salt, solvate, polymorph, ester, tautomer or pro-drug thereof.

In other aspects, the present invention is directed to use of a compound of formula I or a pharmaceutically acceptable salt, solvate, polymorph, ester, tautomer or prodrug thereof in the preparation of a pharmaceutical composition for the treatment or prophylaxis of a proliferative disease.

In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of an inflammatory disease in an individual comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for the treatment or prophylaxis of an inflammatory disease.

In further or additional embodiments, the inflammatory disease is selected from chronic inflammatory diseases, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of formula is administered in combination with an additional therapy. In further or additional embodiments, the composition comprising a compound of formula is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of cancer in an individual comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for the treatment or prophylaxis of a cancer.

In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for reducing the size of a tumor, inhibiting tumor size increase, reducing tumor proliferation or preventing tumor proliferation.

In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, antimetabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method for achieving an effect in a patient comprising the administration of an effective amount of a composition comprising a compound of formula I or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases.

In other aspects, the present invention is directed to use of a compound of formula I or a pharmaceutically acceptable salt, solvate, polymorph, ester, tautomer or prodrug thereof in the preparation of a pharmaceutical composition for the inhibiting various cancers, immunological diseases, and/or inflammatory diseases.

In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a process for preparing a compound of formula I or a pharmaceutically acceptable salt, solvate, polymorph, ester, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-Cn, includes $C_1$-$C_2$, $C_1$-$C_3$ ... $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene ($—CH_2$), ethylene ($—CH_2CH_2$), propylene ($—CH_2CH_2CH_2$), isopropylene ($—CH(CH_3)CH_2$) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl ($CH—CH_2$), 1-propenyl ($CH_2CH=CH_2$), isopropenyl [$C(CH_3)=CH_2$], butenyl, 1,3-butadienyl and the like. Whenever it appears herein, a numerical range such as "$C_2$-$C_6$ alkenyl" or "$C_{2\text{-}6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (CH—CH), the propenylene isomers (e.g., $CH_2CH=CH$ and $C(CH_3)=CH$) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2\text{-}6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—CC—), propargylene (—$CH_2$CC—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo, chloro, fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "aromatic" as used herein, refers to a planar, cyclic or polycyclic, ring moiety having a delocalized $\pi$-electron system containing $4n+2\pi$ electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heteroarylene" as used herein, alone or in combination, refers to a diradical derived from the above-defined monoradical heteroaryl. Examples include, but are not limited to pyridinylene and pyrimidinylene.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

A non-limiting example of "heterocyclyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "carbocyclyl" as used herein, alone or in combination, refers collectively to alicyclyl and aryl groups; i.e. all carbon, covalently closed ring structures, which may be saturated (i.e., cycloalkyl), partially unsaturated (cycloalkenyl), fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

The terms "halogen", "halo" or "halide" as used herein, alone or in combination refer to fluoro, chloro, bromo and iodo.

The term "alkoxy" as used herein, alone or in combination, refers to an alkyl ether radical, O-alkyl, including the groups O-aliphatic and O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tertbutoxy and the like.

The term "alkylthiol" as used herein, alone or in combination, refers to an alkyl sufide radical, —S-alkyl, including —S-aliphatic and —S-carbocyclyl, wherein the alkyl, aliphatic and carbocyclyl groups may be optionally substituted, and wherein the terms alkyl, aliphatic and carbocyclyl are as defined herein. Preferably, the alkyl has 1 to about 6, 1 to about 4 carbon atoms. Non-limiting examples of alkylthiol radicals include methylthiol, ethylthiol, and the like.

The term "sulfinyl" as used herein, alone or in combination, refers to the diradical —S(=O).

The term "sulfonyl" as used herein, alone or in combination, refers to the diradical —S(=O)$_2$.

The terms "sulfonamide", "sulfonamido" and "sulfonamidyl" as used herein, alone or in combination, refer to the diradical groups —S(=O)$_2$—NH— and —NH—S(=O)$_2$.

The terms "carboxamide" and "carboxamido" as used herein, alone or in combination, refer to the group of

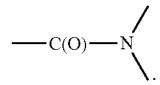

Certain Pharmaceutical Terminology

The term "MEK inhibitor" as used herein refers to a compound that exhibits an $IC_{50}$, with respect to MEK activity, of no more than about 100 M or not more than about 50 M, as measured in the Mek1 kinase assay described generally herein. "$IC_{50}$" is that concentration of inhibitor which reduces the activity of an enzyme (e.g., MEK) to half-maximal level. Compounds described herein have been discovered to exhibit inhibition against MEK. Compounds of the present invention preferably exhibit an $IC_{50}$ with respect to MEK of no more than about 10 M, more preferably, no more than about 5 M, even more preferably not more than about 1 M, and most preferably, not more than about 200 nM, as measured in the Meld kinase assay described herein.

The term "selective," "selectively," or "selectivity" as used herein refers to a compound of this invention having a lower $IC_{50}$ value for a MEK enzyme as compared to any other enzymes (e.g., at least 2, 5, 10 or more-fold lower). The term may also refer to a compound of this invention having a lower $IC_{50}$ value for a MEK1 enzyme as compared to a MEK2 enzyme (e.g., at least 2, 5, 10 or more-fold) or alternatively having a lower $IC_{50}$ value for a MEK2 enzyme as compared to a MEK1 enzyme (e.g., at least 2, 5, 10 or more-fold lower).

The term "subject", "patient" or "individual" as used herein in reference to individuals suffering from a disorder, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal mutes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed.

Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecyl sulfate, ethanesulfonate, formate, fumarate, glucoheptanoate, glycerophosphate, glycolate, hemisulfate, heptanoate, hexanoate, hexyne-1,6-dioate, hydroxybenzoate, y-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, IV' $(C_{1-4}$ alkyl$)_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Compounds

Described herein are compounds of formula I, pharmaceutically acceptable salts, solvates, polymorphs, esters, tautomers or prodrugs thereof,

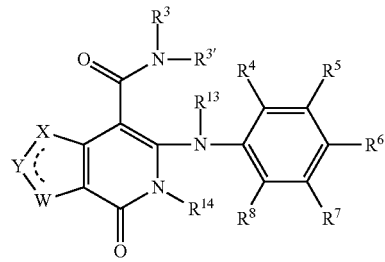

Formula I wherein

⋯⋯ represents X—Y=W or W—Y=X;

X and W are independently selected from N, O, S or $CR^2$;

Y is N or $CR^1$; and $R^1$ is selected from the group consisting of H, halogen, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl; wherein each alkyl, cycloalkyl, alkenyl, cycloalkenyl or alkynyl group is optionally substituted with 1-3 substituents selected independently from the group consisting of halogen, hydroxy, amino, alkylamino, dialkylamino, heterocyclyl, $C_1$-$C_4$ alkyl, $C_1$-$C_4$ alkoxy, cyano, cyanomethyl, trifluoromethyl, difluoromethoxy and phenyl, and one or two ring carbon atoms of said $C_3$-$C_6$ cycloalkyl groups are optionally replaced with, independently, O, N, or S; and $R^2$ is selected from the group consisting of H, halogen, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_3$-$C_{10}$ cycloalkoxy, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents selected independently from halogen, hydroxyl, $C_1$-$C_4$ alkyl, $C_1$-$C_4$ alkoxy, cyano trifluoromethyl, difluoromethoxy, phenyl or substituted phenyl with 1-3 substituents selected independently from halogen, hydroxyl, $C_1$-$C_4$ alkyl, $C_1$-$C_4$ alkoxy, cyano trifluoromethyl, or difluoromethoxy;

$R^3$ is selected from the group consisting of H, $C_1$-$C_{10}$ alkyl, $C_1$-$C_{10}$ alkoxy, $C_2$-$C_{10}$ alkenyl, $C_2$-$C_{10}$ alkynyl, $C_3$-$C_{10}$ cycloalkyl, $C_3$-$C_{10}$ cycloalkoxy, $C_3$-$C_{10}$ cycloalkylalkyl, aryl, arylalkyl, heteroaryl, heteroarylalkyl, heterocyclyl, and heterocyclylalkyl, where each alkyl, alkoxy, alkenyl, alkynyl, cycloalkyl, aryl, heteroaryl and heterocyclyl is unsubstituted or substituted with 1-3 substituents selected independently from halogen, hydroxyl, $C_1$-$C_4$ alkyl, $C_1$-$C_4$ alkoxy, cyano trifluoromethyl, difluoromethoxy, phenyl or substituted phenyl with 1-3 substituents selected independently from halogen, hydroxyl, $C_1$-$C_4$ alkyl, $C_1$-$C_4$ alkoxy, cyano trifluoromethyl, or difluoromethoxy;

$R^{3'}$ is selected from the groups consisting of H, $C_1$-$C_6$ alkyl, $C_2$-$C_6$ alkenyl and $C_2$-$C_6$ alkynyl;

$R^4$, $R^5$, $R^6$, $R^7$ and $R^8$ are independently selected from H, halogen, cyano, nitro, trifluoromethyl $SR^9$, $OR^9$, $C(O)R^9$, $NR^{10}C(O)OR^{12}$, $OC(O)R^9$, $NR^{10}S(O)_jR^{12}$, $S(O)_jNR^9R^{10}$, $S(O)_jNR^{10}C(O)R^9$, $C(O)NR^{10}S(O)_jR^{12}$, $S(O)_jR^{12}$, $NR^{10}(O)R^9$, $C(O)NR^9R^{10}$, $NR^{10}C(O)NR^9R^{10}$, $NR^{11}C(NCN)NR^9R^{10}$, $NR^9R^{10}$ and $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, $S(O)_j(C_1$-$C_6$ alkyl), $S(O)_j(CR^{10}R^{11})_m$-aryl, aryl, arylalkyl, heteroaryl, heteroarylalkyl, heterocyclyl, heterocyclylalkyl, $O(CR^9R^{10})_m$-aryl, $N_{R11}(CR^{10}R^{11})_m$-aryl, $O(CR^{10}R^{11})_m$-heteroaryl, $NR^{10}(CR^{10}R^{11})_m$-heteroaryl, $O(CR^{10}R^{11})_m$-heterocyclyl, $NR^{10}(CR^{11}R^{11})_m$-heterocyclyl, and $S(C_1$-$C_2$ alkyl) optionally substituted with 1-5 fluorine atoms;

$R^9$ is selected from the group consisting of hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents independently selected from the group consisting of halogen, $C_1$-$C_4$ alkyl, hydroxyl and amino;

$R^{10}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R^9$ and $R^{10}$ can be taken together with the atom to which they are attached to form a 4 to 10 membered heteroaryl or heterocyclic ring, each of which is unsubstituted or substituted with 1-3 substituents independently selected from the group consisting of halogen, $C_1$-$C_4$ alkyl, hydroxyl and amino;

$R^{11}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R^{10}$ and $R^{11}$ can be taken together with the atom to which they are attached to form a 4 to 10 membered carbocyclic, heteroaryl or heterocyclic ring, each of which is unsubstituted or substituted with 1-3 substituents independently selected from the group consisting of halogen, $C_1$-$C_4$ alkyl, hydroxyl and amino;

$R^{12}$ is selected from trifluoromethyl, $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl unsubstituted or substituted with 1-3 substituents independently selected from the group consisting of halogen, $C_1$-$C_4$ alkyl, hydroxyl and amino;

$R^{13}$ is selected from the groups consisting of H, $C_1$-$C_6$ alkyl, $C_2$-$C_6$ alkenyl and $C_2$-$C_6$ alkynyl;

$R^{14}$ is selected from the groups consisting of H, $C_1$-$C_6$ alkyl, $C_2$-$C_6$ alkenyl and $C_2$-$C_6$ alkynyl;

m is 0, 1, 2, 3, 4, or 5; and j is 1 or 2.

Methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein.

SYNTHETIC PROCEDURES AND EXAMPLES

The compounds of formula I wherein $R^{3'}$ is hydrogen, $R^{13}$ is hydrogen, and $R^{14}$ is methyl shown as the following formula is taken as an example to illustrate the preparation of the compounds of formula I.

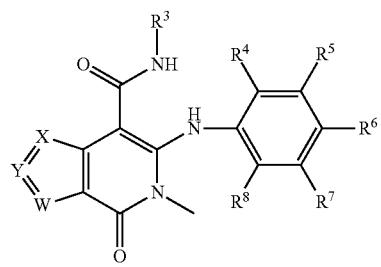

treatment with carbodiimide (2) afforded pyridone ester (3). Coupling the amines (5) by treatment the pyridone ester (3) with LiHMDS or by coupled with pyridone acid (4) after hydrolysis from pyridone ester (3), gave desired pyridone amides (6).

Typical Procedure A for Synthesis of Carbodiimides

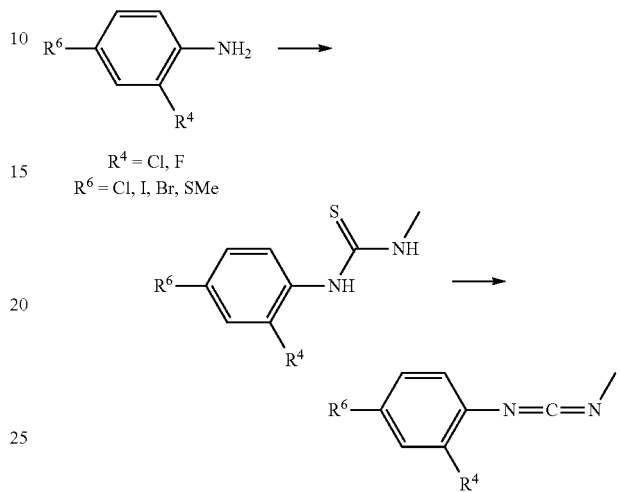

Procedure A: To the solution of aniline (5 g, 1 eq.) in 50 mL EtOH was added methylisothiocyanate (1.4 eq.) at room temperature, the mixture was then heated under reflux Scheme 1

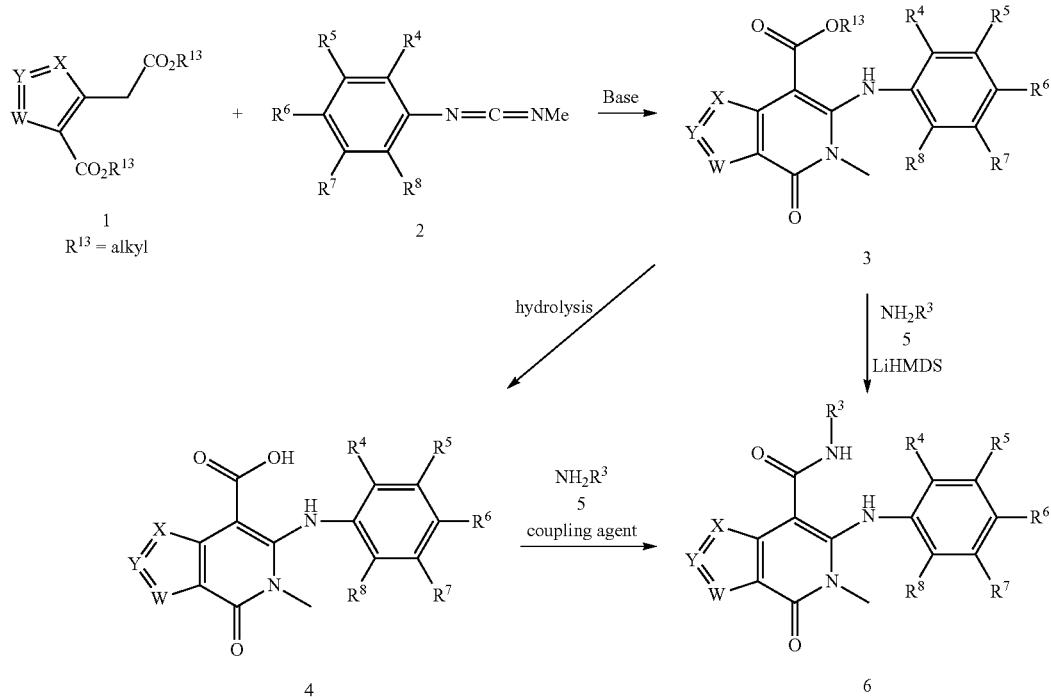

Scheme 1 above illustrates the preparation of 5-membered ring[b] pyridone amide of (6). Deporton of 5-membered ring di-ester (1) with base as NaH, LiHMDS, etc. followed by overnight. After cooling down, the precipitate was collected and washed with 50 mL petroleum ether/dichloromethane (10/1) to afford the thiourea.

To a solution of 10 mmol of the thiourea, 3.0 g (30 mmol) of triethylamine, and 50 mg of 4-dimethylamino-pyridine (DMAP) in 100 mL of methylene chloride is added dropwise 2.3 g (20 mmol) of methanesulfonyl chloride (on a larger scale some cooling may be required to keep the reaction near room temperature). After addition is complete, the resulting yellow solution is stirred at room temperature for 5 minutes. Approximately two-thirds of the solvent is removed under reduced pressure and the remaining mixture is filtered through a pad of silica gel using methylene chloride to elute the product. A second pad filtration is needed to remove any final traces of polar material to afford the cabodiimide (ref.: *Syn. Commun.*, 1995, 25, 43-47.)

2-fluoro-4-iodo-N-((methylimino)methylene)aniline

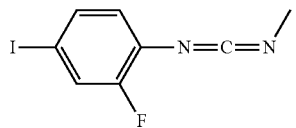

Thiourea: $^1$H NMR (400 MHz, DMSO-D6) δ 9.30 (s, 1H), 7.86 (s, 1H), 7.67 (dd, J =2.0 & 10.0 Hz, 1H), 7.52 (dd, J=2.0 & 8.4 Hz, 1H), 7.44 (t, J=8.4 Hz, 1H), 2.89 (d, J=4.0 Hz, 3H); carbodiimide: $^1$H NMR (400 MHz, CDCl$_3$) δ 7.40 (dd, J=2.0 & 10.0 Hz, 1H), 7.35 (dd, J=2.0 & 8.4 Hz, 1H), 6.79 (t, J=8.4 Hz, 1H), 3.18 (s, 3H).

4-bromo-2-fluoro-N-((methylimino)methylene)aniline

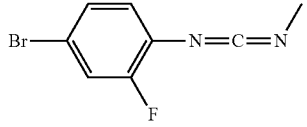

Thiourea: $^1$H NMR (400 MHz, DMSO-D6) δ 9.23 (s, 1H), 7.88 (s, 1H), 7.62-7.66 (m, 2H), 7.40 (t, J=8.8 Hz, 1H), 2.91 (d, J=4.4 Hz, 3H); carbodiimide: $^1$H NMR (400 MHz, CDCl$_3$) δ 7.24 (dd, J=2.0 & 10.0 Hz, 1H), 7.17 (dd, J=2.0 & 8.4 Hz, 1H), 6.93 (t, J=8.4 Hz, 1H), 3.17 (s, 3H).

4-bromo-2-chloro-N-((methylimino)methylene)aniline

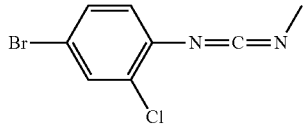

Thiourea: $^1$H NMR (400 MHz, DMSO-D6) δ 9.22 (s, 1H), 7.90 (s, 1H), 7.76 (s, 1H), 7.57-7.59 (m, 1H), 7.50-7.53 (m, 1H), 2.90 (d, J=4.4 Hz, 3H); carbodiimide: $^1$H NMR (400 MHz, CDCl$_3$) δ 7.47 (d, J=2.0 Hz, 1H), 7.25 (dd, J=2.0 & 8.8 Hz, 1H), 6.95 (d, J=8.8 Hz, 1H), 3.16 (s, 3H).

2-chloro-4-iodo-N-((methylimino)methylene)aniline

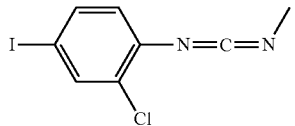

Thiourea: $^1$H NMR (400 MHz, CDCl$_3$) δ 7.83 (d, J=1.6 Hz, 1H), 7.64 (dd, J=1.6 & 8.4 Hz, 1H), 7.50 (s, 1H), 7.27 (s, br, 1H), 6.04 (s, 1H), 3.15 (d, J=4.8 Hz, 3H); carbodiimide: $^1$H NMR (400 MHz, CDCl$_3$) δ 7.67 (d, J=2.0 Hz, 1H), 7.46 (dd, J=2.0 & 8.4 Hz, 1H), 6.84 (d, J=8.4 Hz, 1H), 3.18 (s, 3H).

2,4-dichloro-N-((methylimino)methylene)aniline

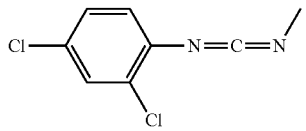

Thiourea: $^1$H NMR (400 MHz, DMSO-D6) δ 9.22 (s, 1H), 7.11 (s, 1H), 7.63-7.67 (m, 2H), 7.39 (dd, J=2.4 & 8.8 Hz, 1H), 2.92 (d, J=4.4 Hz, 3H); carbodiimide: $^1$H NMR (400 MHz, CDCl$_3$) δ 7.37 (d, J=2.0 Hz, 1H), 7.15 (dd, J=2.0 & 8.4 Hz, 1H), 7.04 (d, J=8.4 Hz, 1H), 3.18 (s, 3H).

2-fluoro-N-((methylimino)methylene)-4-(methylthio)aniline

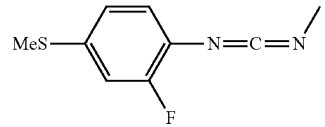

Thiourea: $^1$H NMR (400 MHz, CDCl$_3$) δ 7.52 (s, 1H), 7.27 (s, br, 1H), 7.04 (d, J=8.8 Hz, 2H), 5.98 (s, br, 1H), 3.14 (d, J=4.4 Hz, 3H), 2.49 (s, 3H); carbodiimide: $^1$H NMR (400 MHz, CDCl$_3$) δ 6.91-6.99 (m, 3H), 3.16 (s, 3H), 2.46 (s, 3H).

2-chloro-N-((methylimino)methylene)-4-(methylthio)aniline

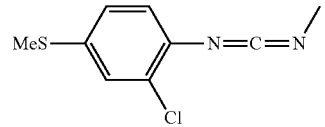

Thiourea: $^1$H NMR (400 MHz, CDCl$_3$) δ 7.53 (s, 1H), 7.30-7.33 (m, 2H), 7.17 (dd, J=2.4 & 8.4 Hz, 1H), 5.94 (s, br, 1H), 3.14 (d, J=4.8 Hz, 3H), 2.50 (s, 3H); carbodiimide: $^1$H NMR (400 MHz, CDCl$_3$) δ 7.24 (d, J=2.4 Hz, 1H), 7.01-7.08 (m, 2H), 3.16 (s, 3H), 2.46 (s, 3H).

Typical Procedure B for Synthesis of Pyridone

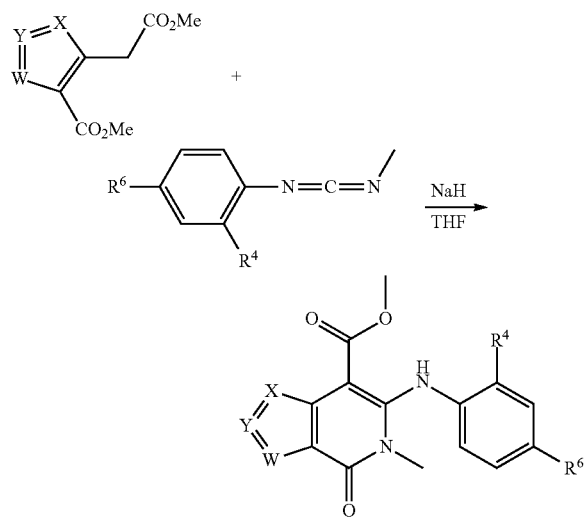

Procedure B: To a stirred solution of diester (1.0 eq.) in anhydrous THF was added NaH (1.1 eq., 60%) portionwise at 0° C. Then carbodiimide (1.4 eq., prepared from procedure A) was added slowly with dropping funnel within 1 h, the mixture was then stirred at room temperature overnight. After the addition of water and ethyl acetate, the freshly formed white precipitate was collected and washed with ethyl acetate, dried with infrared lamp to get the desired product. In some cases, the product did not precipitate, then it need purification by column chromatography.

Typical Procedure C for Coupling with Side-Chain

Procedure C: To a stirred solution of the acid (1.0 eq.), HOBt (1.5 eq.) and EDCI (1.5 eq.) in dry DMF, was added hydroxylamine (1.1 eq.) and Et$_3$N (1.5 eq.). The mixture was then stirred at room temperature overnight. Then water was added, extracted with ethyl acetate, dried (MgSO$_4$) and concentrated in vacuum, the residue was purified by column chromatography on silica gel to get the desired product.

Example 1

6-(2-Fluoro-4-iodophenylamino)-N-(2-hydroxyethoxy)-5-methyl-4-oxo-4,5-dihydrofuro[3,2-c]pyridine-7-carboxamide

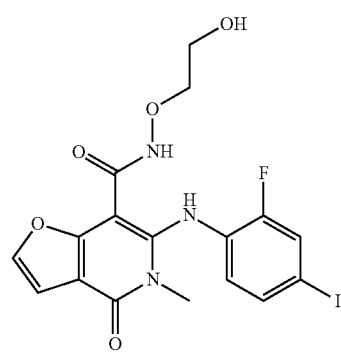

Step A: methyl 2-(2-methoxy-2-oxoethyl)furan-3-carboxylate

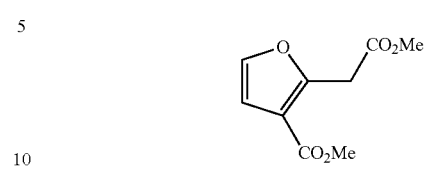

To a stirred solution of the dimethyl 3-oxopentanedioate (50 g, 287 mmol) in anhydrous pyridine (100 ml), was added the 2-chloroacetaldehyde (67.6 g, 345 mmol, 1.2 eq., 40%) under the ice-bath. The mixture was stirred under 50° C. overnight. After removing the pyridine the under reduced pressure, ethyl acetate was added, and the organic phase was washed with water, dried (Na$_2$SO$_4$) and concentrated under the reduced pressure. The residue was purified by flash column chromatography on silica gel to get the desired product (yield=61%). $^1$H NMR (400 MHz, CDCl$_3$) 7.34 (d, J=2.0 Hz, 1H), 6.70 (d, J=2.0 Hz, 1H), 4.09 (s, 2H), 3.83 (s, 3H), 3.73 (s, 3H).

Step B: methyl 6-(2-fluoro-4-iodophenylamino)-5-methyl-4-oxo-4,5-dihydrofuro[3,2-c]pyridine-7-carboxylate

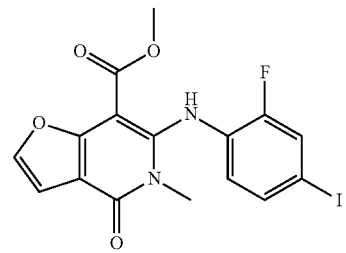

According to the procedure B: To a stirred solution of furan diester (4.8 g, 1.0 eq.) in anhydrous THF (50 ml) was added NaH (1.1 g, 1.1 eq., 60%) portionwise at 0° C. Then 2-fluoro-4-iodo-N-((methylimino)methylene aniline (7.35 g, 1.1 eq., prepared from procedure A) was added slowly with dropping funnel within 1 h and the mixture was then stirred at room temperature overnight. After the addition of water and ethyl acetate, the freshly formed white precipitate was collected and washed with ethyl acetate, dried with infrared lamp to get the desired product (yield=59%). $^1$H NMR (400 MHz, DMSO-D6) δ 9.16 (s, 1H), 7.91 (d, J=2.0 Hz, 1H), 7.65-7.68 (dd, J=1.8 & 10.6 Hz, 1H), 7.37-7.39 (dd, J=1.0 & 8.2 Hz, 1H), 6.98-6.99 (d, J=2.0 Hz, 1H), 6.64-6.68 (t, J=8.8 Hz, 1H), 3.69 (s, 3H), 3.30 (s, 3H).

Step C: 6-(2-fluoro-4-iodophenylamino)-5-methyl-4-oxo-4,5-dihydrofuro[3,2-c]pyridine-7-carboxylic acid

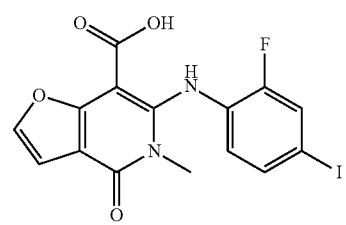

To a stirred solution (THF:MeOH:H₂O=1:1:1) of the methyl ester, was added K₂CO₃ (1.2 eq.), the reaction mixture was then stirred at 50° C. for 3 h. Then water was added and the mixture was washed with ethyl acetate twice, water layer separated, acidified with 2 N HCl, the freshly formed white precipitate was collected, washed with water, dried over infrared lamp to get the desired product (62%). ¹H NMR (400 MHz, DMSO-D6) δ 7.82 (d, J=2.0 Hz, 1H), 7.65 (dd, J=2.0 & 10.8 Hz, 1H), 7.38 (d, J=8.4 Hz, 1H), 6.90 (d, J=2.0 Hz, 1H), 6.57 (t, J=8.4 Hz, 1H), 3.20 (s, 3H).

Step D: 6-(2-fluoro-4-iodophenylamino)-N-(2-hydroxyethoxy)-5-methyl-4-oxo-4,5-dihydrofuro[3,2-c]pyridine-7-carboxamide

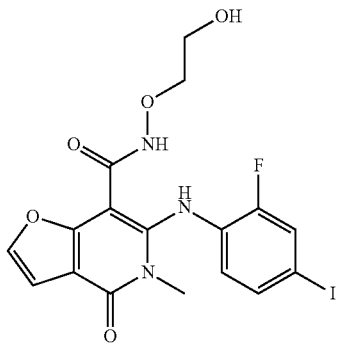

To a stirred solution of the acid (4 g, 1.0 eq.), HOBt (1.9 g, 1.5 eq.) and EDCI (2.7 g, 1.5 eq.) in dry DMF (25 mL), was added O-(2-(vinyloxy)ethyl)hydroxylamine (1.1 g, 1.1 eq.) and Et₃N (1.4 g, 1.5 eq., 2.2 mL). The mixture was then stirred at room temperature overnight. Then added with water, extracted with ethyl acetate, dried (MgSO₄) and concentrated in vacuum. The residue was then dissolved in MeOH (50 mL) and 2N HCl (10 mL) was added at room temperature. After stirring at r.t. for 0.5 h, the mixture was concentrated in vacuum, then water and ethyl acetate was added, water layer was extracted with EtOAc, washed with water, dried over MgSO₄ and concentrated under reduced pressure. The residue was purified by flash column chromatography on silica gel to obtain the desired product (53%). ¹H NMR (400 MHz, CDCl₃) δ 10.82 (s, 1H), 9.84 (s, 1H), 7.58-7.48 (m, 2H), 7.47-7.28 (m, 1H), 7.02 (s, 1H), 6.56 (t, J=8.8 Hz, 1H), 4.12-4.06 (m, 3H), 3.79-3.76 (m, 2H), 3.31 (s, 3H); m/z=411 [M-NHOCH₂CH₂OH]⁺, 488 [M+1]⁺.

Example 2

6-(2-Fluoro-4-iodophenylamino)-N-(2-hydroxyethoxy)-2,5-dimethyl-4-oxo-4,5-dihydrofuro[3,2-c]pyridine-7-carboxamide

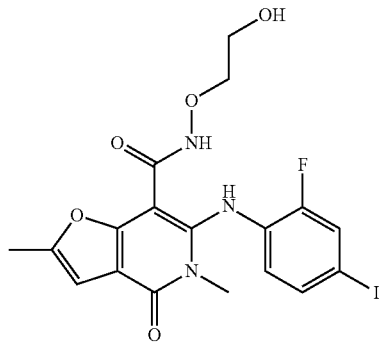 [SMILES: Cc1cc2c(=O)n(C)c(Nc3ccc(I)cc3F)c(C(=O)NOCCO)c2o1]

Step A: 2-chloropropanal

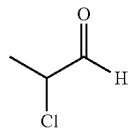

(D,L)-Proline (1.9 g, 17 mmol) was added to a stirred ice-cooled solution of propionaldehyde (5.0 g, 86 mmol) in 50 mL CHCl₃ followed by the addition of N-Chlorosuccinimide (12.6 g, 92 mmol). The reaction mixture was stirred after 1 h then allowed to warm to ambient temperature and stirred until the aldehydes was completely consumed. 7 hours later, pentane was added to the reaction mixture and the precipitated N-Chlorosuccinimide succinimide and the catalysts were filtered off. The solution was washed with water 2 times and dried with Na₂SO₄, the solution was directly used to next step.

Step B: methyl 2-(2-methoxy-2-oxoethyl)-5-methylfuran-3-carboxylate

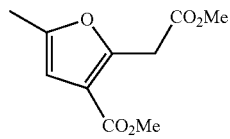

To a solution of dimethyl 3-oxopentanedioate (13.5 g, 77 mmol) in 20 mL pyridine, 2-chloropropanal in pentane (77 mmol) was added dropwise at room temperature, after the addition, the reaction mixture was heat at 60° C. overnight, then water and EtOAc were added, the mixture was extracted with EtOAc thrice, the combined organic layers was dried over Na₂SO₄, filtered, the filtrate was concentrated in vacuum, the residue was purified by column chromatography on silica gel to get the desired product (11.7 g, 70%). ¹H NMR (400 MHz, CDCl₃) δ 6.27 (s, 1H), 4.03 (s, 2H), 0.79 (s, 3H), 3.73 (s, 3H), 2.28 (s, 3H); m/z=213 [M+1]⁺.

Step C: methyl 6-(2-fluoro-4-iodophenylamino)-2,5-dimethyl-4-oxo-4,5-dihydrofuro[3,2-c]pyridine-7-carboxylate

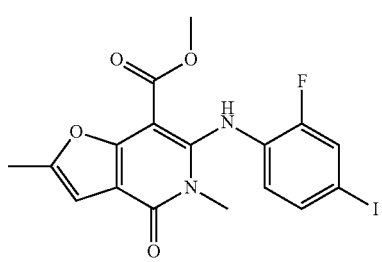 [SMILES: COC(=O)c1c(Nc2ccc(I)cc2F)n(C)c(=O)c2cc(C)oc12]

According to the procedure B, methyl 2-(2-methoxy-2-oxoethyl)-5-methylfuran-3-carboxylate was reacted with 2-fluoro-4-iodo-N-((methylimino)methylene)aniline to obtain the desired product. ¹H NMR (400 MHz, CDCl₃) δ 9.67 (s, 1H), 7.47-7.50 (dd, J=1.6 & 9.6 Hz, 1H), 7.34-7.36 (dd, J=1.2 & 8.4 Hz, 1H), 6.54 (s, 1H), 6.38-6.42 (t, J=8.4 Hz, 1H), 3.95 (s, 3H), 3.36 (s, 3H), 2.45 (m, 3H); m/z=457 [M+1]⁺.

Step D: 6-(2-fluoro-4-iodophenylamino)-2,5-dimethyl-4-oxo-4,5-dihydrofuro[3,2-c]pyridine-7-carboxylic acid

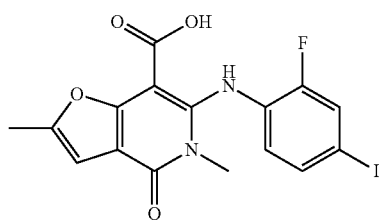 [SMILES: Cc1cc2c(=O)n(C)c(Nc3ccc(I)cc3F)c(C(=O)O)c2o1]

Following the same procedure as step C, example 1 described, the title product was obtained via column chromatography purification.

Step E: 6-(2-fluoro-4-iodophenylamino)-N-(2-hydroxyethoxy)-2,5-dimethyl-4-oxo-4,5-dihydrofuro[3,2-c]pyridine-7-carboxamide

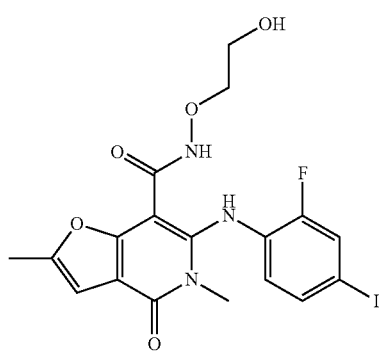 [SMILES: Cc1cc2c(=O)n(C)c(Nc3ccc(I)cc3F)c(C(=O)NOCCO)c2o1]

Following the same procedure as step D, example 1 described, the title product was obtained. $^1$H NMR (400 MHz, CDCl$_3$) δ 10.67 (s, 1H), 9.87 (s, 1H), 7.48 (d, J=10.0 Hz, 1H), 7.37 (d, J=8.0 Hz, 1H), 6.58 (s, 1H), 6.50 (t, J=8.0 Hz, 1H), 4.10-4.11 (m, 3H), 3.78 (m, 2H), 3.30 (s, 3H), 2.48 (s, 3H); m/z=502 [M+1]$^+$, 425 [M-NHOCH$_2$CH$_2$OH]$^+$.

Example 3

6-(4-Bromo-2-fluorophenylamino)-N-(2-hydroxyethoxy)-5-methyl-4-oxo-4,5-dihydrofuro[3,2-c]pyridine-7-carboxamide

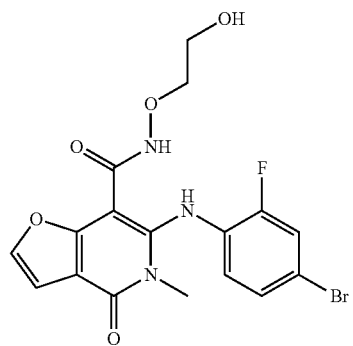

Following the same procedure as example 1 described, using 4-bromo-2-fluoro-N-((methylimino)methylene)aniline as starting material to get the product. $^1$H NMR (400 MHz, CDCl$_3$) δ 10.84 (s, 1H), 9.87 (s, 1H), 7.52 (d, J=2.0 Hz, 1H), 7.33 (dd, J=2.0 & 10.0 Hz, 1H), 7.22 (d, J=8.4 Hz, 1H), 7.02 (d, J=2.0 Hz, 1H), 6.70 (t, J=8.4 Hz, 1H), 4.09-4.12 (m, 3H), 3.77 (m, 2H), 3.30 (s, 3H); m/z=363 [M-NHOCH$_2$CH$_2$OH]$^+$, 440 [M+1]$^+$.

Example 4

(S)-6-(2-Fluoro-4-iodophenylamino)-N-(2-hydroxypropoxy)-5-methyl-4-oxo-4,5-dihydrofuro[3,2-c]pyridine-7-carboxamide

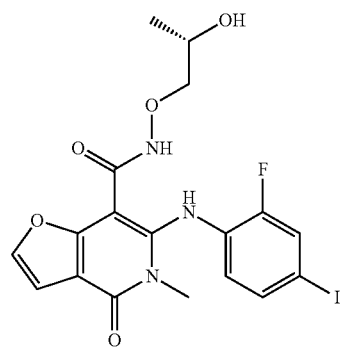 [SMILES: C[C@H](O)CONC(=O)c1c(Nc2ccc(I)cc2F)n(C)c(=O)c2ccoc12]

According to procedure C, 6-(2-fluoro-4-iodophenylamino)-5-methyl-4-oxo-4,5-dihydrofuro[3,2-c]pyridine-7-carboxylic acid was coupling with (S)—O-(2-(tert-butyl dimethylsilyloxy)propyl)hydroxylamine (made according to WO2010003025 A1), followed by de-TBS by 2 N HCl in MeOH to afford the title compound. $^1$H NMR (400 MHz, CDCl$_3$) δ 10.86 (s, 1H), 9.91 (s, 1H), 7.52 (d, J=1.6 Hz, 1H), 7.48 (d, J=8.4 Hz, 1H), 7.39 (d, J=8.4 Hz, 1H), 7.01 (d, J=1.6 Hz, 1H), 6.55 (t, J=8.4 Hz, 1H), 4.41 (s, 1H), 4.01-3.98 (m, 2H), 3.77-3.71 (m, 1H), 3.30 (s, 3H); m/z=411 [M-NHOCH$_2$CH(CH$_3$)OH]$^+$, 502 [M+1]$^+$.

Example 5

(S)-6-(2-Fluoro-4-iodophenylamino)-N-(1-hydroxypropan-2-yloxy)-5-methyl-4-oxo-4,5-dihydrofuro[3,2-c]pyridine-7-carboxamide

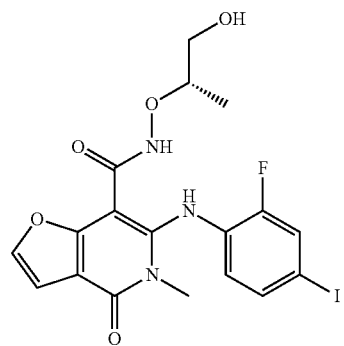 [SMILES: C[C@@H](CO)ONC(=O)c1c(Nc2ccc(I)cc2F)n(C)c(=O)c2ccoc12]

Step A: (R)-1-(tert-butyldimethylsilyloxy)propan-2-ol

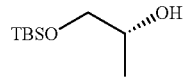

To a solution of (R)-propane-1,2-diol (20 g, 0.36 mmol) and triethylamine (50.8 mL, 0.34 mmol) in $CH_2Cl_2$ was added tert-butylchlorodimethylsilane (39.6 g, 0.26 mmol). After stirring overnight at room temperature, the reaction mixture was washed one time each with 1 N aqueous HCl solution, water, and a 1:1 saturated solution of $NaHCO_3$ and brine. The organic layer was dried over $Na_2SO_4$, then filtered and concentrated. The crude title compound was used without further purification in the next step.

Step B: (S)-2-(1-(tert-butyldimethylsilyloxy)propan-2-yloxy)isoindoline-1,3-dione

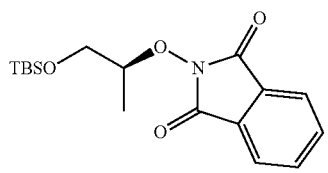 [SMILES: C[C@@H](CO[Si](C)(C)C(C)(C)C)ON1C(=O)c2ccccc2C1=O]

DEAD (52.7 g) was added dropwise to a solution of (R)-1-(tert-butyldimethylsilyloxy)propan-2-ol (44.3 g), $PPh_3$ (61 g), and N-hydroxyphthalimide (38 g) in THF (500 mL) at 0° C. After stirring for 10 min at 0° C., the reaction mixture was brought to room temperature and stirring was continued for a further 24 h. The reaction mixture was filtered through a coarse glass funnel and concentrated in vacuo. The residue was purified by silica chromatography to afford the title compound (97%) as a clear oil.

Step C: (S)—O-(1-(tert-butyldimethylsilyloxy)propan-2-yl)hydroxylamine

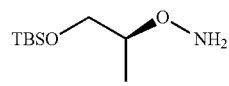

N-methylhydrazine (13.12 g, 0.85 mmol) was added to a solution of (S)-2-(1-(tert-butyldimethylsilyloxy)propan-2-yloxy)isoindoline-1,3-dione (91 g, 0.27 mmol) in $CH_2Cl_2$ (300 mL). After stirring for 1 h at room temperature, the white precipitate was filtered off and the reaction mixture was concentrated in vacuo to afford the title compound (37 g, 66%) as a yellow oil. $^1H$ NMR (400 MHz, $CDCl_3$) δ 5.30 (s, 2H), 3.51-3.67 (m, 3H), 1.03-1.06 (m, 3H), 0.79-0.83 (m, 9H), 0.00 (s, 6H).

Step D: (S)—N-(1-(tert-butyldimethylsilyloxy)propan-2-yloxy)-6-(2-fluoro-4-iodo phenylamino)-5-methyl-4-oxo-4,5-dihydrofuro[3,2-c]pyridine-7-carboxamide

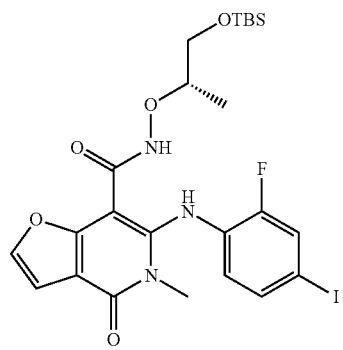 [SMILES: C[C@@H](CO[Si](C)(C)C(C)(C)C)ONC(=O)c1c(Nc2ccc(I)cc2F)n(C)c(=O)c2ccoc12]

According to procedure C, 6-(2-fluoro-4-iodophenylamino)-5-methyl-4-oxo-4,5-dihydrofuro[3,2-c]pyridine-7-carboxylic acid was coupling with (S)—O-(1-(tert-butyl dimethylsilyloxy)propan-2-yl)hydroxylamine to get the title compound.

Step E: (S)-6-(2-fluoro-4-iodophenylamino)-N-(1-hydroxypropan-2-yloxy)-5-methyl-4-oxo-4,5-dihydrofuro[3,2-c]pyridine-7-carboxamide

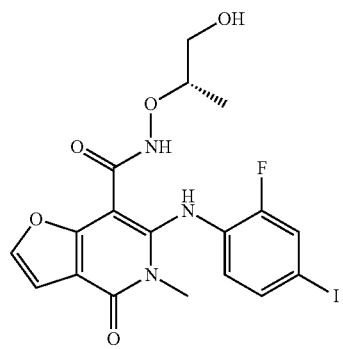 [SMILES: C[C@@H](CO)ONC(=O)c1c(Nc2ccc(I)cc2F)n(C)c(=O)c2ccoc12]

To a stirred solution of (S)—N-(1-(tert-butyldimethylsilyloxy)propan-2-yloxy)-6-(2-fluoro-4-iodophenylamino)-5-methyl-4-oxo-4,5-dihydrofuro[3,2-c]pyridine-7-carboxamide (100 mg) in MeOH (10 mL) was added 2 N HCl (aq.) (3 mL) at room temperature and the mixture was stirred for 10 min. Then concentrated in vacuum, residue was partitioned between water and ethyl acetate, water phase was extracted thrice and the combined organic phase was washed with water, dried ($MgSO_4$) and concentrated under reduced pressure. The residue was purified by flash column chromatography on silica gel to obtain the title product (53 mg). $^1H$ NMR (400 MHz, $CDCl_3$) δ 10.83 (s, 1H), 9.75 (s, 1H), 7.53 (d, J=1.6 Hz, 1H), 7.47 (d, J=8.4 Hz, 1H), 7.40 (d, J=8.4 Hz, 1H), 7.02 (d, J=1.6 Hz, 1H), 6.55 (t, J=8.4 Hz, 1H), 4.20-4.11 (m, 2H), 3.71-3.69 (m, 1H), 3.52-3.48 (m, 1H), 3.30 (s, 3H), 1.34 (d, J=6.4 Hz, 3H); m/z=411 [M-NHOCH($CH_3$)$CH_2OH$]$^+$, 502 [M+1]$^+$.

Example 6

6-(2-Fluoro-4-iodophenylamino)-N-(2-methoxyethoxy)-5-methyl-4-oxo-4,5-dihydrofuro[3,2-c]pyridine-7-carboxamide

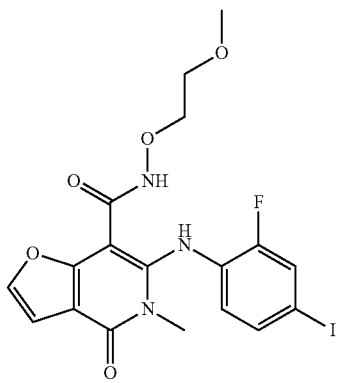 [SMILES: COCCONC(=O)c1c(Nc2ccc(I)cc2F)n(C)c(=O)c2ccoc12]

According to procedure C, 6-(2-fluoro-4-iodophenylamino)-5-methyl-4-oxo-4,5-dihydrofuro[3,2-c]pyridine-7-carboxylic acid was reacted with O-(2-methoxyethyl)hydroxylamine (made according to WO2008070758 A1) to get the desired product. $^1$H NMR (400 MHz, CDCl$_3$) δ 10.98 (s, 1H), 10.17 (s, 1H), 7.46-7.50 (m, 2H), 7.36-7.38 (d, J=8.4 Hz, 1H), 7.01-7.02 (dd, J=0.8 Hz & 2.0 Hz, 1H), 6.47-6.52 (t, J=8.4 Hz, 1H), 4.19-4.22 (m, 2H), 3.70-3.72 (m, 2H), 3.45 (s, 3H), 3.32 (s, 3H); J=8.4 Hz, 1H), 7.02 (d, J=1.6 Hz, 1H), 6.55 (t, J=8.4 Hz, 1H), 4.20-4.11 (m, 2H), 3.71-3.69 (m, 1H), 3.52-3.48 (m, 1H), 3.30 (s, 3H), 1.34 (d, J=6.4 Hz, 3H); m/z=411 [M-NHOCH$_2$CH$_2$OCH$_3$]$^+$, 502 [M+1]$^+$.

Example 7

N-(Cyclopropylmethoxy)-6-(2-fluoro-4-iodophenylamino)-5-methyl-4-oxo-4,5-dihydrofuro[3,2-c] pyridine-7-carboxamide

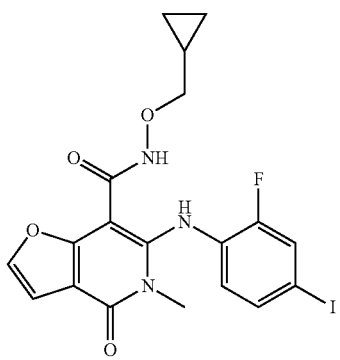 [SMILES: Cn1c(Nc2ccc(I)cc2F)c(C(=O)NOCC2CC2)c2occc2c1=O]

According to procedure C, 6-(2-fluoro-4-iodophenylamino)-5-methyl-4-oxo-4,5-dihydrofuro[3,2-c]pyridine-7-carboxylic acid was reacted with O-(cyclopropylmethyl) hydroxylamine (made according to WO2005054179) to get the desired product. $^1$H NMR (400 MHz, CDCl$_3$) δ 10.99 (s, 1H), 9.86 (s, 1H), 7.46-7.52 (m, 2H), 7.36-7.38 (d, J=8.4 Hz, 1H), 7.26-7.27 (d, J=0.4 Hz, 1H) 7.01-7.02 (t, J=0.8 Hz, 1H), 6.48-6.52 (t, J=8.4 Hz, 1H), 3.86-3.88 (d, J=7.2 Hz, 2H), 3.32 (s, 3H), 1.19-1.26 (m, 1H), 0.61-0.66 (m, 2H) 0.33-0.37 (m, 2H); m/z=498 [M+1]$^+$.

Example 8

6-(2-Fluoro-4-iodophenylamino)-N-(1-hydroxy-2-methylpropan-2-yloxy)-5-methyl-4-oxo-4,5-dihydrofuro[3,2-c]pyridine-7-carboxamide

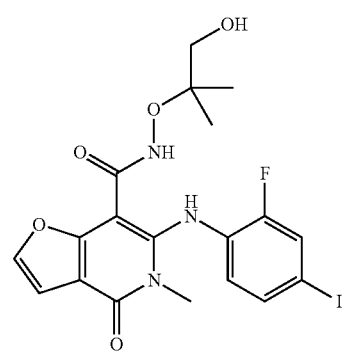 [SMILES: Cn1c(Nc2ccc(I)cc2F)c(C(=O)NOC(C)(C)CO)c2occc2c1=O]

According to procedure C, 6-(2-fluoro-4-iodophenylamino)-5-methyl-4-oxo-4,5-dihydrofuro[3,2-c]pyridine-7-carboxylic acid was reacted with 2-(aminooxy)-2-methylpropan-1-ol hydrochloride (made according to WO2010003025 A1) to get the desired product. $^1$H NMR (400 MHz, CDCl$_3$) δ 10.80 (s, 1H), 9.46 (s, 1H), 7.47-7.53 (m, 2H), 7.38-7.41 (dd, J=0.8 Hz & 8.4 Hz, 1H), 7.02-7.03 (d, J=2.0 Hz, 1H), 6.53-6.57 (t, J=8.4 Hz, 1H), 4.50-4.52 (t, J=7.2 Hz, 1H), 3.39-3.41 (d, J=7.2 Hz, 2H), 3.31 (s, 3H), 1.24-1.34 (m, 6H); m/z=411 [M-NHOC(CH$_3$)$_2$CH$_2$OH]$^+$, 516 [M+1]$^+$.

Example 9

(R)—N-(2,3-Dihydroxypropoxy)-6-(2-fluoro-4-iodophenylamino)-5-methyl-4-oxo-4,5-dihydrofuro[3,2-c]pyridine-7-carboxamide

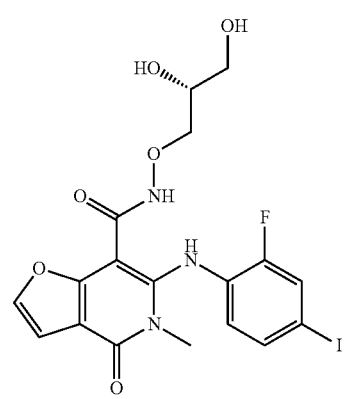 [SMILES: Cn1c(Nc2ccc(I)cc2F)c(C(=O)NOC[C@H](O)CO)c2occc2c1=O]

According to procedure C, 6-(2-fluoro-4-iodophenylamino)-5-methyl-4-oxo-4,5-dihydrofuro[3,2-c]pyridine-7-carboxylic acid was reacted with (R)—O-((2,2-dimethyl-1,3-dioxolan-4-yl)methyl)hydroxylamine (made according to *Tetrahedron Letters*, 2006, 47, 7607-7609), followed by treating with 2 N HCl in MeOH to get the desired product.

¹H NMR (400 MHz, CDCl₃) δ 10.79 (s, 1H), 9.99 (s, 1H), 7.48-7.53 (m, 2H), 7.39-7.41 (d, J=8.4 Hz, 1H), 7.01-7.02 (d, J=2.0 Hz, 1H), 6.54-6.58 (t, J=8.4 Hz, 1H), 4.44-4.45 (d, J=3.2 Hz, 1H), 4.03-4.14 (m, 2H), 3.97-3.99 (m, 1H), 3.63-3.76 (m, 2H), 3.30 (s, 3H), 2.38-2.41 (t, 1H); m/z=411 [M-NHOCH₂CH(OH)CH₂OH]⁺, 518 [M+1]⁺.

Example 10

(S)-6-(2-Fluoro-4-iodophenylamino)-N-(2-hydroxybutoxy)-5-methyl-4-oxo-4,5-dihydrofuro[3,2-c]pyridine-7-carboxamide

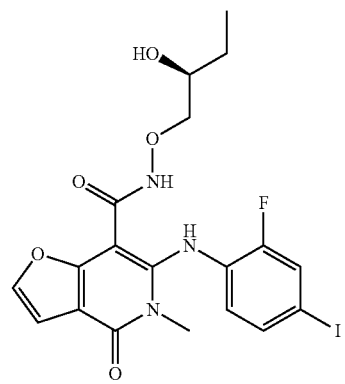 [SMILES: CC[C@H](O)CONC(=O)c1c(Nc2ccc(I)cc2F)n(C)c(=O)c2ccoc12]

Step A: (S)-1-(benzyloxy)butan-2-ol

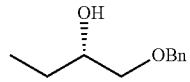

To a CuCN (109 mg, 4%) was added dry THF (100 mL) under N₂, and the suspension was then cooled to −15° C. MeMgBr (3 M in ether, 13 mL) was added dropwise and the reaction mixture was stirred at −15° C. for 15 min, Then, (S)-benzyl glycidyl ether (5 g, 30 mmol) was added and the mixture was stirred at the same temperature for 1 h. The reaction mixture was quenched with aqueous sat. NH₄Cl and 25% NH₃ solution and the resulting mixture was stirred at room temperature until the color turned blue. The organic layers were extracted with ether washed with brine, dried by MgSO₄, filtered and evaporated in vacuo. The material was used without further purification in the subsequent step. ¹H NMR (400 MHz, CDCl₃) δ 7.29-7.36 (m, 5H), 4.54 (s, 2H), 3.72-3.74 (m, 1H), 3.50 (dd, J=2.8 Hz & 9.6 Hz, 1H), 3.33 (dd, J=8.0 Hz & 9.6 Hz, 1H), 2.52 (d, J=3.2 Hz, 1H), 1.44-1.49 (m, 2H), 0.95 (t, J=7.6 Hz, 3H).

Step B: (S)-(1-(benzyloxy)butan-2-yloxy)(tert-butyl)dimethylsilane

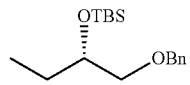

To a solution of (S)-1-(benzyloxy)butan-2-ol (41.4 g, 0.23 mol) in CH₂Cl₂ (200 mL) was added imidazole (23.5 g, 0.36 mol) and TBSCl (36.4 g, 0.24 mol) and DMAP (600 mg, 0.005 mol). The reaction mixture was stirred at room temperature overnight. The reaction was diluted with water and extracted with CH₂Cl₂ thrice, the combined organic extracts washed with brine and dried over MgSO₄, filtered, concentrated in vacuo to give the title product as a colorless oil (99%). ¹H NMR (400 MHz, CDCl₃) δ 7.19-7.22 (m, 5H), 4.48 (s, 2H), 3.70-3.73 (m, 1H), 3.29-3.37 (m, 2H), 1.52-1.55 (m, 1H), 1.39-1.44 (m, 1H), 0.81-0.87 (m, 12H), 0.01 (s, 6H).

Step C: (S)-2-(tert-butyldimethylsilyloxy)butan-1-ol

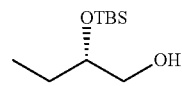

To a solution of (S)-(1-(benzyloxy)butan-2-yloxy)(tert-butyl)dimethylsilane in ethyl acetate (400 mL) was added 20% Pd/C (2 g). The reaction mixture was evacuated and flushed with H₂, then stirred under an atmosphere of H₂ (1 atm) overweekends. The reaction mixture was then filtered through celite and concentrated to afford the title compound (45 g, 97% yield) as clear oil, which was used without further purification in the next step.

Step D: (S)-2-(2-(tert-butyldimethylsilyloxy)butoxy)isoindoline-1,3-dione

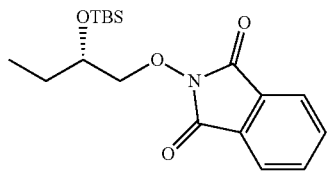 [SMILES: CC[C@@H](CON1C(=O)c2ccccc2C1=O)O[Si](C)(C)C(C)(C)C]

Following the same procedure as step B, example 5 described, the title product was obtained.

Step E: (S)—O-(2-(tert-butyldimethylsilyloxy)butyl)hydroxylamine

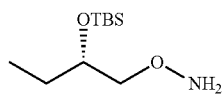

Following the same procedure as step C, example 5 described, the title product was obtained. ¹H NMR (400 MHz, CDCl₃): δ 5.36 (s, 2H), 3.70-3.75 (m, 1H), 3.49-3.57 (m, 2H), 1.33-1.51 (m, 2H), 0.81-0.88 (m, 12H), 0.00 (s, 6H).

Step F: (S)—N-(2-(tert-butyldimethylsilyloxy)butoxy)-6-(2-fluoro-4-iodophenylamino)-5-methyl-4-oxo-4,5-dihydrofuro[3,2-c]pyridine-7-carboxamide

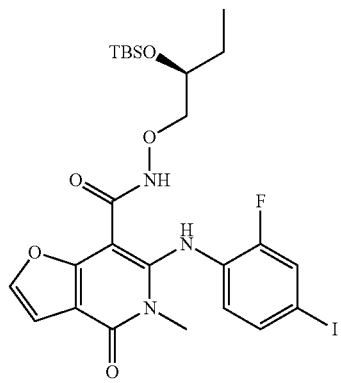 [SMILES: CC[C@@H](CONC(=O)c1c(Nc2ccc(I)cc2F)n(C)c(=O)c2ccoc12)O[Si](C)(C)C(C)(C)C]

According to procedure C, 6-(2-fluoro-4-iodophenylamino)-5-methyl-4-oxo-4,5-dihydrofuro[3,2-c]pyridine-7-carboxylic acid was coupling with (S)—O-(2-(tert-butyldimethyl silyloxy)butyl)hydroxylamine to give the title compound.

Step G: (S)-6-(2-fluoro-4-iodophenylamino)-N-(2-hydroxybutoxy)-5-methyl-4-oxo-4,5-dihydrofuro[3,2-c]pyridine-7-carboxamide

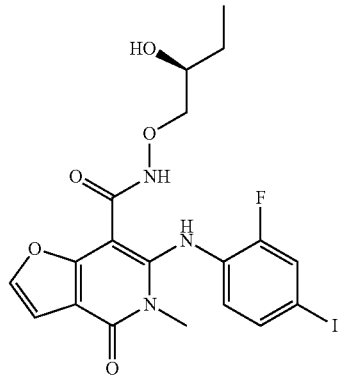 [SMILES: CC[C@H](O)CONC(=O)c1c(Nc2ccc(I)cc2F)n(C)c(=O)c2ccoc12]

Following the same procedure as step E, example 5 described, the title product was obtained. $^1$H NMR (400 MHz, CDCl$_3$): δ 10.87 (s, 1H), 9.92 (s, 1H), 7.53 (d, J=1.6 Hz, 1H), 7.51 (d, J=8.4 Hz, 1H), 7.47 (d, J=8.4 Hz, 1H), 7.02 (d, J=1.6 Hz, 1H), 6.56 (t, J=8.4 Hz, 1H), 4.33 (s, 1H), 4.06-4.04 (m, 1H), 3.82-3.80 (m, 2H), 3.30 (s, 3H), 1.58-1.41 (m, 2H), 0.97 (t, J=2.4 Hz, 3H); m/z=411 [M-NHOCH$_2$CH(OH)CH$_2$CH$_3$]$^+$, 516 [M+1]$^+$.

Example 11

6-(2,4-Dichlorophenylamino)-N-(2-hydroxyethoxy)-5-methyl-4-oxo-4,5-dihydrofuro[3,2-c]pyridine-7-carboxamide

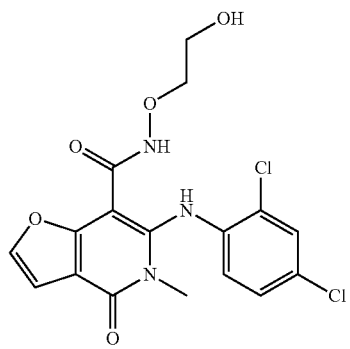 [SMILES: Cn1c(Nc2ccc(Cl)cc2Cl)c(C(=O)NOCCO)c2occc2c1=O]

Following the same procedure as example 1 described, using 2,4-dichloro-N-((methylimino)methylene)aniline as starting material to get the product. $^1$H NMR (400 MHz, CDCl$_3$) δ 10.80 (s, 1H), 9.86 (s, 1H), 7.54 (d, J=2.4 Hz, 1H), 7.49 (d, J=2.4 Hz, 1H), 7.15 (dd, J=2.4 & 8.4 Hz, 1H), 7.03 (d, J=2.4 Hz, 1H), 6.60 (d, J=8.8 Hz, 1H), 4.10-4.12 (m, 2H), 4.03 (t, J=6.4 Hz, 1H), 3.77-3.79 (m, 2H), 3.26 (s, 3H); m/z=434 [M+Na]$^+$, 335 [M-NHOCH$_2$CH$_2$OH]$^+$, 412 [M+1]$^+$.

Example 12

6-(4-Bromo-2-chlorophenylamino)-N-(2-hydroxyethoxy)-5-methyl-4-oxo-4,5-dihydrofuro[3,2-c]pyridine-7-carboxamide

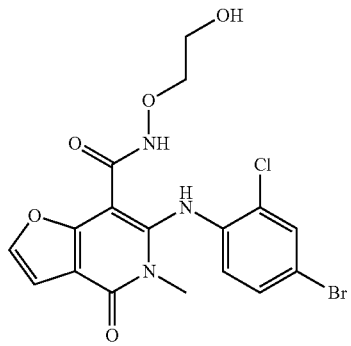 [SMILES: Cn1c(Nc2ccc(Br)cc2Cl)c(C(=O)NOCCO)c2occc2c1=O]

Following the same procedure as example 1 described, using 4-bromo-2-chloro-N-((methylimino)methylene)aniline as starting material to get the product. $^1$H NMR (400 MHz, CDCl$_3$) δ 10.78 (s, 1H), 9.85 (s, 1H), 7.63 (d, J=2.4 Hz, 1H), 7.54 (d, J=2.0 Hz, 1H), 7.29 (dd, J=2.0 & 8.4 Hz, 1H), 7.03 (d, J=2.4 Hz, 1H), 6.53 (d, J=8.4 Hz, 1H), 4.10-4.13 (m, 2H), 4.02 (t, J=6.4 Hz, 1H), 3.75-3.79 (m, 2H), 3.27 (s, 3H); m/z=478 [M+Na]$^+$, 379 [M-NHOCH$_2$CH$_2$OH]$^+$, 456 [M+1]$^+$.

Example 13

6-(2-Fluoro-4-iodophenylamino)-N-methoxy-5-methyl-4-oxo-4,5-dihydrofuro[3,2-c]pyridine-7-carboxamide

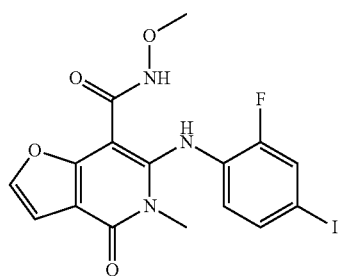 [SMILES: CONC(=O)c1c(Nc2ccc(I)cc2F)n(C)c(=O)c2ccoc12]

According to procedure C, 6-(2-fluoro-4-iodophenylamino)-5-methyl-4-oxo-4,5-dihydrofuro[3,2-c]pyridine-7-carboxylic acid was reacted with O-methylhydroxylamine to get the desired product. $^1$H NMR (400 MHz, CDCl$_3$) δ 10.99 (s, 1H), 9.86 (s, 1H), 7.52 (d, J=2.0 Hz, 1H), 7.48 (dd, J=2.0 & 10.0 Hz, 1H), 7.38 (d, J=8.4 Hz, 1H), 7.02 (d, J=2.0 Hz, 1H), 6.51 (t, J=8.4 Hz, 1H), 3.91 (s, 3H), 3.33 (s, 3H); m/z=458 [M+1]$^+$, 426 [M-OCH$_3$]$^+$, 411 [M-NHOCH$_3$]$^+$.

Example 14

N-Ethoxy-6-(2-fluoro-4-iodophenylamino)-5-methyl-4-oxo-4,5-dihydrofuro[3,2-c]pyridine-7-carboxamide

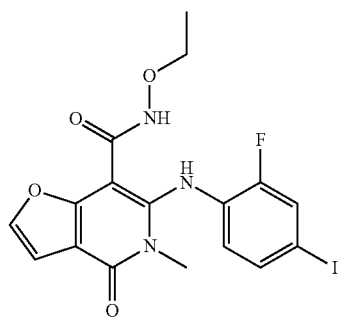 [SMILES: CCONC(=O)c1c(Nc2ccc(I)cc2F)n(C)c(=O)c2ccoc12]

According to procedure C, 6-(2-fluoro-4-iodophenylamino)-5-methyl-4-oxo-4,5-dihydrofuro[3,2-c]pyridine-7-carboxylic acid was reacted with O-ethylhydroxylamine to get the desired product. $^1$H NMR (400 MHz, CDCl$_3$) δ 11.01 (s, 1H), 9.80 (s, 1H), 7.52 (d, J=2.0 Hz, 1H), 7.46-7.49 (dd, J=2.0 Hz & 10 Hz, 1H), 7.36-7.38 (d, J=8.8 Hz, 1H), 7.01-7.02 (d, J=2.0 Hz, 1H), 6.48-6.52 (t, J=8.4 Hz, 1H), 4.08-4.13 (m, 2H), 3.33 (s, 3H), 1.33-1.37 (m, 3H); m/z=472 [M+1]$^+$, 426 [M-OCH$_2$CH$_3$]$^+$, 411 [M-NHOCH$_2$CH$_3$]$^+$.

Example 15

6-(2-Fluoro-4-iodophenylamino)-5-methyl-4-oxo-4,5-dihydrofuro[3,2-c]pyridine-7-carboxamide

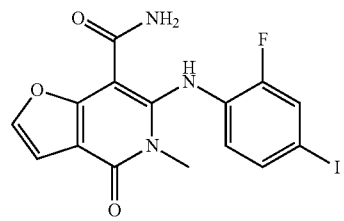 [SMILES: Cn1c(Nc2ccc(I)cc2F)c(C(N)=O)c2occc2c1=O]

According to procedure C, 6-(2-fluoro-4-iodophenylamino)-5-methyl-4-oxo-4,5-dihydrofuro[3,2-c]pyridine-7-carboxylic acid was reacted with ammonium hydroxide (25%) to get the desired product. $^1$H NMR (400 MHz, DMSO-D6) δ 10.93 (s, 1H), 8.25 (s, 1H), 7.88 (s, 1H), 7.83-7.84 (d, J=3 Hz, 1H), 7.60-7.62 (dd, J=2.0 Hz & 10.4 Hz, 1H), 7.51 (s, 1H), 7.40-7.42 (d, J=8.4 Hz, 1H), 6.62-6.66 (t, J=8.6 Hz, 1H), 4.08-4.13 (m, 2H), 3.33 (s, 3H); m/z=428 [M+1]$^+$, 411 [M-NH$_2$]$^+$.

Example 16

N-(2,3-Dihydroxypropyl)-6-(2-fluoro-4-iodophenylamino)-5-methyl-4-oxo-4,5-dihydrofuro[3,2-c]pyridine-7-carboxamide

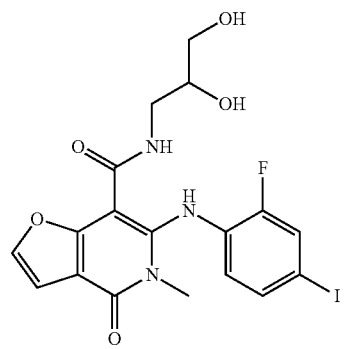 [SMILES: Cn1c(Nc2ccc(I)cc2F)c(C(=O)NCC(O)CO)c2occc2c1=O]

According to procedure C, 6-(2-fluoro-4-iodophenylamino)-5-methyl-4-oxo-4,5-dihydrofuro[3,2-c]pyridine-7-carboxylic acid was reacted with (±)-3-amino-1,2-propanediol to get the desired product. $^1$H NMR (400 MHz, CDCl$_3$) δ 11.14 (s, 1H), 7.80-7.83 (t, J=5.4 Hz, 1H), 7.52 (d, 1H), 7.47-7.49 (dd, J=1.6 Hz & 8.8 Hz, 1H), 7.36-7.38 (d, J=8.4 Hz, 1H), 6.47-6.51 (t, J=8.4 Hz, 1H), 3.89-3.92 (m, 2H), 3.56-3.69 (m, 4H), 3.32 (s, 3H), 2.84-2.86 (d, J=3 Hz, 1H), 2.57-2.60 (t, 1H); m/z=502 [M+1]$^+$, 411 [M-NHCH$_2$CH(OH)CH$_2$OH]$^+$.

Example 17

6-(2-Chloro-4-iodophenylamino)-N-(2-hydroxy-ethoxy)-5-methyl-4-oxo-4,5-dihydrofuro[3,2-c]pyridine-7-carboxamide

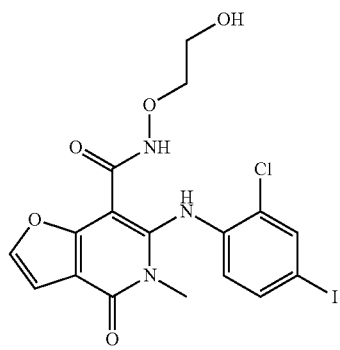

Following the same procedure as example 1 described, using 2-chloro-4-iodo-N-((methylimino)methylene)aniline as starting material to get the product. $^1$H NMR (400 MHz, DMSO-D6) δ11.35 (s, 1H), 8.90 (s, 1H), 7.93-7.94 (d, J=2.4 Hz, 1H), 7.76-7.75 (d, J=2.0 Hz, 1H), 7.44-7.47 (dd, J=1.8 Hz & 8.6 Hz, 1H), 7.01-7.02 (d, J=2.4 Hz, 1H), 6.44-6.46 (d, J=8.4 Hz, 1H), 4.65 (s, 1H), 3.69-3.71 (t, J=5.0 Hz, 2H), 3.48-3.49 (d, J=4.8 Hz, 2H), 3.31 (s, 3H); m/z=427 [M-NHOCH$_2$CH$_2$OH]$^+$, 504 [M+1]$^+$.

Example 18

6-(2-Fluoro-4-iodophenylamino)-N-(3-hydroxypropyl)-5-methyl-4-oxo-4,5-dihydrofuro[3,2-c]pyridine-7-carboxamide

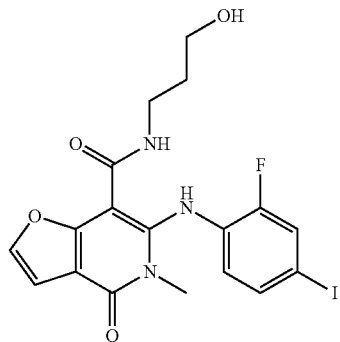

According to procedure C, 6-(2-fluoro-4-iodophenylamino)-5-methyl-4-oxo-4,5-dihydrofuro[3,2-c]pyridine-7-carboxylic acid was reacted with 3-methoxypropan-1-amine then treated with BBr$_3$ at 0° C. to get the desired product. $^1$H NMR (400 MHz, CDCl$_3$) δ 11.25 (s, 1H), 7.70-7.72 (d, 1H), 7.48-7.51 (dd, J=2.0 Hz & 9.6 Hz, 1H), 7.35-7.37 (d, J=8.4 Hz, 1H), 7.26 (s, 1H), 7.02 (d, 1H), 6.46-6.51 (t, J=8.8 Hz, 1H), 3.68-3.72 (m, 2H), 3.61-3.66 (m, 2H), 3.33 (s, 3H), 1.57-1.86 (m, 2H); m/z=486 [M+1]$^+$, 411 [M-NHCH$_2$CH$_2$CH$_2$OH]$^+$.

Example 19

6-(2-Fluoro-4-iodophenylamino)-N-(2-hydroxy-ethoxy)-5-methyl-4-oxo-4,5-dihydrothieno[3,2-c]pyridine-7-carboxamide

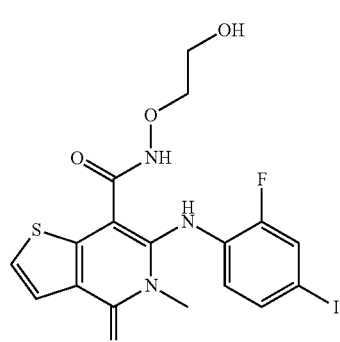

Step A: methyl 2-(2-methoxy-2-oxoethyl)thiophene-3-carboxylate

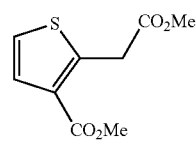

According to WO 2005087779, the title compound was made. $^1$H NMR (400 MHz, DMSO-D6) δ 7.46 (d, J=5.6 Hz, 1H), 7.36 (d, J=5.6 Hz, 1H), 4.21 (s, 2H), 3.73 (s, 3H), 3.61 (s, 3H).

Step B: methyl 6-(2-fluoro-4-iodophenylamino)-5-methyl-4-oxo-4,5-dihydrothieno[3,2-c]pyridine-7-carboxylate

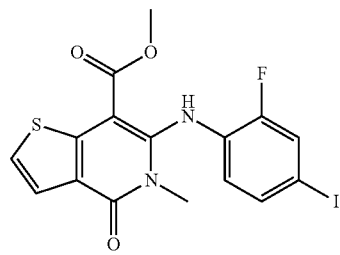 [SMILES: COC(=O)c1c(Nc2ccc(I)cc2F)n(C)c(=O)c2ccsc12]

According to the procedure B, methyl 2-(2-methoxy-2-oxoethyl)thiophene-3-carboxylate was reacted with 2-fluoro-4-iodo-N-((methylimino)methylene)aniline to obtain the desired product. $^1$H NMR (400 MHz, DMSO-D6) δ 9.05 (s, 1H), 7.67 (dd, J=2.0 & 11.2 Hz, 1H), 7.45-7.57 (m, 2H), 7.38 (d, J=8.0 Hz, 1H), 6.65 (t, J=8.8 Hz, 1H), 3.69 (s, 3H), 3.35 (s, 3H).

Step C: 6-(2-fluoro-4-iodophenylamino)-5-methyl-4-oxo-N-(2-(vinyloxy)ethoxy)-4,5-dihydrothieno[3,2-c]pyridine-7-carboxamide

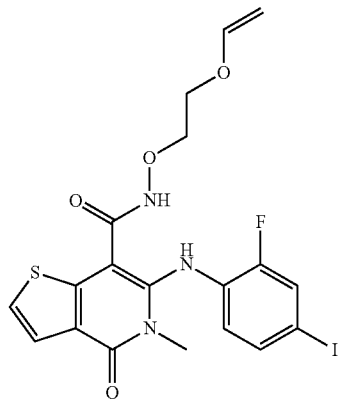 [SMILES: C=COCCONC(=O)c1c(Nc2ccc(I)cc2F)n(C)c(=O)c2ccsc12]

To a solution of methyl 6-(2-fluoro-4-iodophenylamino)-5-methyl-4-oxo-4,5-dihydrothieno[3,2-c]pyridine-7-carboxylate (119 mg, 0.26 mmol) in 5 mL THF was added O-(2-(vinyloxy)ethyl)hydroxylamine (33 mg, 0.32 mmol). The solution was cooled to 0° C. and 1 mL 1 M lithium bis(trimethylsilyl)amide (1 mmol) was added dropwise. The reaction mixture was then warmed to room temperature and stirred for 30 min, then quenched with NH₄Cl (aq.), and partitioned between CH₂Cl₂ and saturated NaCl. The organic layers was separated, dried, filtered, purified by column chromatography on silica gel (petroleum ether: EtOAc=1:1) to obtain the titled product (quantitively).

Step D: 6-(2-fluoro-4-iodophenylamino)-N-(2-hydroxyethoxy)-5-methyl-4-oxo-4,5-dihydrothieno[3,2-c]pyridine-7-carboxamide

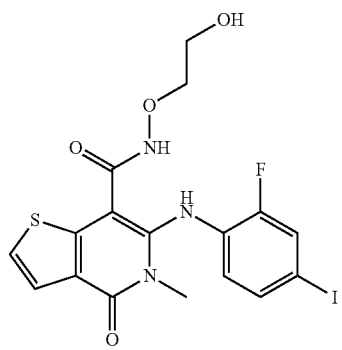

To a solution of 6-(2-fluoro-4-iodophenylamino)-5-methyl-4-oxo-N-(2-(vinyloxy)ethoxy)-4,5-dihydrothieno[3,2-c]pyridine-7-carboxamide (139 mg, 0.26 mmol) in 5 mL MeOH was added 1.5 mL 2 N HCl (aq). The reaction mixture was stirred for 30 min at room temperature. The reaction mixture was diluted with CH₂Cl₂ and H₂O. The suspension was filtered and dried to give the product as white solid (54 mg, 40%). ¹H NMR (400 MHz, DMSO-D6) δ 11.31 (s, 1H), 8.30 (s, 1H), 7.62-7.63 (d, J=5.6 Hz, 2H), 7.56-7.59 (d, J=10.4 Hz, 1H), 7.49-7.50 (d, J=5.2 Hz, 1H), 7.30-7.32 (d, J=8.4 Hz, 1H), 6.49-6.53 (t, J=8.8 Hz), 4.68 (s, 1H), 3.60 (m, 2H), 3.43 (m, 5H); m/z=504 [M+1]⁺, 442 [M-OCH₂CH₂OH]⁺, 427 [M-NHOCH₂CH₂OH]⁺.

Example 20

6-(2-Fluoro-4-(methylthio)phenylamino)-N-(2-hydroxyethoxy)-5-methyl-4-oxo-4,5-dihydrofuro[3,2-c]pyridine-7-carboxamide

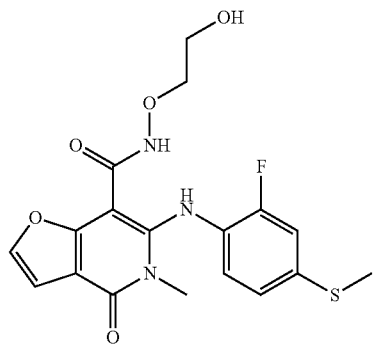

Following the same procedure as example 1 described, using 2-fluoro-N-((methylimino)methylene)-4-(methylthio)aniline as starting material to get the product. ¹H NMR (400 MHz, CDCl₃) δ 10.90 (s, 1H), 9.86 (s, 1H), 7.50 (d, J=2.0 Hz, 1H), 7.05-6.98 (m, 2H), 6.96 (d, J=2.0 Hz, 1H), 6.79 (t, J=8.4 Hz, 1H), 4.16-4.09 (m, 3H), 3.79-3.75 (m, 2H), 3.28 (s, 3H), 2.48 (s, 3H); m/z=331 [M-NHOCH₂CH₂OH]⁺, 408 [M+1]⁺.

Example 21

6-(2-Chloro-4-(methylthio)phenylamino)-N-(2-hydroxyethoxy)-5-methyl-4-oxo-4,5-dihydrofuro[3,2-c]pyridine-7-carboxamide

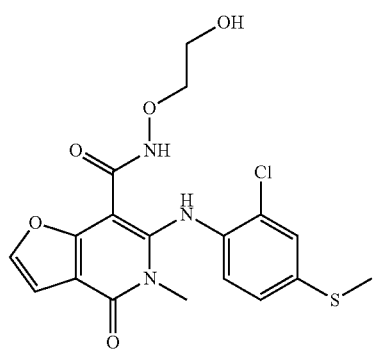 [SMILES: CSc1ccc(Nc2c(C(=O)NOCCO)c3occc3c(=O)n2C)c(F)c1]

Following the same procedure as example 1 described, using 2-chloro-N-((methylimino)methylene)-4-(methylthio)aniline as starting material to get the product. ¹H NMR (400 MHz, CDCl₃) δ 10.84 (s, 1H), 9.85 (s, 1H), 7.52 (d, J=2.4 Hz, 1H), 7.31 (d, J=2.4 Hz, 1H), 7.06 (d, J=6.0 Hz, 1H), 7.02-7.01 (m, 1H), 6.62 (d, J=8.4 Hz, 1H), 4.12-4.09 (m, 3H), 3.79-3.77 (m, 2H), 3.25 (s, 3H), 2.48 (s, 3H); m/z=347 [M-NHOCH₂CH₂OH]⁺, 424 [M+1]⁺.

Example 22

6-(2-Fluoro-4-iodophenylamino)-N-(2-hydroxy-ethoxy)-2,5-dimethyl-4-oxo-4,5-dihydrooxazolo[4,5-c]pyridine-7-carboxamide

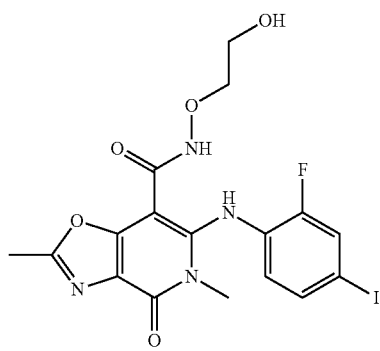 [SMILES: Cc1nc2c(=O)n(C)c(Nc3ccc(I)cc3F)c(C(=O)NOCCO)c2o1]

Step A: methyl 5-(2-methoxy-2-oxoethyl)-2-methyl-oxazole-4-carboxylate

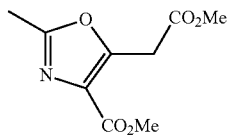

According to *J. Org. Chem.*, 1998, 63, 7680-7686., the title compound was made. $^1$H NMR (400 MHz, CDCl$_3$): δ 4.10 (s, 2H), 3.90 (s, 3H), 3.75 (s, 3H), 2.49 (s, 3H).

Step B: methyl 6-(2-fluoro-4-iodophenylamino)-2,5-dimethyl-4-oxo-4,5-dihydrooxazolo[4,5-c]pyridine-7-carboxylate

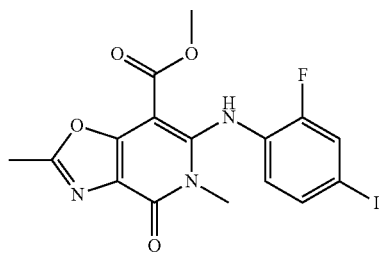

According to the procedure B, methyl 5-(2-methoxy-2-oxoethyl)-2-methyloxazole-4-carboxylate was reacted with 2-fluoro-4-iodo-N-((methylimino)methylene)aniline to obtain the desired product. $^1$H NMR (400 MHz, CDCl$_3$) δ 9.93 (s, 1H), 7.49-7.52 (dd, J=1.8 & 9.8 Hz, 1H), 7.38-7.41 (d, J=8.4 Hz, 1H), 6.48-6.52 (t, J=8.4 Hz, 1H), 3.96 (s, 3H), 3.36 (s, 3H), 2.64 (s, 3H).

Step C: 6-(2-fluoro-4-iodophenylamino)-2,5-dimethyl-4-oxo-4,5-dihydrooxazolo[4,5-c]pyridine-7-carboxylic acid

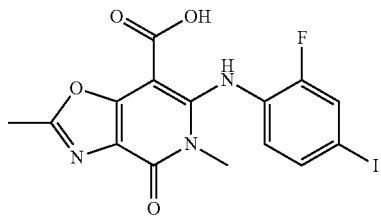

Following the same procedure as step C, example 1 described, the title product was obtained.

Step D: 6-(2-fluoro-4-iodophenylamino)-N-(2-hydroxyethoxy)-2,5-dimethyl-4-oxo-4,5-dihydrooxazolo[4,5-c]pyridine-7-carboxamide

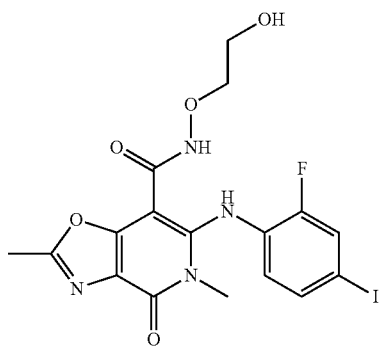 [SMILES: Cc1nc2c(=O)n(C)c(Nc3ccc(I)cc3F)c(C(=O)NOCCO)c2o1]

Following the same procedure as step D, example 1 described, the title product was obtained. $^1$H NMR (400 MHz, CDCl$_3$) δ 10.86 (s, 1H), 9.51 (s, 1H), 7.46 (d, J=8.0 Hz, 1H), 7.42 (d, J=8.8 Hz, 1H), 6.59 (t, J=8.4 Hz, 1H), 4.13-4.11 (m, 2H), 3.92-3.89 (m, 1H), 3.81-3.77 (m, 2H), 3.31 (s, 3H), 2.68 (s, 3H); m/z=503 [M+1]$^+$, 441 [M-OCH$_2$CH$_2$OH]$^+$, 426 [M-NHOCH$_2$CH$_2$OH]$^+$.

Example 23

6-(2-Fluoro-4-iodophenylamino)-N-(2-hydroxy-ethoxy)-3,5-dimethyl-4-oxo-4,5-dihydroisoxazolo[4,5-c]pyridine-7-carboxamide

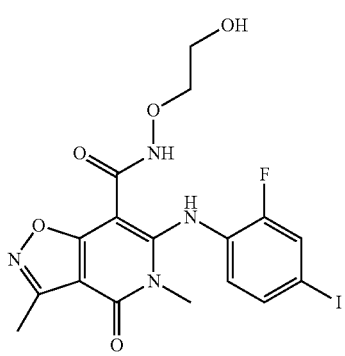 [SMILES: Cc1noc2c(C(=O)NOCCO)c(Nc3ccc(I)cc3F)n(C)c(=O)c12]

Step A: methyl 5-(2-methoxy-2-oxoethyl)-3-methyl-isoxazole-4-carboxylate

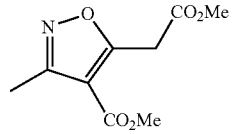

According to *J. Chem. Soc., Perkin Trans. 1, Organic and Bio-organic Chemistry,* 1999, 7, 765-776, the title compound was made. $^1$H NMR (400 MHz, CDCl$_3$): δ 4.13 (s, 2H), 3.86 (s, 3H), 3.75 (s, 3H), 2.47 (s, 3H).

Step B: methyl 6-(2-fluoro-4-iodophenylamino)-3,5-dimethyl-4-oxo-4,5-dihydroisoxazolo[4,5-c]pyridine-7-carboxylate

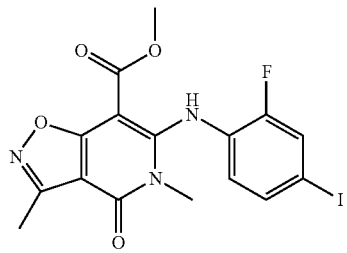 [SMILES: COC(=O)c1c(Nc2ccc(I)cc2F)n(C)c(=O)c2c(C)noc12]

According to the procedure B, methyl 5-(2-methoxy-2-oxoethyl)-3-methylisoxazole-4-carboxylate was reacted with 2-fluoro-4-iodo-N-((methylimino)methylene)aniline to obtain the desired product. $^1$H NMR (400 MHz, CDCl$_3$) δ 10.58 (s, 1H), 7.51-7.54 (dd, J=1.8 & 9.8 Hz, 1H), 7.44-7.46 (d, J=8.4 Hz, 1H), 6.63-6.67 (t, J=8.4 Hz, 1H), 3.98 (s, 3H), 3.23 (s, 3H), 2.60 (s, 3H).

Step C: 6-(2-fluoro-4-iodophenylamino)-3,5-dimethyl-4-oxo-N-(2-(vinyloxy)ethoxy)-4,5-dihydroisoxazolo[4,5-c]pyridine-7-carboxamide

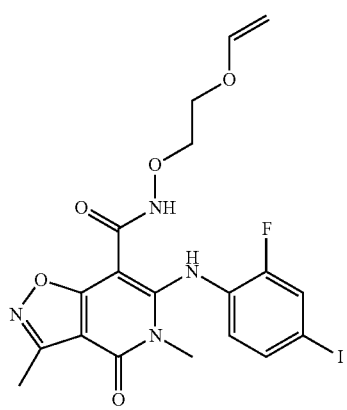 [SMILES: C=COCCONC(=O)c1c(Nc2ccc(I)cc2F)n(C)c(=O)c2c(C)noc12]

Following the same procedure as step C, example 19 described, the title product was obtained.

Step D: 6-(2-fluoro-4-iodophenylamino)-N-(2-hydroxyethoxy)-3,5-dimethyl-4-oxo-4,5-dihydroisoxazolo[4,5-c]pyridine-7-carboxamide

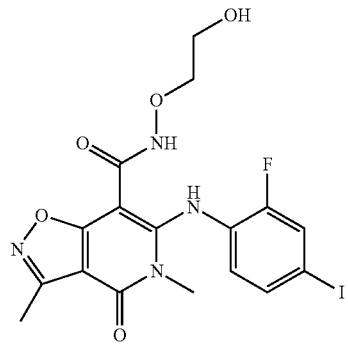 [SMILES: Cc1noc2c(C(=O)NOCCO)c(Nc3ccc(I)cc3F)n(C)c(=O)c12]

Following the same procedure as step D, example 19 described, the title product was obtained. $^1$H NMR (400 MHz, CDCl$_3$) δ 11.14 (s, 1H), 9.77 (s, 1H), 7.52 (d, J=9.6 Hz, 1H), 7.46 (d, J=8.4 Hz, 1H), 6.73 (t, J=8.0 Hz, 1H), 4.12-4.10 (m, 2H), 3.99-3.96 (m, 1H), 3.80-3.76 (m, 2H), 3.20 (s, 3H), 2.60 (s, 3H); m/z=426 [M-NHOCH$_2$CH$_2$OH]$^+$.

Example 24

6-(2-Fluoro-4-iodophenylamino)-N-(2-hydroxyethoxy)-3,5-dimethyl-4-oxo-4,5-dihydrofuro[3,2-c]pyridine-7-carboxamide

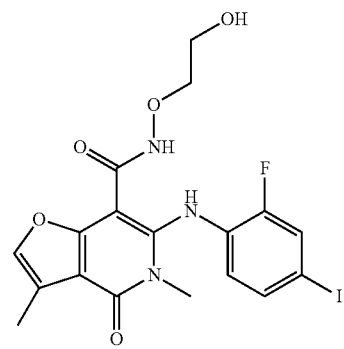 [SMILES: Cc1coc2c(C(=O)NOCCO)c(Nc3ccc(I)cc3F)n(C)c(=O)c12]

Step A: ethyl 2-(2-ethoxy-2-oxoethyl)-4-methyl-furan-3-carboxylate

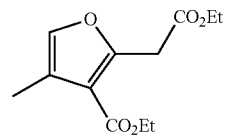

According to *J. Am. Chem. Soc,* 1985, 107, 2196-2198., the title compound was made. $^1$H NMR (400 MHz, CDCl$_3$) δ 7.13 (s, 1H), 4.28 (q, J=7.2 Hz, 2H), 4.18 (q, J=6.8 Hz, 2H), 4.01 (s, 2H), 2.17 (s, 3H), 1.34 (t, J=6.8 Hz, 3H), 1.26 (t, J=7.2 Hz, 3H).

Step B: ethyl 6-(2-fluoro-4-iodophenylamino)-3,5-dimethyl-4-oxo-4,5-dihydrofuro[3,2-c]pyridine-7-carboxylate

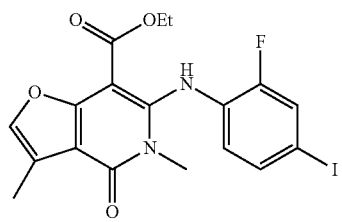 [SMILES: Cc1coc2c(C(=O)O)c(Nc3ccc(I)cc3F)n(C)c(=O)c12]

According to the procedure B, ethyl 2-(2-ethoxy-2-oxoethyl)-4-methylfuran-3-carboxylate was reacted with 2-fluoro-4-iodo-N-((methylimino)methylene)aniline to obtain the desired product. $^1$H NMR (400 MHz, CDCl$_3$) δ 9.77 (s, 1H), 7.48 (dd, J=1.6 & 9.6 Hz, 1H), 7.35 (d, J=8.4 Hz, 1H), 7.28 (q, J=1.2 Hz, 1H), 6.42 (t, J=8.4 Hz, 1H), 4.40 (q, J=7.2 Hz, 2H), 3.34 (s, 3H), 2.37 (d, J=1.2 Hz, 3H), 1.41 (t, J=7.2 Hz, 3H); m/z=471 [M+1]$^+$.

Step C: 6-(2-fluoro-4-iodophenylamino)-3,5-dimethyl-4-oxo-4,5-dihydrofuro[3,2-c]pyridine-7-carboxylic acid

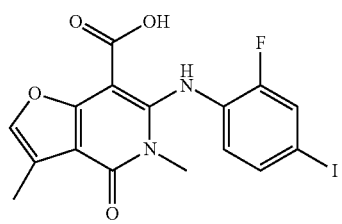

Following the same procedure as step C, example 1 described, the title product was obtained via column chromatography purification. $^1$H NMR (400 MHz, DMSO-D6) δ 13.20 (s, 1H), 9.63 (s, 1H), 7.64-7.71 (m, 2H), 7.40-7.42 (d, 1H), 6.60-6.70 (t, J=8.8 Hz, 1H), 3.23 (s, 3H), 2.25 (s, 3H); m/z=443 [M+1]$^+$.

Step D: 6-(2-fluoro-4-iodophenylamino)-N-(2-hydroxyethoxy)-3,5-dimethyl-4-oxo-4,5-dihydrofuro[3,2-c]pyridine-7-carboxamide

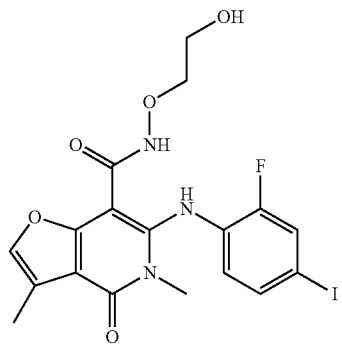 [SMILES: Cc1coc2c(C(=O)NOCCO)c(Nc3ccc(I)cc3F)n(C)c(=O)c12]

Following the same procedure as step D, example 1 described, the title product was obtained. $^1$H NMR (400 MHz, CDCl$_3$) δ 10.78 (s, 1H), 9.86 (s, 1H), 7.47-7.49 (dd, J=1.6 & 9.6 Hz, 1H), 7.37-7.39 (d, J=8.4 Hz, 1H), 7.37 (s, 1H), 6.51-6.55 (t, J=8.4 Hz, 1H), 4.08-4.10 (m, 2H), 3.74-3.78 (m, 2H), 3.28 (s, 3H), 2.37 (s, 3H); m/z=425 [M-NHOCH$_2$CH$_2$OH]$^+$, 502 [M+1]$^+$.

Example 25

6-(2-Fluoro-4-iodophenylamino)-N-(2-hydroxyethoxy)-5-methyl-4-oxo-4,5-dihydrothiazolo[4,5-c]pyridine-7-carboxamide

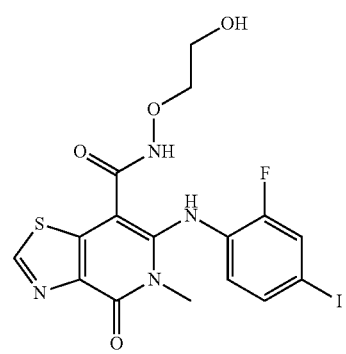 [SMILES: Cn1c(Nc2ccc(I)cc2F)c(C(=O)NOCCO)c2scnc2c1=O]

Step A: methyl 5-(2-methoxy-2-oxoethyl)thiazole-4-carboxylate

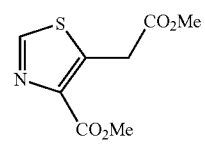 [SMILES: COC(=O)Cc1scnc1C(=O)OC]

According to *Bioorganic & Medicinal Chemistry Letters*, 2008, 18(6), 2206-2210., the title compound was made. $^1$H NMR (400 MHz, CDCl$_3$): δ 8.75 (s, 1H), 4.38 (s, 2H), 3.96 (s, 3H), 3.78 (s, 3H).

Step B: methyl 6-(2-fluoro-4-iodophenylamino)-5-methyl-4-oxo-4,5-dihydrothiazolo[4,5-c]pyridine-7-carboxylate

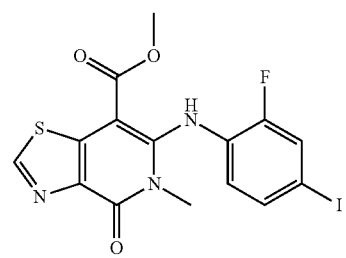

According to the procedure B, methyl 5-(2-methoxy-2-oxoethyl)thiazole-4-carboxylate was reacted with 2-fluoro-4-iodo-N-((methylimino)methylene)aniline to obtain the impure product. m/z=460 [M+1]+.

Step C: 6-(2-fluoro-4-iodophenylamino)-5-methyl-4-oxo-4,5-dihydrothiazolo[4,5-c]pyridine-7-carboxylic acid

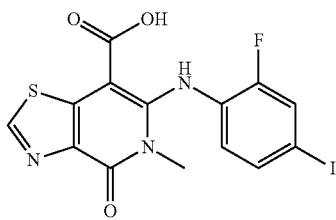 [SMILES: Cn1c(Nc2ccc(I)cc2F)c(C(=O)O)c2scnc2c1=O]

Following the same procedure as step C, example 1 described, the title product was obtained via column chromatography purification.

Step D: 6-(2-fluoro-4-iodophenylamino)-N-(2-hydroxyethoxy)-5-methyl-4-oxo-4,5-dihydrothiazolo[4,5-c]pyridine-7-carboxamide

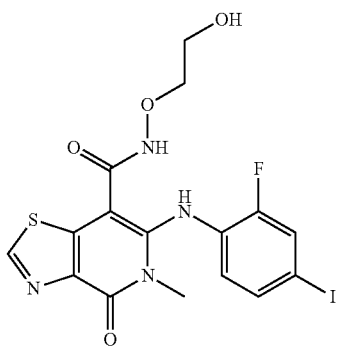 [SMILES: Cn1c(Nc2ccc(I)cc2F)c(C(=O)NOCCO)c2scnc2c1=O]

Following the same procedure as step D, example 1 described, the title product was obtained. $^1$H NMR (400 MHz, CD$_3$OD) δ 9.05 (s, 1H), 7.53-7.56 (dd, J=1.8 & 10.6 Hz, 1H), 7.38-7.40 (d, J=8.4 Hz, 1H), 6.61 (s, 1H), 3.59-3.71 (m, 7H); m/z=505 [M+1]$^+$, 443 [M-OCH$_2$CH$_2$OH]$^+$.

Example 26

6-(2-Fluoro-4-iodophenylamino)-N-(2-hydroxyethoxy)-2,5-dimethyl-4-oxo-4,5-dihydrothiazolo[4,5-c]pyridine-7-carboxamide

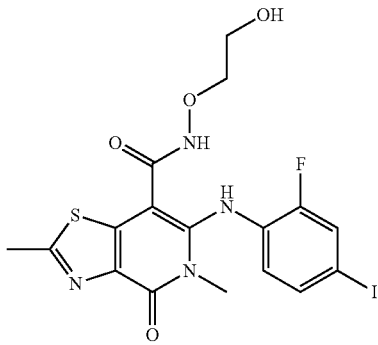

Step A: methyl 5-(2-methoxy-2-oxoethyl)-2-methylthiazole-4-carboxylate

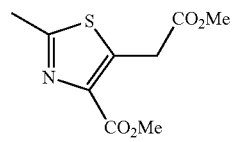

According to *Heterocycles*, 1998, 48(5), 853-860., the title compound was made. $^1$H NMR (400 MHz, CDCl$_3$): δ 4.30 (s, 2H), 3.94 (s, 3H), 3.76 (s, 3H), 2.72 (s, 3H).

Step B: methyl 6-(2-fluoro-4-iodophenylamino)-2,5-dimethyl-4-oxo-4,5-dihydrothiazolo[4,5-c]pyridine-7-carboxylate

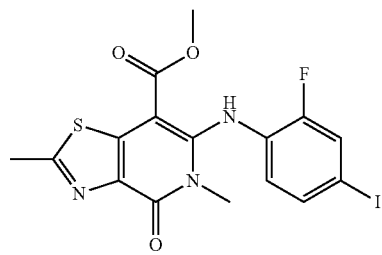

According to the procedure B, methyl 5-(2-methoxy-2-oxoethyl)-2-methylthiazole-4-carboxylate was reacted with 2-fluoro-4-iodo-N-((methylimino)methylene)aniline to obtain the impure product. m/z=474 [M+1]$^+$.

Step C: 6-(2-fluoro-4-iodophenylamino)-2,5-dimethyl-4-oxo-4,5-dihydrothiazolo[4,5-c]pyridine-7-carboxylic acid

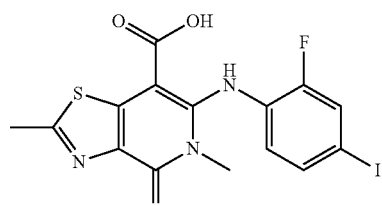

Following the same procedure as step C, example 1 described, the title product was obtained via column chromatography purification. $^1$H NMR (400 MHz, DMSO-D6) δ 13.20 (s, 1H), 9.63 (s, 1H), 7.68 (dd, J=1.6 Hz & 10.4 Hz, 1H), 7.42 (d, J=8.4 Hz, 1H), 6.68 (t, J=8.4 Hz, 1H), 3.23 (s, 3H), 2.26 (s, 3H).

Step D: 6-(2-fluoro-4-iodophenylamino)-N-(2-hydroxyethoxy)-2,5-dimethyl-4-oxo-4,5-dihydrothiazolo[4,5-c]pyridine-7-carboxamide

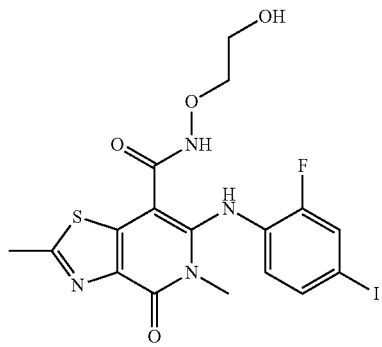

Following the same procedure as step D, example 1 described, the title product was obtained. $^1$H NMR (400 MHz, CD$_3$OD) 7.54-7.57 (d, J=10.4 Hz, 1H), 7.42-7.45 (d, J=9.2 Hz, 1H), 6.57 (t, J=8.4 Hz, 1H), 3.30-3.37 (m, 7H), 2.72-2.79 (m, 3H); m/z=519 [M+1]$^+$.

Example 27

(R)—N-(2,3-Dihydroxypropoxy)-6-(2-fluoro-4-iodophenylamino)-2,5-dimethyl-4-oxo-4,5-dihydrofuro[3,2-c]pyridine-7-carboxamide

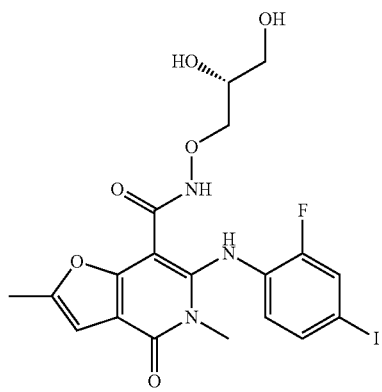 [SMILES: Cc1cc2c(=O)n(C)c(Nc3ccc(I)cc3F)c(C(=O)NOC[C@H](O)CO)c2o1]

According to procedure C, 6-(2-fluoro-4-iodophenylamino)-2,5-dimethyl-4-oxo-4,5-dihydrofuro[3,2-c]pyridine-7-carboxylic acid was coupling with (R)—O-((2,2-dimethyl-1,3-dioxolan-4-yl)methyl)hydroxylamine (made according to *Tetrahedron Letters*, 2006, 47, 7607-7609), followed by treating with 2 N HCl in MeOH to get the title product. $^1$H NMR (400 MHz, CDCl$_3$) δ 10.63 (s, 1H), 9.98 (s, 1H), 7.39-7.51 (dd, J=1.8 Hz & 9.8 Hz, 1H), 7.37-7.39 (d, J=8.4 Hz, 1H), 6.58 (s, 1H), 6.48-6.53 (t, J=8.4 Hz, 1H), 4.42-4.43 (d, J=3.6 Hz, 1H), 4.04-4.15 (m, 2H), 3.97-3.99 (t, J=3.8 Hz, 1H), 3.74-3.78 (m, 1H), 3.64-3.68 (m, 1H), 3.30 (s, 3H), 2.48 (s, 3H), 2.37-2.40 (t, J=6.2 Hz, 1H); m/z=532 [M+1]$^+$, 425 [M-NHOCH$_2$CH(OH)CH$_2$OH]$^+$.

Example 28

2-((Dimethylamino)methyl)-6-(2-fluoro-4-iodophenylamino)-N-(2-hydroxyethoxy)-5-methyl-4-oxo-4,5-dihydrofuro[3,2-c]pyridine-7-carboxamide

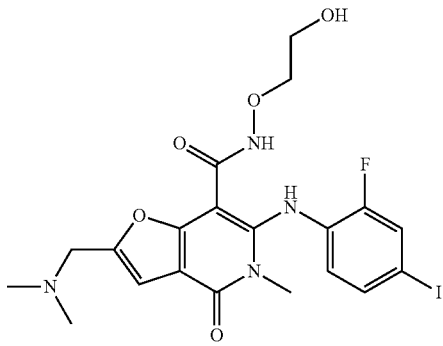 [SMILES: CN(C)Cc1cc2c(=O)n(C)c(Nc3ccc(I)cc3F)c(C(=O)NOCCO)c2o1]

Step A: methyl 2-((dimethylamino)methyl)-6-(2-fluoro-4-iodophenylamino)-5-methyl-4-oxo-4,5-dihydrofuro[3,2-c]pyridine-7-carboxylate

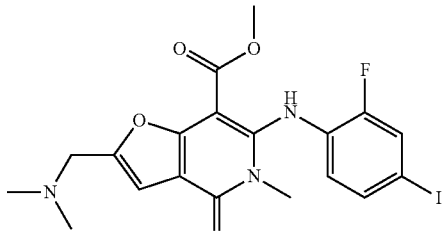

Dimethylamine (178 mg, 0.2 mL, 33% aq., 1.30 mmol) was added to acetic acid (1 mL) slowly at 0° C., then 37% aqueous formaldehyde (formalin) solution (0.1 mL, 1.33 mmol) was added at 0° C. The mixture was then stirred at r.t., and methyl 6-(2-fluoro-4-iodophenylamino)-5-methyl-4-oxo-4,5-dihydrofuro[3,2-c]pyridine-7-carboxylate (300 mg, 0.68 mmol) was added at once. After addition of 20 mL THF, the mixture was heated to reflux. After consuming up of the methyl ester, water was added. Using CH$_2$Cl$_2$ extracted, dried, filtered, concentrated the filtrate in vacuum, the residue was purified by flash column chromatography on silica gel to get the title product (255 mg, 75%). $^1$H NMR (400 MHz, CDCl$_3$) δ 9.77 (s, 1H), 7.49 (dd, J=2.0 & 10.0 Hz, 1H), 7.37 (d, J=8.8 Hz, 1H), 6.76 (s, 1H), 6.44 (t, J=8.8 Hz, 1H), 3.94 (s, 3H), 3.63 (s, 2H), 3.36 (s, 3H), 2.35 (s, 6H); m/z=455 [M-N(CH$_3$)$_2$]$^+$.

Step B: 2-((dimethylamino)methyl)-6-(2-fluoro-4-iodophenylamino)-5-methyl-4-oxo-4,5-dihydrofuo[3,2-c]pyridine-7-carboxylic acid

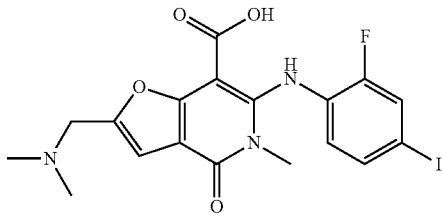 [SMILES: CN(C)Cc1cc2c(=O)n(C)c(Nc3ccc(I)cc3F)c(C(=O)O)c2o1]

A mixture of methyl 2-((dimethylamino)methyl)-6-(2-fluoro-4-iodophenylamino)-5-methyl-4-oxo-4,5-dihydrofuro[3,2-c]pyridine-7-carboxylate (200 mg, 0.4 mmol) and K₂CO₃ (166 mg, 1.2 mmol) in 12 mL MeOH:H₂O (5:1) was heated at 70° C. for 2 h, the mixture was then concentrated in vacuum, the residue was then purified by flash column chromatography on silica gel (CH₂Cl₂:MeOH=10:1 to MeOH) to get the title product (180 mg, 93%). $^1$H NMR (400 MHz, DMSO-D6) δ 7.65 (dd, J=2.0 & 10.8 Hz, 1H), 7.39 (d, J=8.4 Hz, 1H), 6.75 (s, 1H), 6.55 (t, J=8.4 Hz, 1H), 3.65 (s, 2H), 3.21 (s, 3H), 2.28 (s, 6H); m/z=441 [M-N(CH₃)₂]⁺.

Step C: 2-((dimethylamino)methyl)-6-(2-fluoro-4-iodophenylamino)-N-(2-hydroxy ethoxy)-5-methyl-4-oxo-4,5-dihydrofuro[3,2-c]pyridine-7-carboxamide

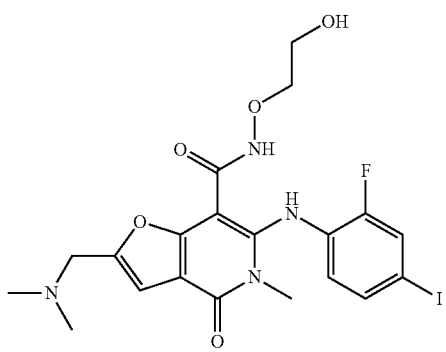 [SMILES: CN(C)Cc1cc2c(=O)n(C)c(Nc3ccc(I)cc3F)c(C(=O)NOCCO)c2o1]

Following the same procedure as step D, example 1 described, the title product was obtained. $^1$H NMR (400 MHz, CDCl₃) δ 10.77 (s, 1H), 10.69 (s, 1H), 7.46-7.49 (dd, J=1.8 & 9.8 Hz, 1H), 7.36-7.38 (d, J=8.4 Hz, 1H), 6.80 (s, 1H), 6.48-6.52 (t, J=8.4 Hz, 1H), 4.11-4.13 (m, 2H), 3.82-3.84 (m, 2H), 3.58 (s, 2H), 3.31 (s, 3H), 2.33 (s, 6H); m/z=500 [M-N(CH₃)₂]⁺, 438 [M-N(CH₃)₂—OCH₂CH₂OH]⁺.

Example 29

6-(2-Fluoro-4-iodophenylamino)-N-(2-hydroxyethoxy)-5-methyl-2-(morpholinomethyl)-4-oxo-4,5-dihydrofuro[3,2-c]pyridine-7-carboxamide

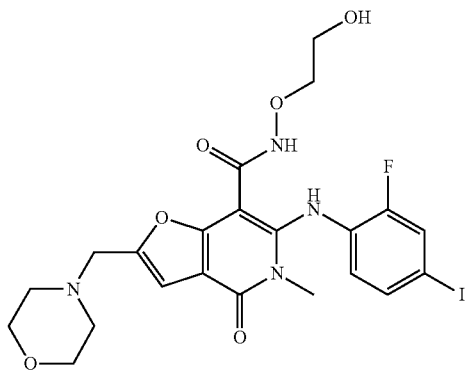 [SMILES: Cn1c(Nc2ccc(I)cc2F)c(C(=O)NOCCO)c2oc(CN3CCOCC3)cc2c1=O]

Step A: methyl 6-(2-fluoro-4-iodophenylamino)-5-methyl-2-(morpholinomethyl)-4-oxo-4,5-dihydrofuro[3,2-c]pyridine-7-carboxylate

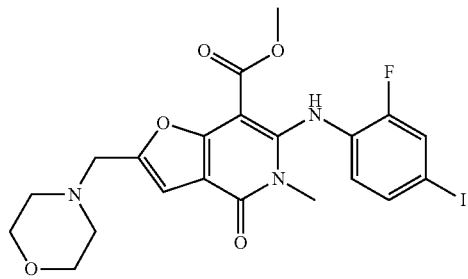 [SMILES: COC(=O)c1c(Nc2ccc(I)cc2F)n(C)c(=O)c2cc(CN3CCOCC3)oc12]

Following the same procedure as step A, example 28 described, using morpholine (1.5 eq.) instead of dimethylamine, the title product was obtained. $^1$H NMR (400 MHz, CDCl₃): δ 9.76 (s, 1H), 7.49 (dd, J=2.0 & 10.0 Hz, 1H), 7.37 (d, J=8.4 Hz, 1H), 6.77 (s, 1H), 6.44 (t, J=8.4 Hz, 1H), 3.94 (s, 3H), 3.60-3.75 (m, 6H), 3.35 (s, 3H), 2.58-2.64 (m, 4H); m/z=455 [M-N(CH₂CH₂OCH₂CH₂)]⁺, 564 [M+Na]⁺.

Step B: 6-(2-fluoro-4-iodophenylamino)-5-methyl-2-(morpholinomethyl)-4-oxo-4,5-dihydrofuro[3,2-c]pyridine-7-carboxylic acid

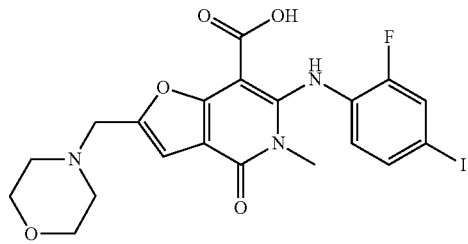 [SMILES: Cn1c(Nc2ccc(I)cc2F)c(C(=O)O)c2oc(CN3CCOCC3)cc2c1=O]

Following the same procedure as step B, example 28 described, the title product was obtained. $^1$H NMR (400 MHz, DMSO-D6) δ 7.65 (dd, J=2.0 Hz & 10.8 Hz, 1H), 7.39 (dd, J=1.2 & 8.4 Hz, 1H), 6.72 (s, 1H), 6.53 (t, J=8.4 Hz, 1H), 3.56-3.58 (m, 6H), 3.21 (s, 3H), 2.43 (m, 4H); m/z=441 [M-N(CH₂CH₂OCH₂CH₂)]⁺.

Step C: 6-(2-fluoro-4-iodophenylamino)-N-(2-hydroxyethoxy)-5-methyl-2-(morpholinomethyl)-4-oxo-4,5-dihydrofuro[3,2-c]pyridine-7-carboxamide

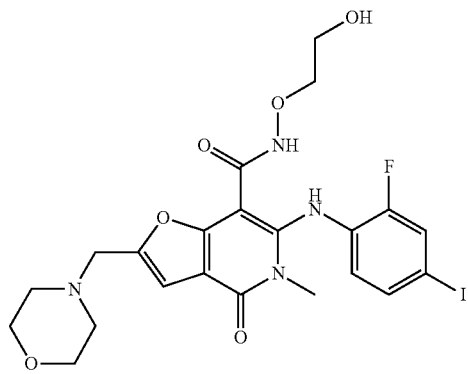 [SMILES: Cn1c(Nc2ccc(I)cc2F)c(C(=O)NOCCO)c2oc(CN3CCOCC3)cc2c1=O]

Following the same procedure as step D, example 1 described, the title product was obtained. $^1$H NMR (400 MHz, CDCl$_3$) δ 10.78 (s, 1H), 10.28 (s, 1H), 7.47-7.50 (dd, J=2. & 10.6 Hz, 1H), 7.37-7.39 (d, J=8.4 Hz, 1H), 6.82 (s, 1H), 6.50-6.54 (t, J=8.4 Hz, 1H), 4.11-4.13 (m, 2H), 3.82-3.84 (m, 2H), 3.73-3.75 (t, J=4.4 Hz, 4H), 3.73 (s, 2H), 3.30 (s, 3H), 2.54 (s, 4H); m/z=500 [M-N(CH$_2$CH$_2$OCH$_2$CH$_2$)]$^+$, 438 [M-N(CH$_2$CH$_2$OCH$_2$CH$_2$)—OCH$_2$CH$_2$OH]$^+$.

Example 30

6-(2-Fluoro-4-iodophenylamino)-N-(2-hydroxyacetyl)-5-methyl-4-oxo-4,5-dihydrofuro[3,2-c]pyridine-7-carboxamide

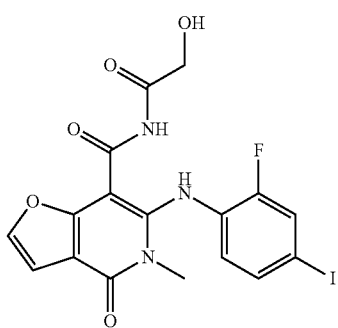 [SMILES: Cn1c(Nc2ccc(I)cc2F)c(C(=O)NC(=O)CO)c2occc2c1=O]

Step A: 2-(tert-butyldimethylsilyloxy)acetyl chloride

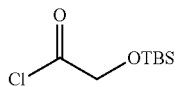

The title compound was made according to *J. Org. Chem.*, 1988, 53, 3457-3465. $^1$H NMR (400 MHz, CDCl$_3$): δ 4.54 (s, 2H), 0.91 (s, 9H), 0.12 (s, 6H).

Step B: N-(2-(tert-butyldimethylsilyloxy)acetyl)-6-(2-fluoro-4-iodophenylamino)-5-methyl-4-oxo-4,5-dihydrofuro[3,2-c]pyridine-7-carboxamide

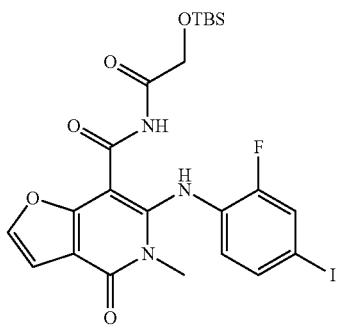 [SMILES: Cn1c(Nc2ccc(I)cc2F)c(C(=O)NC(=O)CO[Si](C)(C)C(C)(C)C)c2occc2c1=O]

To a stirred solution of 6-(2-fluoro-4-iodophenylamino)-5-methyl-4-oxo-4,5-dihydrofuro[3,2-c]pyridine-7-carboxamide (1.0 eq.) in anhydrous THF was added NaH (1.1 eq., 60%) portionwise at 0° C., the mixture was then stirred at room temperature for 1 h, then 2-(tert-butyldimethylsilyloxy)acetyl chloride (1.5 eq.) in THF was added slowly with dropping funnel, the mixture was then stirred at room temperature for 3 days. After the addition of water and ethyl acetate, the water layer was extracted with ethyl acetate, washed with sat. NaCl, dried over MgSO$_4$, filtered, concentrated in vacuum, the residue was purified by column chromatography on silica gel to get the desired product. $^1$H NMR (400 MHz, CDCl$_3$) δ 11.24 (s, 1H), 10.88 (s, 1H), 7.53 (d, J=2.4 Hz, 1H), 7.49 (dd, J=1.6 & 10.0 Hz, 1H), 7.42 (d, J=8.4 Hz, 1H), 7.03 (d, J=2.4 Hz, 1H), 6.61 (t, J=8.4 Hz, 1H), 4.34 (s, 2H), 3.29 (s, 3H), 0.97 (s, 9H), 0.20 (s, 6H); m/z=600 [M+1]$^+$.

Step C: 6-(2-fluoro-4-iodophenylamino)-N-(2-hydroxyacetyl)-5-methyl-4-oxo-4,5-dihydrofuro[3,2-c]pyridine-7-carboxamide

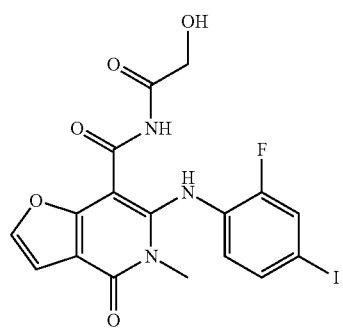 [SMILES: Cn1c(Nc2ccc(I)cc2F)c(C(=O)NC(=O)CO)c2occc2c1=O]

To a solution of N-(2-(tert-butyldimethylsilyloxy)acetyl)-6-(2-fluoro-4-iodophenyl amino)-5-methyl-4-oxo-4,5-dihydrofuro[3,2-c]pyridine-7-carboxamide (30 mg, 0.05 mmol) in MeOH (5 mL) was added 2N HCl (1 mL). The mixture was then stirred at room temperature for 5 min. The white precipitate was filtered, dried, afforded the title compound (6.7 mg, 28%). $^1$H NMR (400 MHz, DMSO-D6) δ 10.83 (s, 1H), 9.21 (s, 1H), 7.92 (d, J=2.4 Hz, 1H), 7.63 (dd, J=2.0 & 10.8 Hz, 1H), 7.37 (d, J=8.4 Hz, 1H), 7.01 (d, J=2.0 Hz, 1H), 6.68 (t, J=8.8 Hz, 1H), 5.45 (t, J=6.0 Hz, 1H), 4.06 (t, J=6.0 Hz, 2H), 3.35 (s, 3H); m/z=486 [M+1]$^+$.

Example 31

2-Amino-6-(2-fluoro-4-iodophenylamino)-N-(2-hydroxyethoxy)-5-methyl-4-oxo-4,5-dihydrothiazolo[5,4-c]pyridine-7-carboxamide

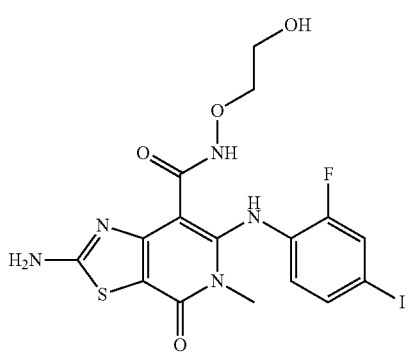 [SMILES: Cn1c(Nc2ccc(I)cc2F)c(C(=O)NOCCO)c2nc(N)sc2c1=O]

Step A: ethyl 2-amino-4-(2-ethoxy-2-oxoethyl)thiazole-5-carboxylate

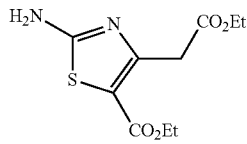

To a neat diethyl 3-oxopentanedioate (20.2 g, 0.10 mol) was added sulfurous dichloride (13.5 g, 0.11 mol) dropwise at 0° C., the mixture was then stirred at rt for 1 h followed by heated at 50° C. for 0.5 h. The resulting solution was added dropwise to a solution of thiourea (7.6 g, 1.0 mol) in EtOH (50 mL). The mixture was reflux for 0.5 h and added into ice water then alkaline with aq. $Na_2CO_3$, the precipitate was filtered off and dried to afford the title compound (16 g, 62%). $^1$H NMR (400 MHz, $CDCl_3$) δ 6.01 (brs, 2H), 4.27 (q, J=7.2 Hz, 2H), 4.17 (q, J=7.2 Hz, 2H), 4.03 (s, 2H), 1.34 (t, J=7.2 Hz, 3H), 1.26 (t, J=7.2 Hz, 3H).

Step B: ethyl 2-(bis(tert-butoxycarbonyl)amino)-4-(2-ethoxy-2-oxoethyl)thiazole-5-carboxylate

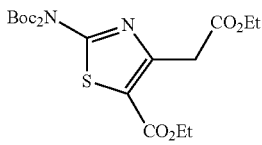

To a solution of ethyl 2-amino-4-(2-ethoxy-2-oxoethyl)thiazole-5-carboxylate (4.0 g, 15.5 mmol) and $(Boc)_2O$ (13.5 g, 61.9 mmol) in THF (50 mL) was added $Et_3N$ (9.4 mL, 61.9 mmol) and DMAP (190 mg, 1.55 mmol) at rt, the mixture was then heated under reflux overnight. After quenching with water, the mixture was partitioned between dichloromethane and saturated NaCl. The organic layers was separated, dried, concentrated under reduced pressure, residue was purified by column chromatography on silica gel (petroleum ether:EtOAc=2:1) to obtain the titled compound (1.2 g, 17%) and ethyl 2-(tert-butoxycarbonylamino)-4-(2-ethoxy-2-oxoethyl)thiazole-5-carboxylate (1.0 g, 18%). $^1$H NMR (400 MHz, $CDCl_3$) δ 4.32 (q, J=7.2 Hz, 2H), 4.19 (s, 2H), 4.16 (q, J=7.2 Hz, 2H), 1.44 (s, 9H), 1.39 (s, 9H), 1.36 (t, J=7.2 Hz, 3H), 1.24 (t, J=7.2 Hz, 3H).

Step C: ethyl 2-(bis(tert-butoxycarbonyl)amino)-6-(2-fluoro-4-iodophenylamino)-5-methyl-4-oxo-4,5-dihydrothiazolo[5,4-c]pyridine-7-carboxylate

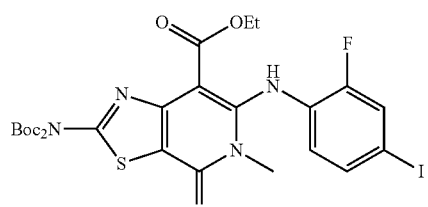

According to the procedure B, ethyl 2-(bis(tert-butoxycarbonyl)amino)-4-(2-ethoxy-2-oxoethyl)thiazole-5-carboxylate was reacted with 2-fluoro-4-iodo-N-((methylimino)methylene)aniline to obtain the desired product via column chromatography purification. $^1$H NMR (400 MHz, $CDCl_3$) δ 9.49 (s, 1H), 7.48-7.51 (dd, J=9.8 & 1.8 Hz, 1H), 7.35-7.37 (d, J=8.4 Hz, 1H), 6.42-6.46 (t, J=8.4 Hz, 1H), 4.37 (q, J=7.2 Hz, 2H), 3.42 (s, 3H), 1.54 (s, 9H), 1.43 (s, 9H), 1.38 (t, J=7.2 Hz, 3H).

Step D: 2-(bis(tert-butoxycarbonyl)amino)-6-(2-fluoro-4-iodophenylamino)-5-methyl-4-oxo-4,5-dihydrothiazolo[5,4-c]pyridine-7-carboxylic acid

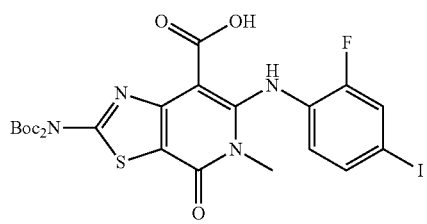

Following the same procedure as step C, example 1 described, the title product was obtained via column chromatography purification.

Step E: 2-(bis(tert-butoxycarbonyl)amino)-6-(2-fluoro-4-iodophenylamino)-5-methyl-4-oxo-N-(2-(vinyloxy)ethoxy)-4,5-dihydrothiazolo[5,4-c]pyridine-7-carboxamide

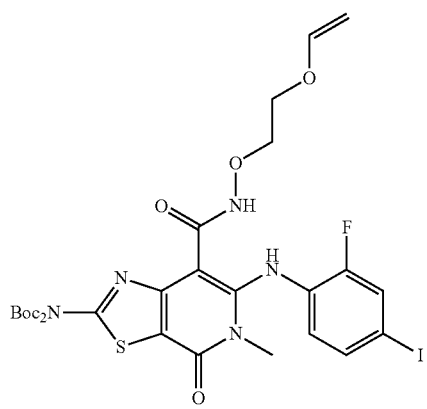

Following the same procedure (coupling section) as step D, example 1 described, the title product was obtained via column chromatography purification. $^1$H NMR (400 MHz, $CDCl_3$) δ 12.05 (s, 1H), 11.45 (s, 1H), 7.47-7.52 (dd, J=10.0 & 2.0 Hz, 1H), 7.37-7.39 (d, J=8.4 Hz, 1H), 6.55 (t, J=8.4 Hz, 1H), 6.50 (dd, J=14.0 & 6.8 Hz, 1H), 4.27-4.29 (m, 2H), 4.20 (dd, J=14.4 & 2.4 Hz, 1H), 4.04 (dd, J=6.8 & 2.4 Hz, 1H), 3.96-3.99 (m, 2H), 3.35 (s, 3H), 1.50 (s, 9H), 1.43 (s, 9H).

Step F: 2-amino-6-(2-fluoro-4-iodophenylamino)-N-(2-hydroxyethoxy)-5-methyl-4-oxo-4,5-dihydrothiazolo[5,4-c]pyridine-7-carboxamide

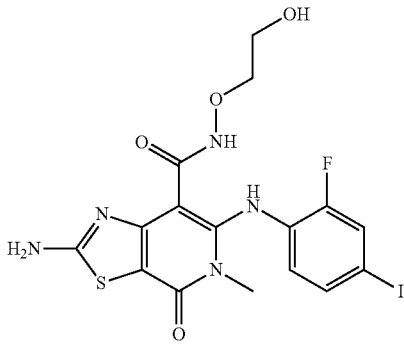 [SMILES: Cn1c(Nc2ccc(I)cc2F)c(C(=O)NOCCO)c2nc(N)sc2c1=O]

Following the same procedure as step D, example 1 described, after treating with 2 N HCl in MeOH, the solution was concentrated in vacuum, the residue was then dissolved in dichloromethane/trifluoroacetic acid solution (v/v, 1/1) and stirred for 1 h, then concentrated under reduced pressure, the residue was purified by column chromatography on silica gel to afford the title product. $^1$H NMR (400 MHz, DMSO-D6) δ 12.24 (s, 1H), 10.56 (s, 1H), 8.43 (s, 2H), 7.68 (dd, J=10.4 & 2.0 Hz, 1H), 7.42 (d, J=7.6 Hz, 1H), 6.65 (t, J=8.4 Hz, 1H), 4.71 (t, J=5.6 Hz, 1H), 3.84 (t, J=4.8 Hz, 1H), 3.53-3.57 (m, 2H), 3.20 (s, 3H); m/z=520 [M+1]$^+$.

Example 32

6-(2-Fluoro-4-iodophenylamino)-N-(2-hydroxyethoxy)-5-methyl-2-(methylamino)-4-oxo-4,5-dihydrothiazolo[5,4-c]pyridine-7-carboxamide

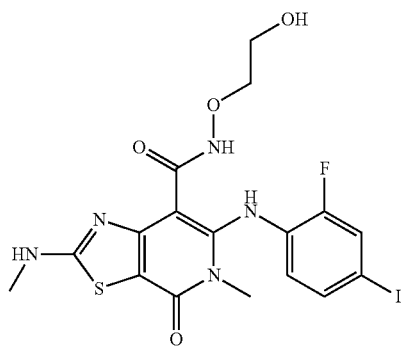 [SMILES: CNc1nc2c(C(=O)NOCCO)c(Nc3ccc(I)cc3F)n(C)c(=O)c2s1]

Step A: ethyl 2-(tert-butoxycarbonylamino)-4-(2-ethoxy-2-oxoethyl)thiazole-5-carboxylate

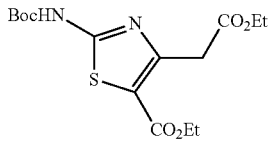

According to the same procedure as Step B, Example 31 described, the title compound was obtained. $^1$H NMR (400 MHz, DMSO-D6) δ 11.99 (brs, 1H), 4.22 (q, J=7.2 Hz, 2H), 4.07 (q, J=7.2 Hz, 2H), 4.00 (s, 2H), 1.49 (s, 9H), 1.26 (t, J=7.2 Hz, 3H), 1.17 (t, J=7.2 Hz, 3H).

Step B: ethyl 2-(tert-butoxycarbonyl(methyl)amino)-4-(2-ethoxy-2-oxoethyl)thiazole-5-carboxylate

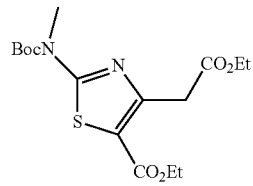 [SMILES: CCOC(=O)Cc1nc(N(C)C(=O)OC(C)(C)C)sc1C(=O)OCC]

To a solution of ethyl 2-(tert-butoxycarbonylamino)-4-(2-ethoxy-2-oxoethyl)thiazole-5-carboxylate (50 mg, 1.0 eq.) in acetone (5 ml) was added MeI (23.8 mg, 1.2 eq.) and K$_2$CO$_3$ (19.2 mg, 1.0 eq.) at 0° C. The mixture was warmed to room temperature and stirred for 3.5 h at this temperature. The solvent was removed under reduced pressure and the residue was purified by column chromatography on silica gel (EtOAc/petroleum ether=1/20) to obtain the titled compound (50 mg, yield=98%). $^1$H NMR (400 MHz, CDCl$_3$) δ 4.28 (q, J=7.2 Hz, 2H), 4.18 (q, J=7.2 Hz, 2H), 4.11 (s, 2H), 3.53 (s, 3H), 1.58 (s, 9H), 1.33 (t, J=7.2 Hz, 3H), 1.26 (t, J=7.2 Hz, 3H).

Step C: ethyl 2-(tert-butoxycarbonyl(methyl)amino)-6-(2-fluoro-4-iodophenylamino)-5-methyl-4-oxo-4,5-dihydrothiazolo[5,4-c]pyridine-7-carboxylate

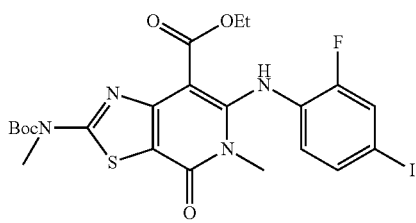 [SMILES: CCOC(=O)c1c(Nc2ccc(I)cc2F)n(C)c(=O)c2sc(N(C)C(=O)OC(C)(C)C)nc12]

According to the procedure B, ethyl 2-(tert-butoxycarbonyl(methyl)amino)-4-(2-ethoxy-2-oxoethyl)thiazole-5-carboxylate was reacted with 2-fluoro-4-iodo-N-((methylimino)methylene)aniline to obtain the desired product. $^1$H NMR (400 MHz, CDCl$_3$) δ 9.48 (s, 1H), 7.48 (dd, J=10.0 & 2.0 Hz, 1H), 7.34 (d, J=8.4 Hz, 1H), 6.39 (t, J=8.4 Hz, 1H), 4.37 (q, J=7.2 Hz, 2H), 3.65 (s, 3H), 3.41 (s, 3H), 1.56 (s, 9H), 1.41 (t, J=7.2 Hz, 3H).

Step D: 2-(tert-butoxycarbonyl(methyl)amino)-6-(2-fluoro-4-iodophenylamino)-5-methyl-4-oxo-4,5-dihydrothiazolo[5,4-c]pyridine-7-carboxylic acid

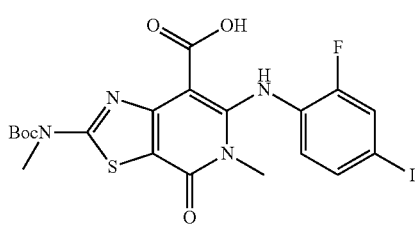 [SMILES: CN(C(=O)OC(C)(C)C)c1nc2c(C(=O)O)c(Nc3ccc(I)cc3F)n(C)c(=O)c2s1]

Following the same procedure as step C, example 1 described, the title product was obtained. $^1$H NMR (400

MHz, DMSO-D6) δ 10.36 (brs, 1H), 9.28 (brs, 1H), 7.74 (d, J=10.4 Hz, 1H), 7.49 (d, J=8.0 Hz, 1H), 6.85 (t, J=8.8 Hz, 1H), 3.15 (s, 3H), 2.99 (s, 3H).

Step E: 6-(2-fluoro-4-iodophenylamino)-N-(2-hydroxyethoxy)-5-methyl-2-(methylamino)-4-oxo-4,5-dihydrothiazolo[5,4-c]pyridine-7-carboxamide

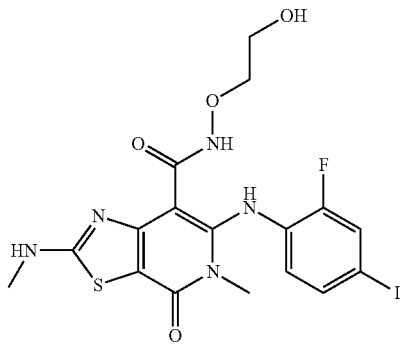 [SMILES: CNc1nc2c(C(=O)NOCCO)c(Nc3ccc(I)cc3F)n(C)c(=O)c2s1]

Following the same procedure as step D, example 1 described, the title product was obtained. ¹H NMR (400 MHz, CD₃OD) δ 7.40 (dd, J=10.8 & 2.0 Hz, 1H), 7.27 (d, J=8.4 Hz, 1H), 6.35 (t, J=8.8 Hz, 1H), 3.81-3.83 (m, 2H), 3.59-3.61 (m, 2H), 3.31 (s, 3H), 2.95 (s, 3H); m/z=534 [M+1]⁺, 457 [M-NHOCH₂CH₂OH]⁺, 556 [M+Na]⁺.

Example 33

6-(2-Fluoro-4-iodophenylamino)-N-(2-hydroxyethoxy)-5-methyl-4-oxo-4,5-dihydrothiazolo[5,4-c]pyridine-7-carboxamide

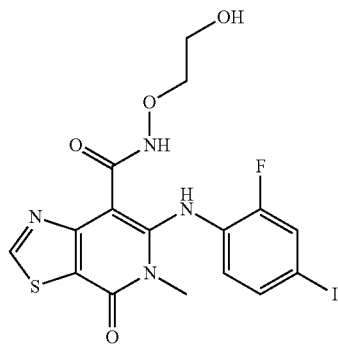 [SMILES: Cn1c(Nc2ccc(I)cc2F)c(C(=O)NOCCO)c2ncsc2c1=O]

Step A: ethyl 4-(2-ethoxy-2-oxoethyl)thiazole-5-carboxylate

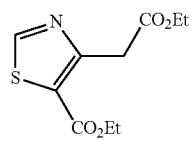 [SMILES: CCOC(=O)Cc1ncsc1C(=O)OCC]

To a neat diethyl 3-oxopentanedioate (5.0 g, 25 mmol) was added sulfurous dichloride (2 mL, 25 mol) dropwise at 0° C., the mixture was then stirred at rt for 2 h followed by heated at 50° C. for 0.5 h. The resulting solution was added dropwise to a solution of methanethioamide (1.51 g, 25 mol) in EtOH (15 mL). The mixture was reflux for 0.5 h and added into ice water, the precipitate was filtered off and dried to afford the title compound (2 g, 33%). ¹H NMR (400 MHz, CDCl₃) δ 8.82 (s, 1H), 4.35 (q, J=7.2 Hz, 2H), 4.26 (s, 2H), 4.19 (q, J=7.2 Hz, 2H), 1.37 (t, J=7.2 Hz, 3H), 1.26 (t, J=7.2 Hz, 3H).

Step B: ethyl 6-(2-fluoro-4-iodophenylamino)-5-methyl-4-oxo-4,5-dihydrothiazolo[5,4-c]pyridine-7-carboxylate

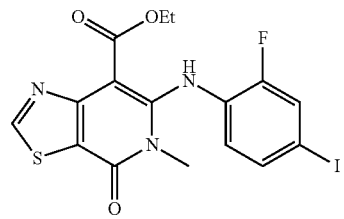 [SMILES: CCOC(=O)c1c(Nc2ccc(I)cc2F)n(C)c(=O)c2scnc12]

According to the procedure B, ethyl 4-(2-ethoxy-2-oxoethyl)thiazole-5-carboxylate was reacted with 2-fluoro-4-iodo-N-((methylimino)methylene)aniline to obtain the desired product via column chromatography purification. ¹H NMR (400 MHz, CDCl₃) δ 9.50 (s, 1H), 9.19 (s, 1H), 7.50 (dd, J=10.0 & 2.0 Hz, 1H), 7.37 (d, J=8.4 Hz, 1H), 6.44 (t, J=8.4 Hz, 1H), 4.46 (q, J=7.2 Hz, 2H), 3.44 (s, 3H), 1.41 (t, J=7.2 Hz, 1H).

Step C: 6-(2-fluoro-4-iodophenylamino)-5-methyl-4-oxo-4,5-dihydrothiazolo[5,4-c]pyridine-7-carboxylic acid

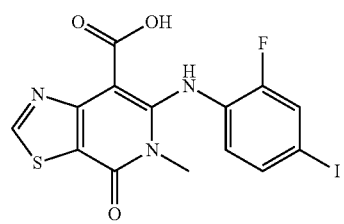

Following the same procedure as step C, example 1 described, the title product was obtained. ¹H NMR (400 MHz, DMSO-D6) δ 13.20 (brs, 1H), 9.65 (s, 1H), 7.66-7.69 (d, J=11.2 Hz, 1H), 7.40-7.42 (d, J=8.0 Hz, 1H), 6.72-6.74 (t, J=8.8 Hz, 1H), 3.36 (s, 3H).

Step D: 6-(2-fluoro-4-iodophenylamino)-N-(2-hydroxyethoxy)-5-methyl-4-oxo-4,5-dihydrothiazolo[5,4-c]pyridine-7-carboxamide

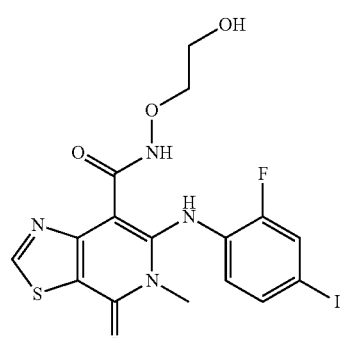

Following the same procedure as step D, example 1 described, the title product was obtained. $^1$H NMR (400 MHz, CDCl$_3$) δ 12.36 (s, 1H), 11.36 (s, 1H), 9.15 (s, 1H), 7.48-7.51 (d, J=9.6 Hz, 1H), 7.40-7.42 (d, J=8.4 Hz, 1H), 6.60 (t, J=8.4 Hz, 1H), 4.08-4.10 (m, 2H), 3.76-3.77 (m, 2H), 3.36 (s, 3H); m/z=505 [M+1]$^+$, 527 [M+Na]$^+$, 428 [M-NHOCH$_2$CH$_2$OH]$^+$.

Example 34

6-(2-Fluoro-4-iodophenylamino)-N-(2-hydroxy-ethoxy)-5-methyl-2-(methylthio)-4-oxo-4,5-dihydrothiazolo[5,4-c]pyridine-7-carboxamide

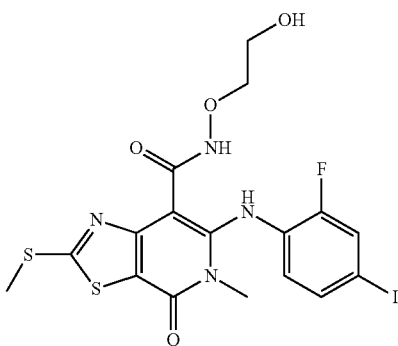 [SMILES: CSc1nc2c(C(=O)NOCCO)c(Nc3ccc(I)cc3F)n(C)c(=O)c2s1]

Step A: ethyl 4-(2-ethoxy-2-oxoethyl)-2-mercaptothiazole-5-carboxylate

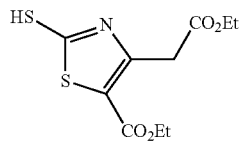

Sulfuryl dichloride (2 mL, 1.0 eq.) was added dropwise to diethyl 3-oxopentanedioate (neat, 5 g, 1.0 eq.) at 0° C. The mixture was stirred for 2 h at room temperature, and heated for 30 min at 50° C. The resulting solution was added dropwise to a solution of ammonium dithiocarbamate (2.3 g, 1.0 eq.) in EtOH (50 mL). The mixture was heated at 50° C. for at least 4 h until the precipitate was formed. The mixture was cooled and the solid was filtered off. The filtration was concentrated and purified by column chromatography (EtOAc/petroleum ether=1/5) to obtain the titled compound (1 g, 14.7%). $^1$H NMR (400 MHz, CDCl$_3$) δ 11.50 (brs, 1H), 4.22-4.32 (m, 4H), 4.10 (s, 2H), 1.29-1.36 (m, 6H).

Step B: ethyl 4-(2-ethoxy-2-oxoethyl)-2-(methylthio)thiazole-5-carboxylate

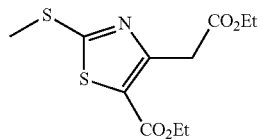

To a solution of ethyl 4-(2-ethoxy-2-oxoethyl)-2-mercaptothiazole-5-carboxylate (356 mg, 1.0 eq.) in acetone (10 ml) was added MeI (220 mg, 1.2 eq.) and K$_2$CO$_3$ (150 mg, 1.0 eq.) at 0° C. After warming to room temperature and stirring for 30 min, the solvent was removed in vacuum and the residue was purified by flash column chromatography (EtOAc/petroleum ether=1/20) to obtain the titled compound (150 mg, 50%). $^1$H NMR (400 MHz, CDCl$_3$) δ 4.30 (q, J=7.2 Hz, 2H), 4.20 (q, J=7.2 Hz, 2H), 4.17 (s, 2H), 2.69 (s, 3H), 1.34 (t, J=7.2 Hz, 3H), 1.26 (t, J=7.2 Hz, 3H).

Step C: ethyl 6-(2-fluoro-4-iodophenylamino)-5-methyl-2-(methylthio)-4-oxo-4,5-dihydrothiazolo[5,4-c]pyridine-7-carboxylate

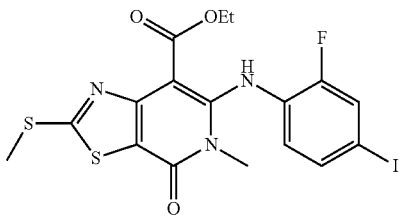

According to the procedure B, ethyl 4-(2-ethoxy-2-oxoethyl)-2-(methylthio)thiazole-5-carboxylate was reacted with 2-fluoro-4-iodo-N-((methylimino)methylene)aniline to obtain the desired product by column chromatography. $^1$H NMR (400 MHz, CDCl$_3$) δ 9.57 (s, 1H), 7.48 (dd, J=10.0 & 1.6 Hz, 1H), 7.36 (d, J=8.8 Hz, 1H), 6.42 (t, J=8.4 Hz, 1H), 4.38 (q, J=7.2 Hz, 2H), 3.40 (s, 3H), 2.81 (s, 3H), 1.41 (t, J=7.2 Hz, 3H).

Step D: 6-(2-fluoro-4-iodophenylamino)-5-methyl-4-oxo-4,5-dihydrothiazolo[5,4-c]pyridine-7-carboxylic acid

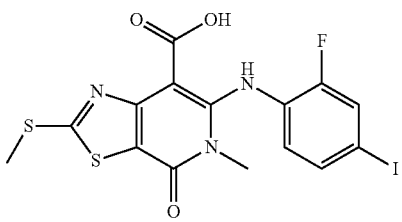 [SMILES: CSc1nc2c(C(=O)O)c(Nc3ccc(I)cc3F)n(C)c(=O)c2s1]

Following the same procedure as step C, example 1 described, the title product was obtained.

Step E: 6-(2-fluoro-4-iodophenylamino)-N-(2-hydroxyethoxy)-5-methyl-2-(methylthio)-4-oxo-4,5-dihydrothiazolo[5,4-c]pyridine-7-carboxamide

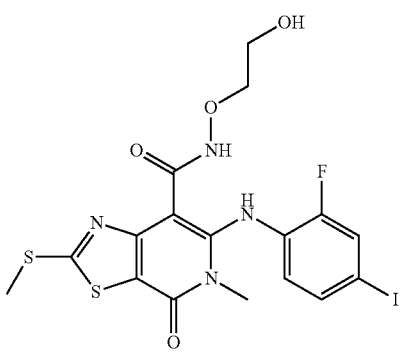 [SMILES: CSc1nc2c(C(=O)NOCCO)c(Nc3ccc(I)cc3F)n(C)c(=O)c2s1]

Following the same procedure as step D, example 1 described, the title product was obtained. $^1$H NMR (400

MHz, CD₃OD) δ 7.49 (d, J=10.0 Hz, 1H), 7.37 (d, J=6.8 Hz, 1H), 6.59 (t, J=8.4 Hz, 1H), 3.91 (m, 2H), 3.66 (m, 2H), 3.29 (s, 3H), 2.77 (s, 3H); m/z=551 [M+1]⁺, 573 [M+Na]⁺, 474 [M-NHOCH₂CH₂OH]⁺.

Example 35

6-(2-Chloro-4-iodophenylamino)-N-(3-hydroxypropyl)-5-methyl-4-oxo-4,5-dihydrofuro[3,2-c]pyridine-7-carboxamide

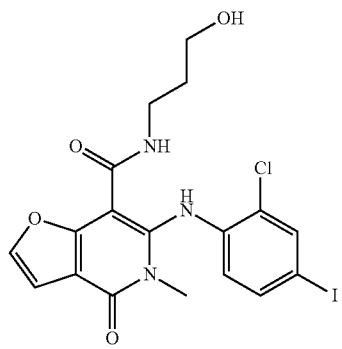 [SMILES: Cn1c(Nc2ccc(I)cc2Cl)c(C(=O)NCCCO)c2occc2c1=O]

According to procedure C, 6-(2-chloro-4-iodophenylamino)-5-methyl-4-oxo-4,5-dihydrofuro[3,2-c]pyridine-7-carboxylic acid was reacted with 3-methoxypropan-1-amine then treated with BBr₃ at 0° C. to get the desired product. ¹H NMR (400 MHz, CDCl₃) δ 11.19 (s, 1H), 7.77 (d, J=2.0 Hz, 1H), 7.68 (m, 1H), 7.51 (d, J=2.4 Hz, 1H), 7.43 (dd, J=8.4 & 2.0 Hz, 1H), 7.02 (d, J=2.4 Hz, 1H), 6.34 (d, J=8.4 Hz, 1H), 3.70-3.72 (m, 2H), 3.61-3.65 (m, 2H), 3.30 (s, 3H), 2.60 (brs, 1H), 1.81-1.87 (m, 2H); m/z=502 [M+1]⁺, 427 [M-NHCH₂CH₂CH₂OH]⁺.

Example 36

6-(2-chloro-4-iodophenylamino)-N-(2-hydroxyethoxy)-3,5-dimethyl-4-oxo-4,5-dihydrofuro[3,2-c]pyridine-7-carboxamide

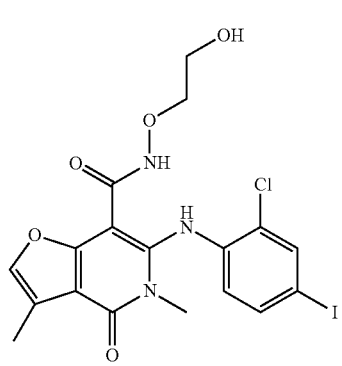

Step A: ethyl 6-(2-chloro-4-iodophenylamino)-3,5-dimethyl-4-oxo-4,5-dihydrofuro[3,2-c]pyridine-7-carboxylate

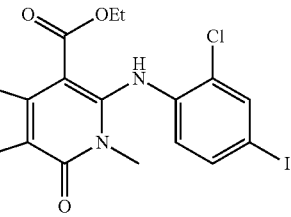

According to the procedure B, ethyl 2-(2-ethoxy-2-oxoethyl)-4-methylfuran-3-carboxylate was reacted with 2-chloro-4-iodo-N-((methylimino)methylene)aniline to obtain the desired product by column chromatography. ¹H NMR (400 MHz, CDCl₃) δ 9.69 (s, 1H), 7.77 (d, J=1.6 Hz, 1H), 7.43 (dd, J=2.0 & 8.4 Hz, 1H), 7.29 (q, J=1.2 Hz, 1H), 6.31 (d, J=8.4 Hz, 1H), 4.40 (q, J=6.8 Hz, 2H), 3.31 (s, 3H), 2.37 (d, J=1.2 Hz, 3H), 1.41 (t, J=6.8 Hz, 3H).

Step B: 6-(2-chloro-4-iodophenylamino)-3,5-dimethyl-4-oxo-4,5-dihydrofuro[3,2-c]pyridine-7-carboxylic acid

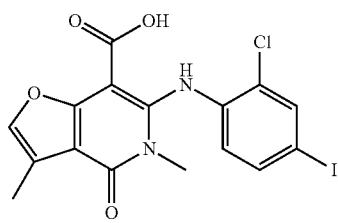 [SMILES: CCOC(=O)c1c(Nc2ccc(I)cc2Cl)n(C)c(=O)c2c(C)coc12]

Following the same procedure as step C, example 1 described, the title product was obtained.

Step C: 6-(2-chloro-4-iodophenylamino)-N-(2-hydroxyethoxy)-3,5-dimethyl-4-oxo-4,5-dihydrofuro[3,2-c]pyridine-7-carboxamide

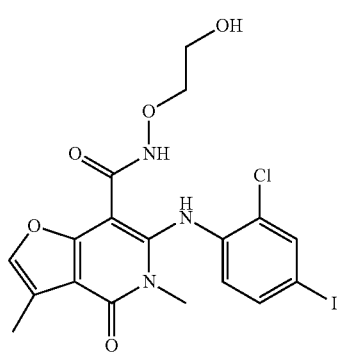 [SMILES: Cc1coc2c(C(=O)NOCCO)c(Nc3ccc(I)cc3Cl)n(C)c(=O)c12]

Following the same procedure as step D, example 1 described, the title product was obtained. ¹H NMR (400 MHz, DMSO-D6) δ 11.26 (s, 1H), 8.96 (s, 1H), 7.78 (d, J=2.0 Hz, 1H), 7.68 (s, 1H), 7.47 (dd, J=2.0 & 8.4 Hz, 1H), 6.45 (d, J=8.4 Hz, 1H), 4.64 (t, J=5.6 Hz, 1H), 3.73 (t, J=8.8 Hz, 2H), 3.51 (dt, J=8.8 & 5.6 Hz, 2H), 3.26 (s, 3H), 2.27 (s, 3H); m/z=441 [M-NHOCH$_2$CH$_2$OH]$^+$, 518 [M+1]$^+$.

Example 37

6-(2-Fluoro-4-iodophenylamino)-N-(2-hydroxyethoxy)-2,5-dimethyl-4-oxo-4,5-dihydrothiazolo[5,4-c]pyridine-7-carboxamide

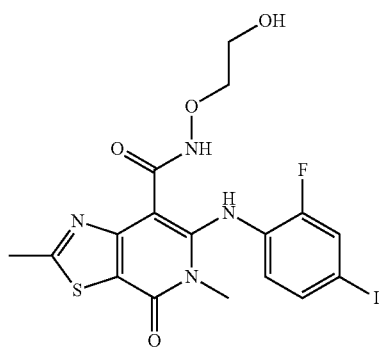 [SMILES: Cc1nc2c(C(=O)NOCCO)c(Nc3ccc(I)cc3F)n(C)c(=O)c2s1]

Step A: ethyl 4-(2-ethoxy-2-oxoethyl)-2-methylthiazole-5-carboxylate

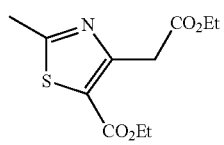

Sulfuryl dichloride (4 mL, 1.0 eq.) was added dropwise to diethyl 3-oxopentanedioate (neat, 10 g, 1.0 eq.) at 0° C. The mixture was stirred for 2 h at room temperature, and heated for 30 min at 50° C. The resulting solution was added dropwise to a solution of ethanethioamide (3.7 g, 1.0 eq.) in EtOH (100 mL). The mixture was heated at 50° C. for at least 4 h until the precipitate was formed. The mixture was cooled and the solid was filtered off. The filtration was concentrated and purified by column chromatography (EtOAc/petroleum ether=1/20) to obtain the titled compound (5.9 g, 46.4%). $^1$H NMR (400 MHz, CDCl$_3$) δ 4.31 (q, J=7.2 Hz, 2H), 4.18 (q, J=7.2 Hz, 2H), 4.17 (s, 2H), 2.70 (s, 3H), 1.34 (t, J=7.2 Hz, 3H), 1.26 (t, J=7.2 Hz, 3H).

Step B: ethyl 6-(2-fluoro-4-iodophenylamino)-2,5-dimethyl-4-oxo-4,5-dihydrothiazolo[5,4-c]pyridine-7-carboxylate

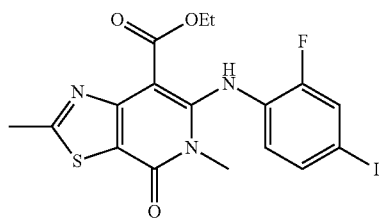

According to the procedure B, ethyl 4-(2-ethoxy-2-oxoethyl)-2-methylthiazole-5-carboxylate was reacted with 2-fluoro-4-iodo-N-((methylimino)methylene)aniline to obtain the desired product by column chromatography. $^1$H NMR (400 MHz, DMSO-D6) δ 8.62 (s, 1H), 7.59 (dd, J=10.8 & 1.6 Hz, 1H), 7.34 (d, J=8.4 Hz, 1H), 6.60 (t, J=8.8 Hz, 1H), 3.96 (q, J=7.2 Hz, 2H), 3.44 (s, 3H), 2.79 (s, 3H), 1.02 (t, J=7.2 Hz, 3H).

Step C: 6-(2-fluoro-4-iodophenylamino)-2,5-dimethyl-4-oxo-4,5-dihydrothiazolo[5,4-c]pyridine-7-carboxylic acid

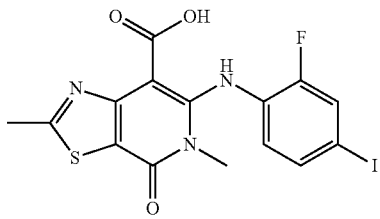 [SMILES: CCOC(=O)c1c(Nc2ccc(I)cc2F)n(C)c(=O)c2sc(C)nc12]

Following the same procedure as step C, example 1 described, the title product was obtained. $^1$H NMR (400 MHz, DMSO-D6) δ 13.30 (brs, 1H), 9.60 (s, 1H), 7.67 (dd, J=10.4 & 1.2 Hz, 1H), 7.42 (d, J=8.4 Hz, 1H), 6.76 (t, J=8.4 Hz, 1H), 3.29 (s, 3H), 2.86 (s, 3H).

Step D: 6-(2-fluoro-4-iodophenylamino)-N-(2-hydroxyethoxy)-2,5-dimethyl-4-oxo-4,5-dihydrothiazolo[5,4-c]pyridine-7-carboxamide

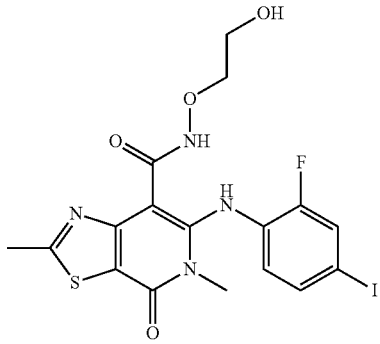 [SMILES: Cc1nc2c(C(=O)NOCCO)c(Nc3ccc(I)cc3F)n(C)c(=O)c2s1]

Following the same procedure as step D, example 1 described, the title product was obtained. $^1$H NMR (400 MHz, CD$_3$OD) δ 7.49 (dd, J=10.4 & 1.6 Hz, 1H), 7.37 (d, J=8.4 Hz, 1H), 6.57 (t, J=8.4 Hz, 1H), 3.93 (t, J=4.4 Hz, 2H), 3.66 (t, J=4.4 Hz, 2H), 3.28 (s, 3H), 2.80 (s, 3H); m/z=442 [M-NHOCH$_2$CH$_2$OH]$^+$, 519 [M+1]$^+$.

Example 38

6-(2-Fluoro-4-iodophenylamino)-7-(3-hydroxy-3-(piperidin-2-yl)azetidine-1-carbonyl)-5-methylfuro[3,2-c]pyridin-4(5H)-one

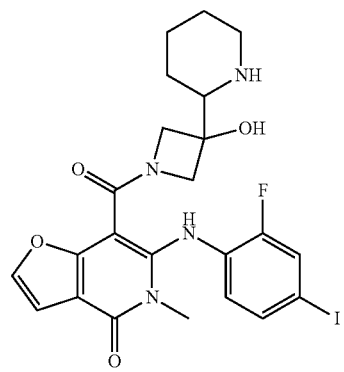 [SMILES: Cn1c(Nc2ccc(I)cc2F)c(C(=O)N2CC(O)(C3CCCCN3)C2)c2occc2c1=O]

Step A: tert-butyl 2-(1-(benzyloxycarbonyl)-3-hydroxyazetidin-3-yl)piperidine-1-carboxylate

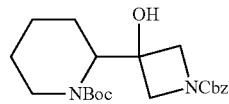

According to *J. Org. Chem.*, 1990, 55, 2578-2580 and WO2007/044515, tert-butyl piperidine-1-carboxylate was '-lithiation with sec-BuLi in ethyl ether, followed by reacting with benzyl 3-oxoazetidine-1-carboxylate to afford the title compound (yield=11%). $^1$H NMR (400 MHz, CDCl$_3$) δ 7.27-7.37 (m, 5H), 5.40 (brs, 1H), 5.09 (s, 2H), 4.03 (d, J=9.2 Hz, 1H), 3.94 (d, J=9.2 Hz, 1H), 3.82-3.86 (m, 3H), 3.49 (brs, 1H), 3.06 (brs, 1H), 1.90-1.95 (m, 1H), 1.50-1.63 (m, 5H), 1.44 (s, 9H).

Step B: tert-butyl 2-(3-hydroxyazetidin-3-yl)piperidine-1-carboxylate

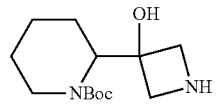

Tert-butyl 2-(1-(benzyloxycarbonyl)-3-hydroxyazetidin-3-yl)piperidine-1-carboxylate and 10% Pd/C were taken into methanol and the mixture hydrogenated at ambient pressure for 1 h. After filtration, the filtrate was concentrated to get the title product. $^1$H NMR (400 MHz, CD$_3$OD) δ 4.29-4.32 (m, 1H), 3.85 (brs, 1H), 3.72 (d, J=8.8 Hz, 1H), 3.54 (d, J=9.2 Hz, 1H), 3.42 (d, J=9.6 Hz, 1H), 3.39 (d, J=9.2 Hz, 1H), 3.35-3.42 (brs, 1H), 1.90-1.96 (m, 1H), 1.73-1.78 (m, 1H), 1.54-1.63 (m, 4H), 1.47 (s, 9H).

Step C: tert-butyl 2-(1-(6-(2-fluoro-4-iodophenylamino)-5-methyl-4-oxo-4,5-dihydrofuro[3,2-c]pyridine-7-carbonyl)-3-hydroxyazetidin-3-yl)piperidine-1-carboxylate

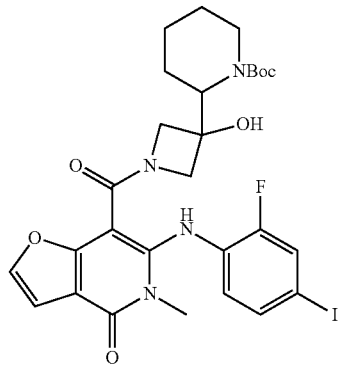 [SMILES: Cn1c(Nc2ccc(I)cc2F)c(C(=O)N2CC(O)(C3CCCCN3C(=O)OC(C)(C)C)C2)c2occc2c1=O]

According to procedure C, 6-(2-fluoro-4-iodophenylamino)-5-methyl-4-oxo-4,5-dihydrofuro[3,2-c]pyridine-7-carboxylic acid was coupling with tert-butyl 2-(3-hydroxyazetidin-3-yl)piperidine-1-carboxylate to obtain the title product. $^1$H NMR (400 MHz, CDCl$_3$) δ 9.01 (brs, 1H), 7.47 (d, J=1.6 Hz, 1H), 7.46 (dd, J=10.0 & 1.6 Hz, 1H), 7.34 (d, J=8.8 Hz, 1H), 6.99 (d, J=1.6 Hz, 1H), 6.35 (t, J=8.8 Hz, 1H), 3.78-4.19 (m, 6H), 3.43 (s, 3H), 1.55-3.12 (m, 8H), 1.41 (s, 9H).

Step D: 6-(2-fluoro-4-iodophenylamino)-7-(3-hydroxy-3-(piperidin-2-yl)azetidine-1-carbonyl)-5-methylfuro[3,2-c]pyridin-4(5H)-one

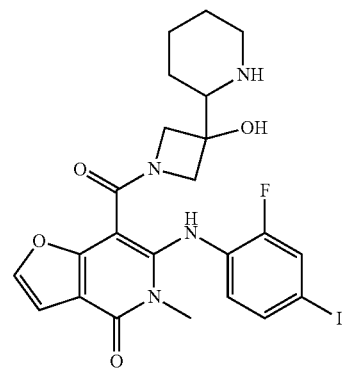 [SMILES: Cn1c(Nc2ccc(I)cc2F)c(C(=O)N2CC(O)(C3CCCCN3)C2)c2occc2c1=O]

Tert-butyl 2-(1-(6-(2-fluoro-4-iodophenylamino)-5-methyl-4-oxo-4,5-dihydrofuro[3,2-c]pyridine-7-carbonyl)-3-hydroxyazetidin-3-yl)piperidine-1-carboxylate was dissolved in the solution of 4N HCl in dioxane, then heated under reflux to obtain the product. $^1$H NMR (400 MHz, DMSO-D6) δ 8.51 (brs, 1H), 7.91 (d, J=2.0 Hz, 1H), 7.58 (d, J=10.8 Hz, 1H), 7.34 (d, J=9.2 Hz, 1H), 7.00 (d, J=2.0 Hz, 1H), 6.61 (t, J=9.2 Hz, 1H), 5.60 (brs, 1H), 3.65-3.88 (m, 3H), 3.48-3.53 (m, 1H), 3.39 (s, 3H), 2.88-2.92 (m, 1H), 2.42-2.49 (m, 1H), 2.26-2.33 (m, 1H), 1.60-1.70 (m, 2H), 1.40-1.50 (m, 4H); m/z=567 [M+1]$^+$.

Example 39

6-(2-chloro-4-iodophenylamino)-N-(2-hydroxyethoxy)-5-methyl-2-(methylthio)-4-oxo-4,5-dihydrothiazolo[5,4-c]pyridine-7-carboxamide

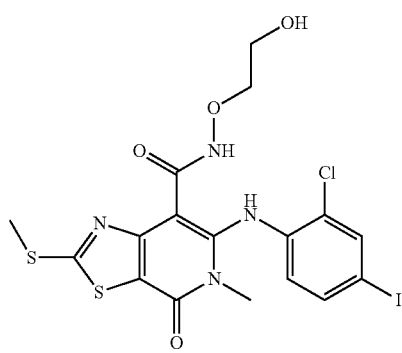 [SMILES: CSc1nc2c(C(=O)NOCCO)c(Nc3ccc(I)cc3Cl)n(C)c(=O)c2s1]

Step A: ethyl 6-(2-chloro-4-iodophenylamino)-5-methyl-2-(methylthio)-4-oxo-4,5-dihydrothiazolo[5,4-c]pyridine-7-carboxylate

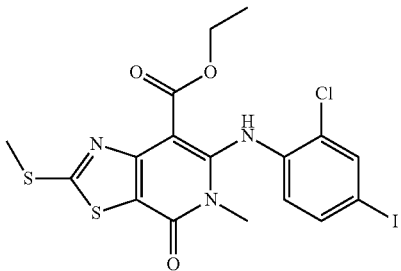 [SMILES: CCOC(=O)c1c(Nc2ccc(I)cc2Cl)n(C)c(=O)c2sc(SC)nc12]

According to the procedure B, ethyl 4-(2-ethoxy-2-oxoethyl)-2-(methylthio)thiazole-5-carboxylate was reacted with 2-chloro-4-iodo-N-((methylimino)methylene)aniline to obtain the desired product by column chromatography. $^1$H NMR (400 MHz, DMSO-D6) δ 8.65 (brs, 1H), 7.77 (d, J=1.6 Hz, 1H), 7.46 (dd, J=8.4 & 1.6 Hz, 1H), 6.57 (d, J=8.4 Hz, 1H), 4.02 (q, J=7.2 Hz, 2H), 3.36 (s, 3H), 2.79 (s, 3H), 1.08 (t, J=7.2 Hz, 3H).

Step B: 6-(2-chloro-4-iodophenylamino)-5-methyl-2-(methylthio)-4-oxo-4,5-dihydrothiazolo[5,4-c]pyridine-7-carboxylic acid

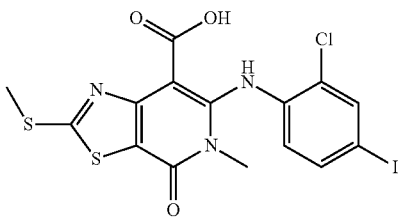 [SMILES: CSc1nc2c(C(=O)O)c(Nc3ccc(I)cc3Cl)n(C)c(=O)c2s1]

Following the same procedure as step C, example 1 described, the title product was obtained. $^1$H NMR (400 MHz, DMSO-D6) δ 13.10 (brs, 1H), 9.58 (brs, 1H), 7.84 (d, J=2.0 Hz, 1H), 7.51 (dd, J=8.8 & 2.0 Hz, 1H), 6.65 (d, J=8.8 Hz, 1H), 3.22 (s, 3H), 2.81 (s, 3H).

Step C: 6-(2-chloro-4-iodophenylamino)-N-(2-hydroxyethoxy)-5-methyl-2-(methylthio)-4-oxo-4,5-dihydrothiazolo[5,4-c]pyridine-7-carboxamide

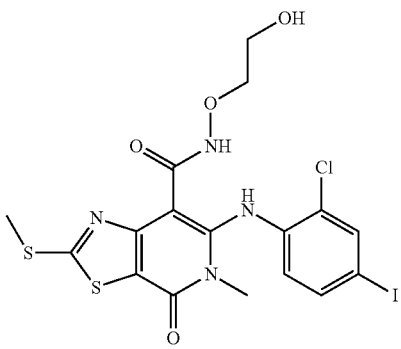

Following the same procedure as step D, example 1 described, the title product was obtained. $^1$H NMR (400 MHz, CD$_3$OD) δ 7.75 (d, J=1.6 Hz, 1H), 7.47 (dd, J=8.4 & 2.0 Hz, 1H), 6.47 (d, J=8.4 Hz, 1H), 3.92 (t, J=4.8 Hz, 2H), 3.66 (t, J=4.8 Hz, 2H), 3.24 (s, 3H), 2.78 (s, 3H); m/z=490 [M-NHOCH$_2$CH$_2$OH]$^+$, 567 [M+1]$^+$.

Biological Activity

Materials and Preparation of Reagents:

The Kinase Glo plus assay kit was purchased from Promega. The substrate, APT, DTT, and dimethylsulfoxide were purchased from Sigma-Aldrich.

The MAP2K1 (MEK1) kinase, Europium labeled Antibody, Tracer 236 and binding buffer A were purchased from Invitrogen.

The Recombinant Human Epithelial Growth Factor (EGF) was purchased from R&D System.

The SureFire Phospho-ERK1/2 Assay kit and the AlphaScreen General IgG (Protein A) Detection kit were both purchased from PerkinElmer.

Generation of IC$_{50}$ Data

Determination of Enzymatic Activity:

Compounds were diluted from DMSO stocks into 1× buffer (20 mM MOPS, PH 7.4, 5 mM MgCl$_2$, 0.5 mM MnCl$_2$, 100 uM Sodium Orthovanadate, 0.01% Triton X-100, 1 mM DTT). A typical reaction assay contained 0.01 nanomoles MEK1 kinase, 0.01 nanomoles ATP, 10 nanograms substrate. The screening assay essentially comprised four additions. 2 ul of diluted compounds were dispensed to 384 well white assay plates. 6 ul of kinase-substrate cocktail was then added to each well. 2 ul 5×ATP was subsequently added to each well to start the reaction. A top seal was applied and the plate was incubated at 22 degree avoiding light for 60 minutes. Finally, 10 ul of the Kinase Glo plus reagent was added to each well to stop the reaction. Incubated at room temperature and avoid light for ten minutes. The top seal was removed and the plate was counted by the EnVision 2104 multi labeled plate reader (PerkinElmer) with a standard luminescent program. The intensity of luminescent signal was quantitated and this data was used to generate dose response curves and IC$_{50}$ calculations by the Prism program.

Generation of Cell Based IC$_{50}$ Data

Effects of compounds in the cell were determined by the AlphaScreen assay for phosphorylated ERK. Human A375 melanoma cancer cells were plated in a 96 wells plate at 80,000 cells per well and grown in a 37 degree humidified CO$_2$ incubator. The following day, cells were treated with a range of compound concentrations for 60 minutes at 37 degree. The cells were then lysed and 4 ul of each lysate were transferred into the 384 well white reaction plate. A cocktail of AlphaScreen beads and buffer was freshly prepared and this mixture was dispensed into each well in a room with low light. A top seal was applied and the plate was incubated at 25 degree avoiding light for two hours. The top seal was removed when the plate was counted by the EnVision multi labeled plate reader (PerkinElmer) with an optimized AlphaScreen program. The intensity of signal was quantitated and this data was used to generate dose response curves and IC$_{50}$ calculations by the Prism program.

Biological Data for Select Compounds

Select compounds prepared as described above were assayed according to the biological procedures described herein. The results are given in the table below:

| Structure | IC$_{50}$ (nM) Kinase Activity | IC$_{50}$ (nM) Cell based |
|---|---|---|
| (structure) | <100 | <100 |
| (structure) | <500 | <100 |
| (structure) | <10000 | <100 |
| (structure) | <100 | <100 |
| (structure) | <100 | <100 |
| (structure) | <500 | <100 |
| (structure) | <100 | <100 |
| (structure) | <100 | <100 |
| (structure) | <100 | <100 |
| (structure) | <100 | <100 |

91
-continued

| Structure | IC₅₀ (nM) Kinase Activity | IC₅₀ (nM) Cell based |
|---|---|---|
| (furopyridinone with 2,4-diCl-anilino, N-Me, C(O)NH-O-CH₂CH₂OH) | <10000 | <1000 |
| (furopyridinone with 2-Cl-4-Br-anilino, N-Me, C(O)NH-O-CH₂CH₂OH) | <1000 | <100 |
| (furopyridinone with 2-F-4-I-anilino, N-Me, C(O)NH-OMe) | <500 | <100 |
| (furopyridinone with 2-F-4-I-anilino, N-Me, C(O)NH-OEt) | <500 | <100 |
| (furopyridinone with 2-F-4-I-anilino, N-Me, C(O)NH₂) | <1000 | <100 |
| (furopyridinone with 2-F-4-I-anilino, N-Me, C(O)NH-CH₂CH(OH)CH₂OH) | <1000 | <100 |

92
-continued

| Structure | IC₅₀ (nM) Kinase Activity | IC₅₀ (nM) Cell based |
|---|---|---|
| (furopyridinone with 2-Cl-4-I-anilino, N-Me, C(O)NH-O-CH₂CH₂OH) | <100 | <100 |
| (furopyridinone with 2-F-4-I-anilino, N-Me, C(O)NH-CH₂CH₂CH₂OH) | <10000 | <100 |
| (thienopyridinone with 2-F-4-I-anilino, N-Me, C(O)NH-O-CH₂CH₂OH) | <500 | <100 |
| (furopyridinone with 2-F-4-SMe-anilino, N-Me, C(O)NH-O-CH₂CH₂OH) | <500 | <100 |
| (furopyridinone with 2-Cl-4-SMe-anilino, N-Me, C(O)NH-O-CH₂CH₂OH) | <1000 | <100 |

-continued

| Structure | IC₅₀ (nM) | |
|---|---|---|
| | Kinase Activity | Cell based |
| 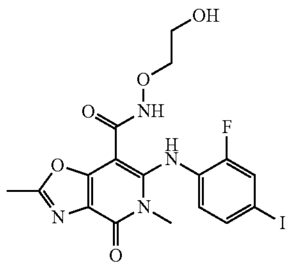 [SMILES: Cc1nc2c(=O)n(C)c(Nc3ccc(I)cc3F)c(C(=O)NOCCO)c2o1] | <1000 | <100 |
| | <10000 | <100 |
| | <500 | <100 |
| | <10000 | <10000 |
| | <500 | <100 |

-continued

| Structure | IC₅₀ (nM) | |
|---|---|---|
| | Kinase Activity | Cell based |
| | <500 | <100 |
| | <500 | <100 |
| 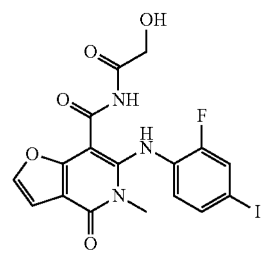 [SMILES: Cn1c(Nc2ccc(I)cc2F)c(C(=O)NC(=O)CO)c2occc2c1=O] | <10000 | <500 |
| | <500 | <100 |
| | <500 | <100 |

95
-continued

| Structure | IC50 (nM) Kinase Activity | IC50 (nM) Cell based |
|---|---|---|
|  | <500 | <100 |
| 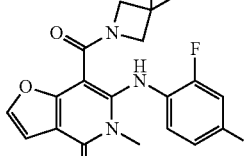 | <1000 | <100 |
| 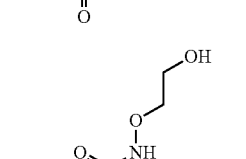 | <10000 | <100 |
| 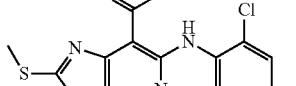 | <500 | <100 |
| 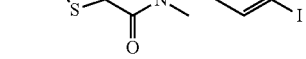 | <500 | <100 |

96
-continued

| Structure | IC50 (nM) Kinase Activity | IC50 (nM) Cell based |
|---|---|---|
| 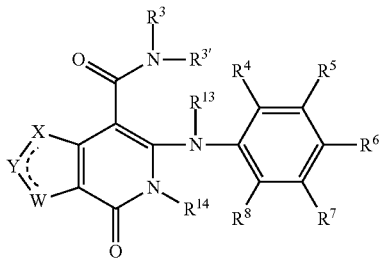 | <1000 | <100 |
| 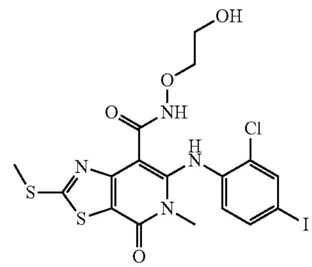 [SMILES: CSc1nc2c(C(=O)NOCCO)c(Nc3ccc(I)cc3Cl)n(C)c(=O)c2s1] | <100 | <100 |

What is claimed is:

1. A compound of formula I

Formula I wherein

╌╌╌ represents X—Y=W or W—Y=X,

X independently represent N, O, or S;

W is $CR_2$, N, or S;

Y is N or $CR^1$; and $R^1$ is selected from the group consisting of H and $C_1$-$C_6$ alkyl; wherein each alkyl is optionally substituted with 1-3 substituents selected independently from the group consisting of halogen, hydroxy, amino, $C_1$-$C_6$ alkylamino, di$C_1$-$C_6$ alkylamino, and $C_1$-$C_6$ heterocyclyl;

$R^2$ is selected from the group consisting of H and $C_1$-$C_{10}$ alkyl, where each alkyl is unsubstituted or substituted with 1-3 substituents selected independently from halogen, hydroxyl, and $C_1$-$C_4$ alkyl;

$R^3$ is selected from the group consisting of H, $C_1$-$C_{10}$ alkyl, $C_1$-$C_{10}$ alkoxy, $C_3$-$C_{10}$ cycloalkyl, $C_3$-$C_{10}$ cycloalkylalkyl, where each alkyl, alkoxy, and cycloalkyl is unsubstituted or substituted with 1-3 substituents selected independently from the group consisting of halogen, hydroxyl, $C_1$-$C_4$ alkyl, and $C_1$-$C_4$ alkoxy;

$R^{3'}$ is selected from the group consisting of H and $C_1$-$C_6$ alkyl;

$R^4$, $R^5$, $R^6$, $R^7$ and $R^8$ are independently selected from the group consisting of H, halogen, $SR^9$, and $OR^9$;

$R^9$ is selected from the group consisting of hydrogen and $C_1$-$C_{10}$ alkyl;

$R^{13}$ is selected from the groups consisting of H and $C_1$-$C_6$ alkyl; and $R^{14}$ is selected from the groups consisting of H and $C_1$-$C_6$ alkyl;

or a pharmaceutically acceptable salt, solvate, polymorph, or tautomer thereof.

2. The compound according to claim 1, wherein Y is $CR^1$.

3. The compound according to claim 1, wherein ----- represents X—Y=W; X is O or S; Y is $CR^1$; and W is $CR^2$.

4. The compound according to claim 1, wherein $R^3$ is selected from the group consisting of hydrogen, $C_1$-$C_6$ alkyl optionally substituted with one or more substituents selected from the group consisting of halogen, hydroxyl and $C_1$-$C_4$ alkoxy; $C_1$-$C_6$ alkoxyl optionally substituted with one or more substituents selected from the group consisting of halogen and hydroxyl; $C_3$-$C_6$ cycloalkyl optionally substituted with $C_1$-$C_4$ alkyl.

5. The compound according to claim 4, wherein $R^3$ is selected from the group consisting of $C_1$-$C_6$ alkyl and $C_1$-$C_6$ alkoxy, where alkyl and alkoxy are independently unsubstituted or substituted with one or more substituents selected independently from the group consisting of halogen and hydroxyl.

6. The compound according to claim 1, wherein $R^4$, $R^5$, $R^6$, $R^7$ and $R^8$ are independently selected from H or halogen.

7. The compound according to claim 6, wherein one of $R^4$ and $R^8$ is fluorine or chlorine, and $R^6$ is iodine.

8. The compound according to claim 7 which is selected from the following

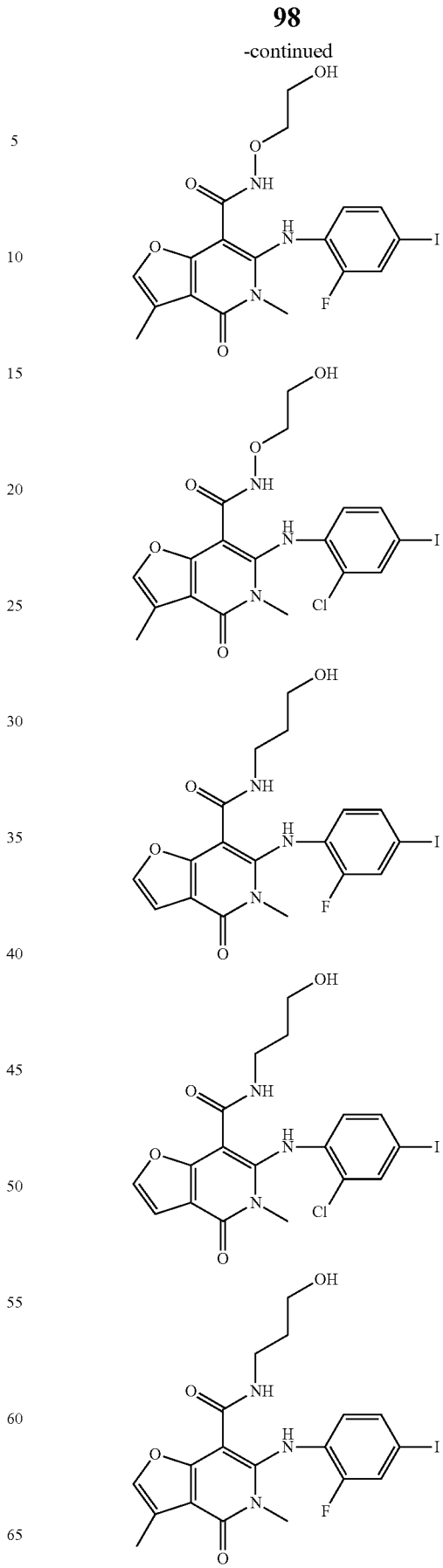

99
-continued
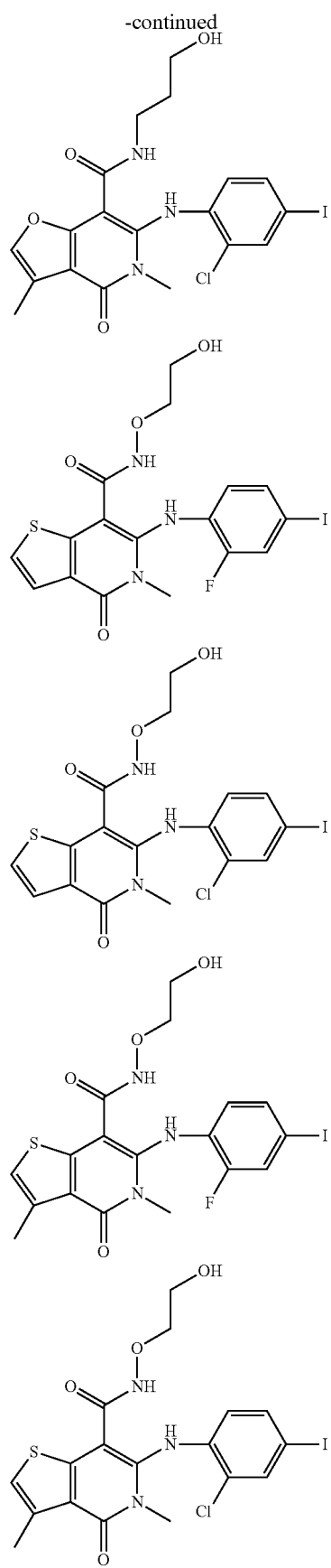
100
-continued
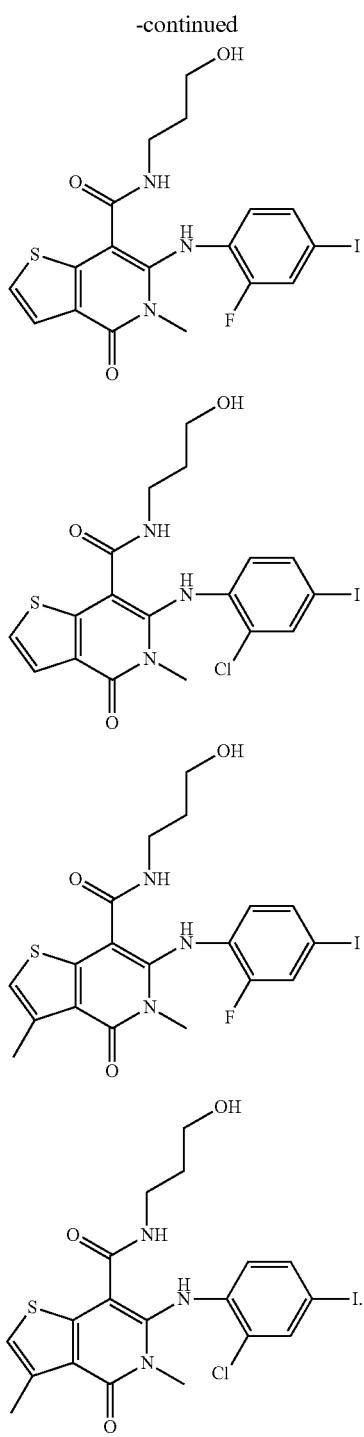
9. A pharmaceutical composition comprising a pharmaceutically effective amount of the compound of claim 1 and a pharmaceutically acceptable carrier.
10. A method for the treatment of a MEK mediated disorder or disease in a subject comprising administration of the compound of claim 1, wherein the MEK mediated disorder or disease is melanoma.
* * * * *